US010092009B2

(12) United States Patent
Thompson et al.

(10) Patent No.: US 10,092,009 B2
(45) Date of Patent: Oct. 9, 2018

(54) FUSION PROTEINS AND METHODS FOR STIMULATING PLANT GROWTH, PROTECTING PLANTS FROM PATHOGENS, AND IMMOBILIZING BACILLUS SPORES ON PLANT ROOTS

(71) Applicant: Spogen Biotech Inc., St. Louis, MO (US)

(72) Inventors: Brian Thompson, Creve Coeur, MO (US); Katie Thompson, Creve Coeur, MO (US)

(73) Assignee: Spogen Biotech Inc., St. Louis, MO (US)

( * ) Notice: Subject to any disclaimer, the term of this patent is extended or adjusted under 35 U.S.C. 154(b) by 52 days.

(21) Appl. No.: 15/414,050

(22) Filed: Jan. 24, 2017

(65) Prior Publication Data

US 2017/0135353 A1 May 18, 2017

Related U.S. Application Data

(62) Division of application No. 14/213,525, filed on Mar. 14, 2014, now Pat. No. 9,573,980.

(60) Provisional application No. 61/799,262, filed on Mar. 15, 2013.

(51) Int. Cl.

| | |
|---|---|
| ***C12N 15/62*** | (2006.01) |
| ***A01N 63/00*** | (2006.01) |
| ***C12N 9/02*** | (2006.01) |
| ***C12N 9/42*** | (2006.01) |
| ***C12N 9/48*** | (2006.01) |
| ***C12N 9/20*** | (2006.01) |

(52) U.S. Cl.

CPC ........... *A01N 63/00* (2013.01); *C12N 9/0095* (2013.01); *C12N 9/20* (2013.01); *C12N 9/2437* (2013.01); *C12N 9/48* (2013.01); *C12Y 118/06001* (2013.01); *C12Y 301/01003* (2013.01); *C12Y 302/01004* (2013.01); *C12Y 304/00* (2013.01)

(58) Field of Classification Search

CPC ........ A01N 37/44; A01N 63/02; C07K 14/32; C12N 15/62; C12N 15/75

See application file for complete search history.

(56) References Cited

U.S. PATENT DOCUMENTS

| | | | |
|---|---|---|---|
| 5,290,914 | A | 3/1994 | Wilcox et al. |
| 5,776,448 | A | 7/1998 | Suslow et al. |
| 6,184,440 | B1 | 2/2001 | Shoseyov et al. |
| 6,333,302 | B1 | 12/2001 | Beer et al. |
| 6,548,743 | B1 | 4/2003 | Sheen et al. |
| 7,615,681 | B2 | 11/2009 | Georges et al. |
| 7,919,678 | B2 | 4/2011 | Mironov |
| 8,030,064 | B2 | 10/2011 | Lee et al. |
| 8,461,419 | B2 | 6/2013 | He et al. |
| 9,068,194 | B2 | 6/2015 | Unkefer et al. |
| 9,132,175 | B2 | 9/2015 | Stewart et al. |
| 9,573,980 | B2 * | 2/2017 | Thompson ............. A01N 63/02 |
| 2003/0228679 | A1 | 12/2003 | Smith et al. |
| 2004/0077090 | A1 | 4/2004 | Short |
| 2008/0248953 | A1 | 10/2008 | Smith et al. |
| 2009/0192040 | A1 | 7/2009 | Grobler |
| 2010/0205690 | A1 | 8/2010 | Blasing et al. |
| 2010/0233124 | A1 | 9/2010 | Stewart et al. |
| 2010/0291100 | A1 | 11/2010 | Macinga |
| 2011/0281316 | A1 | 11/2011 | Stewart et al. |
| 2011/0321197 | A1 | 12/2011 | Schon et al. |
| 2012/0227134 | A1 | 9/2012 | Schon et al. |
| 2012/0259101 | A1 | 10/2012 | Tan et al. |
| 2012/0266327 | A1 | 10/2012 | Sanz Molinero et al. |
| 2013/0216653 | A1 | 8/2013 | Perkins et al. |
| 2014/0259225 | A1 | 9/2014 | Frank et al. |
| 2014/0342905 | A1 | 11/2014 | Bullis et al. |
| 2016/0051656 | A1 | 2/2016 | Stewart et al. |
| 2016/0053222 | A1 | 2/2016 | Stewart et al. |

FOREIGN PATENT DOCUMENTS

| | | | |
|---|---|---|---|
| CA | 2146822 | A1 | 10/1995 |
| EP | 0 792 363 | B1 | 12/2003 |
| EP | 1 590 466 | B1 | 9/2010 |
| EP | 2 069 504 | B1 | 6/2015 |
| RU | 2 458 132 | C2 | 8/2012 |
| WO | 02/00232 | A2 | 1/2002 |

(Continued)

OTHER PUBLICATIONS

Bae, C., et al., Multiple Classes of Immune-Related Proteases Associated with the Cell Death Response in Pepper Plants, PLOS ONE, 2013, e63533, vol. 8, No. 5.

Berlemont, R., et al., "Phylogenetic Distribution of Potential Cellulases in Bacteria," Applied and Environmental Microbiology, Mar. 2013, pp. 1545-1554, vol. 79, No. 5.

Chapman, K. D., "Phospholipase Activity During Plant Growth and Development and in Response to Environmental Stress," Trends in Plant Science, Nov. 1998, pp. 419-426, vol. 3, No. 11.

Choudhary, D. K., et al., "Interactions of *Bacillus* spp. and Plants—With Special Reference to Induced Systemic Resistance (ISR)," Microbiological Research, 2009, pp. 493-513, vol. 164.

(Continued)

*Primary Examiner* — Karen Cochrane Carlson

(74) *Attorney, Agent, or Firm* — Senniger Powers LLP

(57) ABSTRACT

The present invention is generally directed to fusion proteins containing a targeting sequence that targets the fusion protein to the exosporium of a *Bacillus cereus* family member. The invention also relates to recombinant *Bacillus cereus* family members expressing such fusion proteins, formulations containing the recombinant *Bacillus cereus* family members expressing the fusion proteins. Methods for stimulating plant growth and for protecting plants from pathogens by applying the recombinant *Bacillus cereus* family members or the formulations to plants or a plant growth medium are also described. The invention also relates to methods for immobilizing spores of a recombinant *Bacillus cereus* family member expressing a fusion protein on plant roots.

49 Claims, 1 Drawing Sheet

Specification includes a Sequence Listing.

(56) References Cited

FOREIGN PATENT DOCUMENTS

| | | | |
|---|---|---|---|
| WO | 2003/066846 | A1 | 8/2003 |
| WO | 2005/028654 | A1 | 3/2005 |
| WO | 2006/012366 | A2 | 2/2006 |
| WO | 2007/078127 | A1 | 7/2007 |
| WO | 2007/086898 | A2 | 8/2007 |
| WO | 2008/017483 | A2 | 2/2008 |
| WO | 2009/037329 | A1 | 3/2009 |
| WO | 2010/046221 | A1 | 4/2010 |
| WO | 2011/106794 | A1 | 9/2011 |
| WO | 2011/121408 | A1 | 10/2011 |
| WO | 2013/178649 | A1 | 12/2013 |
| WO | 2013/178658 | A1 | 12/2013 |
| WO | 2014/004487 | A1 | 1/2014 |
| WO | 2014/079773 | A1 | 5/2014 |
| WO | 2014/079814 | A1 | 5/2014 |
| WO | 2015/118516 | A1 | 8/2015 |

OTHER PUBLICATIONS

Ciabattini, A., et al., "Oral Priming of Mice by Recombinant Spores of Bacillus subtilis," Vaccine, Oct. 2004, pp. 4139-4143, vol. 22, Nos. 31-32.

Corbineau, F, et al., "Improvement of Germination of Terminalia ivorensis Seeds", Forest Genetic Resources Information No. 21, http://www.fao.org/docrep/006/v3030e/V3030E10.htm, 7 pages.

Dong, Y.-H., et al., "Identification of Quorum-Quenching N-acyl Homoserine Lactonases from *Bacillus* Species," Applied and Environmental Microbiology, Apr. 2002, pp. 1754-1759, vol. 68, No. 4.

Dowd, P. E., et al., "The Emerging Roles of Phospholipase C in Plant Growth and Development," Lipid Signaling in Plants, 2010, pp. 23-37, vol. 16.

Duc Ie H., et al., "Bacterial Spores as Vaccine Vehicles," Infection and Immunity, May 2003, pp. 2810-2818, vol. 71, No. 5.

Duc, Ie H., et al., "Immunization Against Anthrax Using Bacillus subtilis Spores Expressing the Anthrax Protective Antigen," Vaccine, Jan. 2007, pp. 346-355, vol. 25, No. 2.

Glick, B. R., "Modulation of Plant Ethylene Levels by the Bacterial Enzyme ACC Deaminase," FEMS Microbiology Letters, 2005, pp. 1-7, vol. 251, No. 1.

Gujar, P. D., et al., "Effect of Phytase from Aspergillus niger on Plant Growth and Mineral Assimilation in Wheat (*Triticum aestivum* Linn.) and its Potential for Use as a Soil Amendment," Journal of the Science of Food and Agriculture, 2013, pp. 2242-2247, vol. 93, No. 9.

Hafeez, F. Y., et al., "PGPR: Versatile Tool to Combat Soil Borne Pathogens and Improve Plant Health," Aspects of Applied Biology, 2011,, pp. 241-245, vol. 106.

Han, W., et al., "The Application of Exogenous Cellulase to Improve Soil Fertility and Plant Growth Due to Acceleration of Straw Decomposition," Bioresource Technology, May 2010, pp. 3724-3731, vol. 101, No. 10.

Hartati, S., et al., "Overexpression of Poplar Cellulase Accelerates Growth and Disturbs the Closing Movements of Leaves in Sengon," Plant Physiology, Jun. 2008, pp. 552-561, vol. 147.

Hoelscher, B., et al., "Removal of Toxic Contaminants from Polluted Soil and Water via Enzyme-Linked Bacillus Spores," Poster presented at Missouri Life Sciences Week Research Poster Session, Apr. 14, 2010.

Hong, Y. et al., "Phospholipases in Plant Response to Nitrogen and Phosphorus Availability," Phospholipases in Plant Signaling, 2013, pp. 159-180, vol. 20.

Howard, G. T., et al., "Effects of Cellulolytic Ruminal Bacteria and of Cell Extracts on Germination of *Euonymus americanus* L. Seeds," Applied and Environmental Microbiology, Jan. 1988, pp. 218-224, vol. 54, No. 1.

Idriss, E. E., et al., "Extracellular Phytase Activity of Bacillus amyloliquefaciens FZB45 Contributes to its Plant-Growth-Promoting Effect," Microbiology, 2002, pp. 2097-2109, vol. 148.

International Search Report and Written Opinion issued for PCT/US2014/030824, dated Aug. 1, 2014, 22 pages.

International Search Report and Written Opinion issued for PCT/US2015/050807, dated Dec. 10, 2015, 12 pages.

Isticato, R., et al., "Surface Display of Recombinant Proteins on Bacillus subtilis Spores," Journal of Bacteriology, Nov. 2001, pp. 6294-6301, vol. 183, No. 21.

Jackson, W. T., "Effect of Pectinase and Cellulase Preparations on the Growth and Development of Root Hairs," Physiologia Plantarum, 2006 (first published in Jul. 1959), pp. 502-510, vol. 12, No. 3.

Johnson M. J., et al., "ExsY and CotY are Required for the Correct Assembly of the Exosporium and Spore Coat of Bacillus cereus," Journal of Bacteriology, 2006, pp. 7905-7913, vol. 188, No. 22.

Kim, J. H., et al., "Bacterial Surface Display of GFP(uv) on Bacillus subtilis Spores," Journal of Microbiology and Biotechnology, Apr. 2007, pp. 677-680, vol. 17, No. 4.

Kim, J. H., et al., "Spore-Displayed Streptavidin: A Live Diagnostic Tool in Biotechnology," Biochemical and Biophysical Research Communications, May 2005, pp. 210-214, vol. 331, No. 1.

Leski, T. A., et al., "Identification and Classification of bcl Genes and Proteins of Bacillus cereus Group Organisms and Their Application in Bacillus anthracis Detection and Fingerprinting," Applied and Environmental Microbiology, Nov. 2009, pp. 7163-7172, vol. 75, No. 22.

Li, W., et al., "Cloning of the Thermostable Cellulase Gene From Newly Isolated Bacillus subtilis and its Expression in *Escherichia coli*," Molecular Biotechnology, 2008, pp. 195-201, vol. 40, No. 2.

Luiz, W. B., et al., "Boosting Systemic and Secreted Antibody Responses in Mice Orally Immunized with Recombinant Bacillus subtilis Strains Following Parenteral Priming with a DNA Vaccine Encoding the Enterotoxigenic *Escherichia coli* (ETEC) CFA/I Fimbriae B Subunit," Vaccine, 2008, pp. 3998-4005, vol. 26, No. 32.

Mauriello, E. M., et al., "Display of Heterologous Antigens on the Bacillus subtilis Spore Coat Using CotC as a Fusion Partner," Vaccine, Mar. 2004, pp. 1177-1187, vol. 22, Nos. 9-10.

Medie, F. M., "Genome Analyses Highlight the Different Biological Roles of Cellulases," Nature Reviews Microbiology, Mar. 2012, pp. 227-234, vol. 10.

Paccez, J. D., et al., "Evaluation of Different Promoter Sequences and Antigen Sorting Signals on the Immunogenicity of Bacillus subtilis Vaccine Vehicles," Vaccine, 2007, pp. 4671-4680, vol. 25, No. 24.

Paccez, J. D., et al., "Stable Episomal Expression System Under Control of a Stress Inducible Promoter Enhances the Immunogenicity of *Bacillus subtilis* as a Vector for Antigen Delivery," Vaccine, 2006, pp. 2935-2943, vol. 24, No. 15.

Park, T. J., et al., "Spore Display Using Bacillus thuringiensis Exosporium Protein InhA," Journal of Microbiology and Biotechnology, May 2009, pp. 495-501, vol. 19, No. 5.

Park, T. J., "Surface-Display of Recombinant Proteins on Bacterial Exosporium and its Biotechnological Applications," Doctoral Thesis presented to the Department of Chemical and Biomolecular Engineering, Korea Advanced Institute of Science and Technology, 2004, 104 pages.

Phitsuwan, P., et al., "Present and Potential Applications of Cellulases in Agriculture, Biotechnology, and Bioenergy," Folia Microbiologica, 2013, pp. 163-176, vol. 58, No. 2.

Pilar-Izquierdo, M. C., et al., "Barley Seed Coating with Free and Immobilized Alkaline Phosphatase to Improve P Uptake and Plant Growth," Journal of Agricultural Science, 2012, pp. 691-701, vol. 150, No. 6.

Ping, R., et al., Journal of Northwest Forestry College, 2005, pp. 78-79, vol. 20, No. 1, Abstract, 1 page.

Sales, J., et al. "Coffee (*Coffea arabica* L.) Seeds Germination After Treatment With Different Concentrations and Embebding Times in Cellulase", Ciencia e Agrotecnologia [online], 2003, pp. 557-564, vol. 27, No. 3, ISSN 1413-7054. http://dx.doi.org/10.1590/S1413-70542003000300009, Abstract, 1 page.

Sequence Listing filed in WO 20071078127 A1 published Jul. 12, 2007, downloaded from <http://patentscope.wipo.int/search/en/detail.jsf?docId=WO2007078127&recNum=1&tab=PCTDocuments&maxRec=&office=&prevFilter=&sortOption=&queryString=>, 5 pages.

(56) References Cited

OTHER PUBLICATIONS

Shani, Z., et al., "Expression of Endo-1,4-beta-glucanase (cel1) in *Arabidopsis thaliana* is Associated with Plant Growth, Xylem Development and Cell Wall Thickening," Plant Cell Reports, Oct. 2006, pp. 1067-1074, vol. 25, No. 10.

Shen, M., et al., "Effect of Plant Growth-Promoting Rhizobacteria (PGPRs) on Plant Growth, Yield, and Quality of Tomato (*Lycopersicon esculentum* Mill.) Under Simulated Seawater Irrigation," The Journal of General and Applied Microbiology, 2012, pp. 253-262, vol. 58, No. 4.

Singh B., et al., "Microbial Phytases in Phosphorus Acquisition and Plant Growth Promotion," Physiology and Molecular Biology of Plants, Apr. 2011, pp. 93-103, vol. 17, No. 2.

Singh B., et al., "Plant Growth Promotion by an Extracellular HAP-Phytase of a Thermophilic Mold Sporotrichum thermophile," Applied Biochemistry and Biotechnology, Mar. 2010, pp. 1267-1276, vol. 160, No. 5.

Smirnova, I., et al., "The Effect of Inoculation by Cellulolytic Bacteria Bacillus cytaseus on Wheat Productivity", Plant Growth-Promoting Rhizobacteria (PGPR) for Sustainable Agriculture, Proceedings of the 2nd Asian PGPR conference, Aug. 21-24, 2011, pp. 185-191.

Stearns, J. C., et al., "Effects of Bacterial ACC Deaminase on Brassica napus Gene Expression," Molecular Plant-Microbe Interactions, 2012, pp. 668-676, vol. 25, No. 5.

Steichen, C. T., et al., "Non-Uniform Assembly of the Bacillus anthracis Exosporium and a Bottle Cap Model for Spore Germination and Outgrowth," Molecular Microbiology, Apr. 2007, pp. 359-367, vol. 64, No. 2.

Tan, L., et al., "An Unusual Mechanism of Isopeptide Bond Formation Attaches the Collagenlike Glycoprotein BclA to the Exosporium of Bacillus anthracis," May-Jun. 2011, 20 pages, vol. 2, No. 3.

Tan, L., et al., "An Unusual Mechanism of Isopeptide Bond Formation Attaches the Collagenlike Glycoprotein BclA to be Exosporium of Bacillus anthracis," May-Jun. 2011, 20 pages, vol. 2, No. 3 (Retraction).

Tan, L., et al., "Sequence Motifs and Proteolytic Cleavage of the Collagen-Like Glycoprotein BclA Required for Its Attachment to the Exosporium of Bacillus anthracis," Journal of Bacteriology, Mar. 2010, pp. 1259-1268, vol. 192, No. 5.

Ahemad, M., et al., "Mechanisms and Applications of Plant Growth Promoting Rhizobacteria: Current Perspective," Journal of King Saud University—Science, 2014, pp. 1-20, vol. 26.

Frankel, A. E., et al., "Characterization of Diphtheria Fusion Proteins Targeted to the Human Interleukin-3 Receptor," Protein Engineering, 2000, pp. 575-581, vol. 13, No. 8.

Pakula, A. A., et al., "Genetic Analysis of Protein Stability and Function," Annual Review of Genetics, 1989, pp. 289-310, vol. 23 (Abstract Only).

Thompson, B. M., "Amino-Terminal Sequences of the Bacillus Anthracis Exosporium Proteins BclA and BclB Important for Localization and Attachment to the Spore Surface," A Thesis presented to the Faculty of the Graduate School at the University of Missouri, Columbia, Aug. 2008, 165 pages.

Thompson, B. M., et al., "Assembly of the BclB Glycoprotein into the Exosporium and Evidence for its Role in the Formation of the Exosporium 'cap' Structure in Bacillus anthracis," Molecular Microbiology, Dec. 2012, pp. 1073-1084, vol. 86, No. 5.

Thompson, B. M., et al., "Localization and Assembly of the Novel Exosporium Protein BetA of Bacillus anthracis," Journal of Bacteriology, 2011, pp. 5098-5104, vol. 193, No. 19.

Thompson, B. M. et al., "A System of Efficient, Cost-Effective, and Customizable Vaccines for Use with Multiple Vaccine Candidates," Oct. 2010 poster presentation, 1 page.

Thompson, B. M., et al., "Targeting of the BclA and BclB Proteins to the Bacillus anthracis Spore Surface," Molecular Microbiology, 2008, pp. 421-434, vol. 70, No. 2.

Thompson, B. M., et al., "The BclB Glycoprotein of Bacillus anthracis is Involved in Exosporium Integrity," Journal of Bacteriology, 2007, pp. 6704-6713, vol. 189, No. 18.

Thompson, B. M., et al., "The Co-Dependence of BxpB/ExsFA and BclA for Proper Incorporation into the Exosporium of Bacillus anthracis," Molecular Microbiology, 2011, pp. 799-813, vol. 79, No. 3.

Thompson, B. M., "The Role of the Glycoprotein BclB in the Exosporium in the Exosporium of Bacillus anthracis," Doctoral Dissertation presented to the Department of Diagnostic Medicine/Pathobiology, College of Veterinary Medicine, Kansas State University, 2002, 178 pages.

Waller, L. N., et al., "Identification of a Second Collagen-Like Glycoprotein Produced by Bacillus anthracis and Demonstration of Associated Spore-Specific Sugars," Journal of Bacteriology, Jul. 2005, pp. 4592-4597, vol. 187, No. 13.

Wang, X., et al., "PLD: Phospholipase Ds in Plant Signaling," Phospholipases in Plant Signaling, Signaling and communication in Plants, 2013, pp. 3-26, vol. 20.

Zhou, Z. et al., "Immunogenicity of Recombinant Bacillus subtilis Spores Expressing Clonorchis sinensis tegumental Protein," Parasitology Research, 2008, pp. 293-297, vol. 102, No. 2.

Zhou, Z., et al., "Oral Administration of a Bacillus subtilis Spore-Based Vaccine Expressing Clonorchis sinensis tegumental Protein 22.3 kDa Confers Protection Against Clonorchis sinensis," Vaccine, 2008, pp. 1817-1825, vol. 26, No. 15.

Preliminary Amendment A and Response to Notification of Insufficiency filed on Jan. 28, 2016, for U.S. Appl. No. 14/775,892, 32 pages.

Restriction Requirement dated Aug. 17, 2016, for U.S. Appl. No. 14/775,892, 8 pages.

Response to Restriction Requirement and Amendment B filed on Oct. 13, 2016, for U.S. Appl. No. 14/775,892, 16 pages.

Restriction Requirement dated Dec. 28, 2016, for U.S. Appl. No. 14/775,892, 5 pages.

Response to Restriction Requirement filed on Feb. 23, 2017, for U.S. Appl. No. 14/775,892, 18 pages.

Non-Final Office Action dated Mar. 22, 2017, for U.S. Appl. No. 14/775,892, 12 pages.

* cited by examiner

| | | | |
|---|---|---|---|
| MSNNNYSNGLNPDESLSAS**AFDPNLVGPTLPPIPP**FTLPTG | SEQ ID NO. 1 | 20-35 %Identity | 25-35 %Identity |
| MSEKYIILHGT**ALEPNLIGPTLPPIPP**FTFPNG | SEQ ID NO. 3 | 81.3% | 90.9% |
| MVKVVEGNGGKSKIKSPLNSNF**KILSDLVGPTFPPVPT**GMTGIT | SEQ ID NO: 5 | 50.0% | 72.7% |
| MKQNDKLWLDKG**IIGPENIGPTFPVLPP**IHIPTG | SEQ ID NO: 7 | 43.8% | 54.5% |
| MDEFLSSA**ALNPGSVGPTLPPMQP**FQFRTG | SEQ ID NO: 9 | 62.5% | 72.7% |
| MFDKNEIQKINGILQAN**ALNPNLIGPTLPPIPP**FTLPTG | SEQ ID NO: 11 | 81.3% | 90.9% |
| MFDKNEMKKTNEVLQAN**ALDPNIIGPTLPPIPP**FTLPTG | SEQ ID NO: 13 | 81.3% | 81.8% |
| MSRKDKFNRSRMSRKDRFNSPKIKSEI**SISPDLVGPTFPPIPS**FTLPTG | SEQ ID NO: 15 | 62.5% | 81.8% |
| MNEEYSILHGP**ALEPNLIGPTLPSIPP**FTFPTG | SEQ ID NO: 17 | 75.0% | 81.8% |
| MKNRDNNRKQNSLSSNF**RIPPELIGPTFPPVPT**GFTGIG | SEQ ID NO: 19 | 50.0% | 63.6% |
| MSDKHQMKKISEVLQAH**ALDPNLIGPPLPPITP**FTFPTG | SEQ ID NO: 21 | 75.0% | 72.7% |
| MDEFLSFA**ALNPGSIGPTLPPVPP**FQFPTG | SEQ ID NO: 23 | 62.5% | 72.7% |
| MDEFLSST**ALNPCSIGPTLPPMQP**FQFPTG | SEQ ID NO: 25 | 56.2% | 63.6% |
| MKERDRQNSLNSNF**RISPNLIGPTFPPVPT**GFTGIG | SEQ ID NO: 27 | 56.2% | 63.6% |
| VFDKNEIQKINGILQAN**ALNPNLIGPTLPPIPP**FTLPTG | SEQ ID NO: 29 | 81.3% | 90.9% |
| MDEFLYFA**ALNPGSIGPTLPPVQP**FQFPTG | SEQ ID NO: 31 | 56.2% | 63.6% |
| **MDSKNIGPTFPPLPS**INFPTG | SEQ ID NO: 33 | 43.8% | 54.5% |
| **MIGPENIGPTFPILPP**IYIPTG | SEQ ID NO: 35 | 43.8% | 54.5% |

FUSION PROTEINS AND METHODS FOR STIMULATING PLANT GROWTH, PROTECTING PLANTS FROM PATHOGENS, AND IMMOBILIZING BACILLUS SPORES ON PLANT ROOTS

CROSS-REFERENCE TO RELATED APPLICATIONS

This application is a divisional of U.S. patent application Ser. No. 14/213,525, filed on Mar. 14, 2014, which claims the benefit of U.S. Provisional Patent Application Ser. No. 61/799,262, filed Mar. 15, 2013. Each of the above-cited applications is incorporated herein by reference in its entirety.

FIELD OF THE INVENTION

The present invention generally relates to fusion proteins containing a targeting sequence that targets the fusion protein to the exosporium of a *Bacillus cereus* family member. The invention also relates to recombinant *Bacillus cereus* family members expressing such fusion proteins, formulations containing the recombinant *Bacillus cereus* family members expressing the fusion proteins, and methods for stimulating plant growth and for protecting plants from pathogens by applying the recombinant *Bacillus cereus* family members or the formulations to plants or a plant growth medium. The invention also relates to methods for immobilizing spores of a recombinant *Bacillus cereus* family member expressing a fusion protein on plant roots.

BACKGROUND OF THE INVENTION

Within the zone surrounding a plant's roots is a region called the rhizosphere. In the rhizosphere, bacteria, fungi, and other organisms compete for nutrients and for binding to the root structures of the plant. Both detrimental and beneficial bacteria and fungi can occupy the rhizosphere. The bacteria, fungi, and the root system of the plant can all be influenced by the actions of peptides, enzymes, and other proteins in the rhizosphere. Augmentation of soil or treatment of plants with certain of these peptides, enzymes, or other proteins would have beneficial effects on the overall populations of beneficial soil bacteria and fungi, create a healthier overall soil environment for plant growth, improve plant growth, and provide for the protection of plants against certain bacterial and fungal pathogens. However, previous attempts to introduce peptides, enzymes, and other proteins into soil to induce such beneficial effects on plants have been hampered by the low survival of enzymes, proteins, and peptides in soil. Additionally, the prevalence of proteases naturally present in the soil leads to degradation of the proteins in the soil. The environment around the roots of a plant (the rhizosphere) is a unique mixture of bacteria, fungi, nutrients, and roots that has different qualities than that of native soil. The symbiotic relationship between these organisms is unique, and could be altered for the better with inclusion of exogenous proteins. The high concentration of fungi and bacteria in the rhizosphere causes even greater degradation of proteins due to abnormally high levels of proteases and other elements detrimental to proteins in the soil. In addition, enzymes and other proteins introduced into soil can dissipate away from plant roots quickly.

Thus, there exists a need in the art for a method for effectively delivering peptides, enzymes, and other proteins to plant root systems and for extending the period of time during which such molecules remain active. Furthermore, there exists a need in the art for a method of selectively targeting such peptides, enzymes, and proteins to the rhizosphere and to plant roots in particular.

SUMMARY OF THE INVENTION

In one aspect, the present invention is directed to a fusion protein comprising at least one plant growth stimulating protein or peptide and a targeting sequence. The plant growth stimulating protein or peptide comprises a peptide hormone, a non-hormone peptide, or an enzyme involved in the production of a plant growth stimulating compound.

In another aspect, the present invention relates to fusion protein comprising at least one protein or peptide that protects a plant from a pathogen and a targeting sequence.

The present invention is also directed to fusion proteins comprising at least one root binding protein or peptide and a targeting sequence.

In any of the fusion proteins, the targeting sequence can be:

(a) a targeting sequence comprising an amino acid sequence having at least about 43% identity with amino acids 20-35 of SEQ ID NO: 1, wherein the identity with amino acids 25-35 is at least about 54%;
(b) a targeting sequence comprising amino acids 1-35 of SEQ ID NO: 1;
(c) a targeting sequence comprising amino acids 20-35 of SEQ ID NO: 1;
(d) a targeting sequence comprising SEQ ID NO: 1;
(e) an amino acid sequence comprising SEQ ID NO: 2;
(f) a targeting sequence comprising amino acids 1-27 of SEQ ID NO: 3;
(g) a targeting sequence comprising amino acids 12-27 of SEQ ID NO: 3;
(h) a targeting sequence comprising SEQ ID NO: 3;
(i) an amino acid sequence comprising SEQ ID NO: 4;
(j) a targeting sequence comprising amino acids 1-38 of SEQ ID NO: 5;
(k) a targeting sequence comprising amino acids 23-38 of SEQ ID NO: 5;
(l) a targeting sequence comprising SEQ ID NO: 5;
(m) an amino acid sequence comprising SEQ ID NO: 6;
(n) a targeting sequence comprising amino acids 1-28 of SEQ ID NO: 7;
(o) a targeting sequence comprising amino acids 13-28 of SEQ ID NO: 7;
(p) a targeting sequence comprising SEQ ID NO: 7;
(q) an amino acid sequence comprising SEQ ID NO: 8;
(r) a targeting sequence comprising amino acids 1-24 of SEQ ID NO: 9;
(s) a targeting sequence comprising amino acids 9-24 of SEQ ID NO: 9;
(t) a targeting sequence comprising SEQ ID NO. 9;
(u) an amino acid sequence comprising SEQ ID NO. 10;
(v) a targeting sequence comprising amino acids 1-33 of SEQ ID NO:11;
(w) a targeting sequence comprising amino acids 18-33 of SEQ ID NO: 11;
(x) a targeting sequence comprising SEQ ID NO: 11;
(y) an amino acid sequence comprising SEQ ID NO: 12;
(z) a targeting sequence comprising amino acids 1-33 of SEQ ID NO: 13;
(aa) a targeting sequence comprising amino acids 18-33 of SEQ ID NO: 13;
(ab) a targeting sequence comprising SEQ ID NO:13;
(ac) a targeting sequence comprising SEQ ID NO:14;

(ad) a targeting sequence comprising amino acids 1-43 of SEQ ID NO: 15;
(ae) a targeting sequence comprising amino acids 28-43 of SEQ ID NO: 15;
(af) a targeting sequence comprising SEQ ID NO:15;
(ag) a targeting sequence comprising SEQ ID NO:16;
(ah) a targeting sequence comprising amino acids 1-27 of SEQ ID NO: 17;
(ai) a targeting sequence comprising amino acids 12-27 of SEQ ID NO: 17;
(aj) a targeting sequence comprising SEQ ID NO:17;
(ak) a targeting sequence comprising SEQ ID NO:18;
(al) a targeting sequence comprising amino acids 1-33 of SEQ ID NO: 19;
(am) a targeting sequence comprising amino acids 18-33 of SEQ ID NO: 19;
(an) a targeting sequence comprising SEQ ID NO:19;
(ao) a targeting sequence comprising SEQ ID NO:20;
(ap) a targeting sequence comprising amino acids 1-33 of SEQ ID NO: 21;
(aq) a targeting sequence comprising amino acids 18-33 of SEQ ID NO: 21;
(ar) a targeting sequence comprising SEQ ID NO:21;
(as) a targeting sequence comprising SEQ ID NO:22;
(at) a targeting sequence comprising amino acids 1-24 of SEQ ID NO: 23;
(au) a targeting sequence comprising amino acids 9-24 of SEQ ID NO: 23;
(av) a targeting sequence comprising SEQ ID NO:23;
(aw) a targeting sequence comprising SEQ ID NO:24;
(ax) a targeting sequence comprising amino acids 1-24 of SEQ ID NO: 25;
(ay) a targeting sequence comprising amino acids 9-24 of SEQ ID NO: 25;
(az) a targeting sequence comprising SEQ ID NO:25;
(ba) a targeting sequence comprising SEQ ID NO:26;
(bb) a targeting sequence comprising amino acids 1-30 of SEQ ID NO: 27;
(bc) a targeting sequence comprising amino acids 15-30 of SEQ ID NO: 27;
(bd) a targeting sequence comprising SEQ ID NO:27;
(be) a targeting sequence comprising SEQ ID NO:28;
(bf) a targeting sequence comprising amino acids 1-33 of SEQ ID NO: 29;
(bg) a targeting sequence comprising amino acids 18-33 of SEQ ID NO: 29;
(bh) a targeting sequence comprising SEQ ID NO:29;
(bi) a targeting sequence comprising SEQ ID NO:30;
(bj) a targeting sequence comprising amino acids 1-24 of SEQ ID NO: 31;
(bk) a targeting sequence comprising amino acids 9-24 of SEQ ID NO: 31;
(bl) a targeting sequence comprising SEQ ID NO:31;
(bm) a targeting sequence comprising SEQ ID NO:32;
(bn) a targeting sequence comprising amino acids 1-15 of SEQ ID NO: 33;
(bo) a targeting sequence comprising SEQ ID NO:33;
(bp) a targeting sequence comprising SEQ ID NO:34;
(bq) a targeting sequence comprising amino acids 1-16 of SEQ ID NO: 35;
(br) a targeting sequence comprising SEQ ID NO:35; or
(bs) a targeting sequence comprising SEQ ID NO:36.

In other aspects, the invention relates to a recombinant *Bacillus cereus* family member that expresses any of the fusion proteins.

In yet other aspects, the invention is directed to formulations comprising any of the recombinant *Bacillus cereus* family members and an agriculturally acceptable carrier.

The present invention also relates to a method for stimulating plant growth. The method comprises introducing into a plant growth medium any of the recombinant *Bacillus cereus* family members expressing a fusion protein comprising at least one plant growth stimulating protein or peptide, or any of the formulations comprising the recombinant *Bacillus cereus* family members expressing a fusion protein comprising at least one plant growth stimulating protein or peptide. Alternatively, the method comprises applying to foliage of a plant, a plant seed, or an area surrounding a plant any of the recombinant *Bacillus cereus* family members expressing a fusion protein comprising at least one plant growth stimulating protein or peptide, or any of the formulations comprising the recombinant *Bacillus cereus* family members expressing a fusion protein comprising at least one plant growth stimulating protein or peptide. The plant growth stimulating protein or peptide is physically attached to the exosporium of the recombinant *Bacillus* family member.

Another aspect of the invention is directed to a method for stimulating plant growth. The method comprises introducing a recombinant *Bacillus cereus* family member expressing a fusion protein into a plant growth medium or applying a recombinant *Bacillus cereus* family member expressing a fusion protein to foliage of a plant, a plant seed, or an area surrounding a plant. The fusion protein comprises at least one plant growth stimulating protein or peptide and a targeting sequence. The targeting sequence can be any of the targeting sequences listed above. The plant growth stimulating protein or peptide is physically attached to the exosporium of the recombinant *Bacillus* family member.

The present invention also relates to a method for protecting a plant from a pathogen. The method comprises introducing into a plant growth medium any of the recombinant *Bacillus cereus* family members expressing a fusion protein comprising at least one protein or peptide that protects a plant from a pathogen, or any of the formulations comprising the recombinant *Bacillus cereus* family members expressing a fusion protein comprising at least one protein or peptide that protects a plant from a pathogen. Alternatively, the method comprises applying to foliage of a plant, a plant seed, or an area surrounding a plant any of the recombinant *Bacillus cereus* family members expressing a fusion protein comprising at least one protein or peptide that protects a plant from a pathogen, or any of the formulations comprising the recombinant *Bacillus cereus* family members expressing a fusion protein comprising at least one protein or peptide that protects a plant from a pathogen. The protein or peptide that protects a plant from a pathogen is physically attached to the exosporium of the recombinant *Bacillus* family member.

The present invention further relates to a method for immobilizing a recombinant *Bacillus cereus* family member spore on a root system of a plant. The method comprises introducing into a plant growth medium any of the recombinant *Bacillus cereus* family members expressing a fusion protein comprising at least one root binding protein or peptide, or any of the formulations comprising the recombinant *Bacillus cereus* family members expressing a fusion protein comprising at least one root binding protein or peptide. Alternatively, the method comprises applying to foliage of a plant, a plant seed, or an area surrounding a plant any of the recombinant *Bacillus cereus* family members expressing a fusion protein comprising at least one root binding protein or peptide, or any of the formulations comprising the recombinant *Bacillus cereus* family members expressing a fusion protein comprising at least one root binding protein or peptide. The root binding protein or peptide is physically attached to the exosporium of the recombinant *Bacillus cereus* family member.

Other objects and features will be in part apparent and in part pointed out hereinafter.

BRIEF DESCRIPTION OF THE DRAWING

FIG. 1 shows an alignment of the amino acid sequence of the amino-terminal portion of *Bacillus anthracis* Sterne strain BclA and with the corresponding region from various exosporium proteins from *Bacillus cereus* family members.

DEFINITIONS

When the articles "a," "an," "one," "the," and "said" are used herein, the mean "at least one" or "one or more" unless otherwise indicated.

The terms "comprising," "including," and "having" are intended to be inclusive and mean that there may be additional elements other than the listed elements.

The term "bioactive peptide" refers to any peptide refers to any peptide that exerts a biological activity. "Bioactive peptides" can be generated, for example, via the cleavage of a protein or peptide by a protease or peptidase.

An "enzyme involved in the production of a plant growth stimulating compound" includes any enzyme that catalyzes any step in a biological synthesis pathway for a compound that stimulates plant growth. Such compounds include, for example, but are not limited to, small molecule plant hormones such as auxins and cytokinins, bioactive peptides, and small plant growth stimulating molecules synthesized by bacteria or fungi in the rhizosphere (e.g., 2,3-butanediol).

The term "fusion protein" as used herein refers to a protein having a polypeptide sequence that comprises sequences derived from two or more separate proteins. A fusion protein can be generated by joining together a nucleic acid molecule that encodes all or part of a first polypeptide with a nucleic acid molecule that encodes all or part of a second polypeptide to create a nucleic acid sequence which, when expressed, yields a single polypeptide having functional properties derived from each of the original proteins.

The term "immobilizing a recombinant *Bacillus cereus* family member spore on a root system" refers to the binding of a *Bacillus cereus* family member spore to a root of a plant, such that the spore is maintained at the plant's root structure instead of dissipating into the plant growth medium.

A "plant growth medium" includes any material that is capable of supporting the growth of a plant.

A "plant immune system enhancer protein or peptide" as used herein includes any protein or peptide that has a beneficial effect on the immune system of a plant.

The term "plant growth stimulating protein or peptide" as used herein includes any protein or peptide that increases plant growth in a plant exposed to the protein or peptide.

A "protein or peptide that protects a plant from a pathogen" as used herein includes any protein or peptide that makes a plant exposed to the protein or peptide less susceptible to infection with a pathogen.

The term "root binding protein or peptide" refers to any peptide or protein capable of specifically or non-specifically binding to a plant root.

The term "targeting sequence" as used herein refers to a polypeptide sequence that, when present as part of longer polypeptide or a protein, results in the localization of the longer polypeptide or a protein to a specific subcellular location. The targeting sequences described herein result in localization of proteins to the exosporium of a *Bacillus cereus* family member.

DESCRIPTION OF THE INVENTION

The present invention relates to fusion proteins containing a targeting sequence that targets the fusion protein to the exosporium of a *Bacillus cereus* family member and: (a) at least one plant growth stimulating protein or peptide; (b) at least one protein or peptide that protects a plant from a pathogen; or (c) at least one root binding protein or peptide. When expressed in *Bacillus cereus* family member bacteria, these fusion proteins are targeted to the exosporium layer of the spore and are physically oriented such that the protein or peptide is displayed on the outside of the spore.

This *Bacillus* exosporium display (BEMD) system can be used to deliver peptides, enzymes, and other proteins to plants (e.g., to plant foliage or plant roots) or to a plant growth medium such as soil. Peptides, enzymes, and proteins delivered to the soil or another plant growth medium in this manner persist and exhibit activity in the soil for extended periods of time. Introduction of recombinant *Bacillus cereus* family member bacteria expressing the fusion proteins described herein into soil or the rhizosphere of a plant leads to a beneficial enhancement of plant growth in many different soil conditions. The use of the BEMD to create these enzymes allows them to continue to exert their beneficial results to the plant and the rhizosphere over the first years of a plants life.

Targeting Sequences

For ease of reference, the SEQ ID NOs. for the peptide and protein sequences referred to herein are listed in Table 1 below.

TABLE 1

Peptide and Protein Sequences

| Protein or targeting sequence (SEQ ID. NO) | Sequence |
|---|---|
| AA 1-41 of BclA (*B. anthracis* Sterne) (SEQ ID NO: 1) | MSNNNYSNGLNPDESLSASAFDPNL VGPTLPPIPPFTLPTG |
| Full length BclA (SEQ ID NO: 2) | MSNNNYSNGLNPDESLSASAFDPNL VGPTLPPIPPFTLPTGPTGPFTTGP TGPTGPTGPTGPTGPTGPTGPTGDT GTTGPTGPTGPTGPTGPTGPTGPTG PTGPTGFTPTGPTGPTGPTGDTGTT GPTGPTGPTGPTGPTGDTGTTGPTG PTGPTGPTGPTGPTGPTFTGPTGPT GPTGATGLTGPTGPTGPSGLGLPAG LYAFNSGGISLDLGINDPVPFNTVG SQFFTGTAISQLDADTFVISETGFY KITVIANTATASVLGGLTIQVNGVP VPGTGSSLISLGAPFTIVIQAITQI TTTPSLVEVIVTGLGLSLALGTSAS IIIEKVA |
| AA 1-33 of BetA/BAS3290 (*B. anthracis* Sterne) (SEQ ID NO: 3) | MSEKYIILHGTALEPNLIGPTLPPI PPFTFPNG |
| Full length BetA/BAS3290 (SEQ ID NO: 4) | MSEKYIILHGTALEPNLIGPTLPPI PPFTFPNGPTGITGPTGATGFTGIG ITGPTGVTGPTGIGITGPTGATGLG ILPVFGTITTDVGIGFSVIVNTNIN |

TABLE 1-continued

| Peptide and Protein Sequences | |
|---|---|
| Protein or targeting sequence (SEQ ID. NO) | Sequence |
| | FTLPGPVSGTTLNPVDNSIIINTTG VYSVSFSIVFVIQAISSSILNLTIN DSIQFAIESRIGGGPGVRATSARTD LLSLNQGDVLRVRIREATGDIIYSN ASLVVSKVD |
| Met + AA 2-43 of BAS4623 (*B. anthracis* Sterne) (SEQ ID NO: 5) | MVKVVEGNGGKSKIKSPLNSNFKIL SDLVGPTFPPVPTGMTGIT |
| Full length BAS4623 (SEQ ID NO: 6) | VVKVVEGNGGKSKIKSPLNSNFKIL SDLVGPTFPPVPTGMTGITGSTGAT GNTGPTGETGATGSAGITGSTGPTG NTGGTGSTGPTGNTGATGSTGVTGS TGVTGSTGVTGSTGVTGSTGPTGET GGTGSTGVTGSTGATGSTGVTGNTG PTGSTGATGNTGSIGETGGTGSMGP TGETGVTGSTGGTGSTGVTGNTGPT GSTGVTGSTGVTGSTGPTGSTGVTG STGPTGSTGVTGSTGVTGNMGPTGS TGVTGNTGSTGTTGATGETGPMGST GATGTTGPTGETGETGETGGTGSTG PTGNTGATGSTGVTGSTGVTGSTGV TGETGPTGSTGATGNTGPTGETGGT GSTGATGSTGVTGNTGPTGSTGVTG NTGATGETGPTGNTGATGNTGPTGE TGVTGSTGPTGETGVTGSTGPTGNT GATGETGATGSTGVTGNTGSTGETG PTGSTGPTGSTGATGVTGNTGPTGS TGATGATGSTGPTGSTGTTGNTGVT GDTGPTGATGVSTTATYAFANNTSG SVISVLLGGTNIPLPNNQNIGPGIT VSGGNTVFTVANAGNYYIAYTINLT AGLLVSSRITVNGSPLAGTINSPTV ATGSFSATIIASLPAGAAVSLQLFG VVALATLSTATPGATLTIIRLS |
| AA 1-34 of BclB (*B. anthracis* Sterne) (SEQ ID NO: 7) | MKQNDKLWLDKGIIGPENIGPTFPV LPPIHIPTG |
| Full length BclB (SEQ ID NO: 8) | MKQNDKLWLDKGIIGPENIGPTFPV LPPIHIPTGITGATGATGITGATGP TGTTGATGATGITGVTGATGITGVT GATGITGVTGATGITGVTGPTGITG ATGPTGITGATGPAGITGVTGPTGI TGATGPTGTTGVTGPTGDTGLAGAT GPTGATGLAGATGPTGDTGATGPTG ATGLAGATGPTGATGLTGATGATGA TGGGAIIPFASGTTPALLVNAVLAN TGTLLGFGFSQPGIAPGVGGTLTIL PGVVGDYAFVAPRDGIITSLAGFFS ATAALAPLTPVQIQMQIFIAPAASN TFTPVAPPLLLTPALPAIAIGTTAT GIQAYNVPVVAGDKILVYVSLTGAS PIAAVAGFVSAGLNIV |
| AA 1-30 of BAS1882 (*B. anthracis* Sterne) (SEQ ID NO: 9) | MDEFLSSAALNPGSVGPTLPPMQPF QFRTG |
| Full length BAS1882 (SEQ ID NO: 10) | MDEFLSSAALNPGSVGPTLPPMQPF QFRTGPTGSTGAKGAIGNTEPYWHT GPPGIVLLTYDFKSLIISFAFRILP IS |
| AA 1-39 of gene 2280 (*B. weihenstephensis* KBAB4) (SEQ ID NO: 11) | MFDKNEIQKINGILQANALNPNLIG PTLPPIPPFTLPTG |

TABLE 1-continued

| Peptide and Protein Sequences | |
|---|---|
| Protein or targeting sequence (SEQ ID. NO) | Sequence |
| Full length KBAB4 gene 2280 (SEQ ID NO: 12) | MFDKNEIQKINGILQANALNPNLIG PTLPPIPPFTLPTGPTGVTGPTGVT GPTGVTGPTGVTGPTGVTGPTGVTG PTGVTGPTGVTGPTGVTGPTGVTGP TGVTGPTGVTGPTGVTGPTGVTGPT GETGPTGGTEGCLCDCCVLPMQSVL QQLIGETVILGTIADTPNTPPLFFL FTITSVNDFLVTVTDGTTTFVVNIS DVTGVGFLPPGPPITLLPPTDVGCE CECRERPIRQLLDAFIGSTVSLLAS NGSIAADFSVEQTGLGIVLGTLPIN PTTTVRFAISTCKITAVNITPITM |
| AA 1-39 of gene 3572 (*B. weihenstephensis* KBAB4) (SEQ ID NO: 13) | MFDKNEMKKTNEVLQANALDPNIIG PTLPPIPPFTLPTG |
| Full Length KBAB4 gene 3572 (SEQ ID NO: 14) | MFDKNEMKKTNEVLQANALDPNIIG PTLPPIPPFTLPTGPTGPTGPTGPT GPTGPTGPTGPTGPTGPTGPTGPTG PTGLTGPTGPTGLTGPTGLTGPTGP TGLTGQTGSTGPTGATEGCLCDCCV FPMQEVLRQLVGQTVILATIADAPN VAPRFFLFNITSVNDFLVTVTDPVS NTTFVVNISDVIGVGFSLTVPPLTL LPPADLGCECDCRERPIRELLDTLI GSTVNLLVSNGSIATGFNVEQTALG IVIGTLPIPINPPPPTLFRFAISTC KITAVDITPTPTAT |
| AA 1-49 of Exosporium Leader Peptide (*B. cereus* VD200) (SEQ ID NO: 15) | MSRKDKFNRSRMSRKDRFNSPKIKS EISISPDLVGPTFPPIPSFTLPTG |
| Full Length Exosporium Leader Peptide (SEQ ID NO: 16) | MSRKDKFNRSRMSRKDRFNSPKIKS EISISPDLVGPTFPPIPSFTLPTGI TGPTFNINFRAEKNVAQSFTPPADI QVSYGNIIFNNGGGYSSVTNTFTAP INGIYLFSASIGFNPTLGTTSTLRI TIRKNLVSVASQTGTITTGGTPQLE ITTIIDLLASQTIDIQFSAAESGTL TVGSSNFFSGALLP |
| AA 1-33 of Exosporium Leader Peptide (*B. cereus* VD166) (SEQ ID NO: 17) | MNEEYSILHGPALEPNLIGPTLPSI PPFTFPTG |
| Full Length Exosporium Leader Peptide (SEQ ID NO: 18) | MNEEYSILHGPALEPNLIGPTLPSI PPFTFPTGPTGITGPTGATGFTGIG ITGPTGVTGPTGIGITGPTGATGPT GIGITGPTG |
| AA 1-39 of hypothetical protein IKG_04663 (*B. cereus* VD200) (SEQ ID NO: 19) | MKNRDNNRKQNSLSSNFRIPPELIG PTFPPVPTGFTGIG |
| Full Length hypothetical protein IKG_04663, partial (SEQ ID NO: 20) | MKNRDNNRKQNSLSSNFRIPPELIG PTFPPVPTGFTGIGITGPTGPQGPT GPQGPRGLQGPMGEMGPTGPQGVQG IQGSVGPIGATGPEGQQGPQGLRGP QGETGATGPGGVQGLQGPIGPTGAT GAQGIQGIQGLQGPIGATGPEGSQG IQGVQGLPGATGPQGIQGAQGIQGT PGPSGNTGATGATGATGQGITGPTG ITGPTGITGPSGGPPGPTGPTGATG PGGGPSGSTGATGATGNTGATGSTG |

TABLE 1-continued

| Peptide and Protein Sequences | |
|---|---|
| Protein or targeting sequence (SEQ ID. NO) | Sequence |
| | VTGATGSTGPTGSTGAQGLQGIQGI<br>QGPIGPTGPEGSQGIQGIPGPTGVT<br>GEQGIQGVQGIQGATGATGDQGPQG<br>IQGVIGPQGVTGATGDQGPQGIQGV<br>PGPSGETGPQGVQGIQGPMGDIGPT<br>GPEGPEGLQGPQGIQGVPGPVGATG<br>PEGPQGIQGIQGPVGATGPQGPQGI<br>QGIQGVQGITGATGVQGATGIQGIQ<br>GEIGATGPEGPQGVQGAQGAIGPTG<br>PMGPQGVQGVQGIQGATGAQGVQGP<br>QGIQGIQGPTGATGDMGATGATGEG<br>TTGPTGVTGPTGVTGPSGGPAGPTG<br>PTGPSGPAGVTGPSGGPPGPTGATG<br>ATGVTGDTGATGSTGVTGATGETGA<br>TGVTGLQGPQGIQGVQGEIGPTGPQ<br>GVQGPQGIQGVTGATGDQGPQGIQG<br>PQGDIGPTGPQGIQGPQGSQGIQGA<br>TGGTGAQGPQGIQGPQGDIGLTGSQ<br>GPTGIQGIQGEIGPTGPEGPEGLQG<br>PQGIQGIQGPVGATGPEGPQGIQGI<br>QGVQGATGPQGPQGIQGIQGVQGIT<br>GATGAQGATGIQGIQGEIGATGPEG<br>PQGVQGIQGAIGPTGPMGAQGVQGI<br>QGIQGATGAQGVQGPQGIQGVQGPT<br>GATGETGATGATGEGTTGPTGVTGP<br>TGVTGPSGGPAGPTGPTGPSGPAGV<br>TGPSGGPPGPTGATGATGVTGDTGA<br>TGSTGVTGATGATGATGVTGLQGPQ<br>GIQGVQGEIGPTGPQGIQGPQGIQG<br>VTGATGAQGPQGIQGPQGDIGPTGS<br>QGIQGPQGPQGIQGATGATGAQGPQ<br>GIQGPQGEIGPTGPQGPQGIQGPQG<br>IQGPTG |
| AA 1-39 of YVTN β-propeller protein (*B. weihenstephensis* KBAB4) (SEQ ID NO: 21) | MSDKHQMKKISEVLQAHALDPNLIG<br>PPLPPITPFTFPTG |
| Full length YVTN β-propeller protein KBAB4 (SEQ ID NO: 22) | MSDKHQMKKISEVLQAHALDPNLIG<br>PPLPPITPFTFPTGSTGPTGSTGST<br>GPTGSTGNTGPTGPTGPPVGTNLDT<br>IYVTNDISNNVSAIDGNTNTVLTTI<br>PVGTNPVGVGVNSSTNLIYVVNNGS<br>DNISVINGSTNTVVATIPVGTQPFG<br>VGVNPSTNLIYVANRTSNNVSVIKG<br>GTNTVLTTIPVGTNPVGVGVNSSTN<br>LIYVTNEIPNSVSVIKGGTNTVVAT<br>IPVGLFPFGVGVNSLTNLIYVVNNS<br>PHNVSVIDGNTNTVLTTISVGTSPV<br>GVGVNLSTNLIYVANEVPNNISVIN<br>GNTNTVLTTIPVGTTPFEVGVNSST<br>NLIYVSNLNSNNVSVINGSANTVIA<br>TVPVGSVPRGIGVKP |
| AA 1-30 of hypothetical protein bcerkbab4_2363 (*B. weihenstephensis* KBAB4) (SEQ ID NO: 23) | MDEFLSFAALNPGSIGPTLPPVPPF<br>QFPTG |
| Full length hypothetical protein bcerkbab4_2363 KBAB4 (SEQ ID NO: 24) | MDEFLSFAALNPGSIGPTLPPVPPF<br>QFPTGPTGSTGSTGPTGSTGSTGPT<br>GFNLPAGPASITLTSNETTACVSTQ<br>GNNTLFFSGQVLVNGSPTPGVVVSF<br>SFSNPSLAFMVPLAVITNASGNFTA<br>VFLAANGPGTVTVTASLLDSPGTMA<br>SVTITIVNCP |
| AA 1-30 of hypothetical protein bcerkbab4_2131 (*B. weihenstephensis* KBAB4) (SEQ ID NO: 25) | MDEFLSSTALNPCSIGPTLPPMQPF<br>QFPTG |
| Full length hypothetical protein bcerkbab4_2131 (SEQ ID NO: 26) | MDEFLSSTALNPCSIGPTLPPMQPF<br>QFPTGPTGSTGTTGPTGSIGPTGNT<br>GLTGNTGPTGITGPTGDTG |
| AA 1-36 of triple helix repeat containing collagen (*B. weihenstephensis* KBAB4) (SEQ ID NO: 27) | MKERDRQNSLNSNFRISPNLIGPTF<br>PPVPTGFTGIG |
| Full length triple helix repeat-containing collagen KBAB4 (SEQ ID NO: 28) | MKERDRQNSLNSNFRISPNLIGPTF<br>PPVPTGFTGIGITGPTGPQGPTGPQ<br>GPRGFQGPMGEMGPTGPQGVQGIQG<br>PAGQMGATGPEGQQGPQGLRGPQGE<br>TGATGPQGVQGLQGPIGPTGATGAQ<br>GIQGIQGLQGPIGATGPEGPQGIQG<br>VQGVPGATGSQGIQGAQGIQGPQGP<br>SGNTGATGVTGQGISGPTGITGPTG<br>ITGPSGGPPGPTGATGATGPGGGPS<br>GSTGATGATGNTGVTGSAGVTGNTG<br>STGSTGETGAQGLQGIQGVQGPIGP<br>TGPEGPQGIQGIPGPTGVTGEQGIQ<br>GVQGIQGITGATGDQGPQGIQGAIG<br>PQGITGATGDQGPQGIQGVPGPTGD<br>TGSQGVQGIQGPMGDIGPTGPEGPE<br>GLQGPQGIQGVPGPAGATGPEGPQG<br>IQGIQGPIGVTGPEGPQGIQGIQGI<br>QGITGATGAQGATGVQGVQGNIGAT<br>GPEGPQGVQGTQGDIGPTGPMGPQG<br>VQGIQGIQGPTGAQGVQGPQGIQGI<br>QGPTGVTGDTGTTGATGEGTTGATG<br>VTGPSGVTGPSGGPAGPTGPTGPSG<br>PTGLTGPSGGPPGPTGATGVTGGVG<br>DTGATGSTGVTGATGVTGATGATGL<br>QGPQGIQGVQGDIGPTGPQGVQGPQ<br>GIQGITGATGDQGPQGIQGPQGIQG<br>PTGPQGIQGGQGPQGIQGATGATGA<br>QGPQGIQGIQGVQGPTGPQGPTGIQ<br>GVQGEIGPTGPQGVQGLQGPQGPTG<br>DTGPTGPQGPQGIQGPTGATGATGS<br>QGIQGPTGATGATGSQGIQGPTGAT<br>GATGATGATGATGATGATGVTGVST<br>TATYSFANNTSGSAISVLLGGTNIP<br>LPNNQNIGPGITVSGGNTVFTVTNA<br>GNYYIAYTINITAALLVSSRITVNG<br>SPLAGTINSPAVATGSFNATIISNL<br>AAGSAISLQLFGLLAVATLSTTTPG<br>ATLTIIRLS |
| AA 1-39 of hypothetical protein bmyco0001_21660 (*B. mycoides* 2048) (SEQ ID NO: 29) | VFDKNEIQKINGILQANALNPNLIG<br>PTLPPIPPFTLPTG |
| Full length hypothetical protein bmyco0001_21660 (SEQ ID NO: 30) | VFDKNEIQKINGILQANALNPNLIG<br>PTLPPIPPFTLPTGPTGGTGPTGVT<br>GPTGVTGPTGVTGPTGVTGPTGVTG<br>PTGVTGPTGVTGPTGVTGPTGVTGP<br>TGVTGPTGVTGPTGVTGPTGGTEGC<br>LCDCCVLPMQSVLQQLIGETVILGT<br>IADTPNTPPLFFLFTITSVNDFLVT<br>VTDGTTTFVVNISDVTGVGFLPPGP<br>PITLLPPTDVGCECECRERPIRQLL<br>DAFIGSTVSLLASNGSIAADFSVEQ<br>TGLGIVLGTLPINPTTTVRFAISTC<br>KITAVNITPITM |

TABLE 1-continued

Peptide and Protein Sequences

| Protein or targeting sequence (SEQ ID. NO) | Sequence |
|---|---|
| AA 1-30 of hypothetical protein bmyc0001_22540 (*B. mycoides* 2048) (SEQ ID NO: 31) | MDEFLYFAALNPGSIGPTLPPVQPF QFPTG |
| Full length hypothetical protein bmyc0001_22540 (SEQ ID NO: 32) | MDEFLYFAALNPGSIGPTLPPVQPF QFPTGPTGSTGATGSTGSTGSTGPT GSTGSTGSTGSTGPTGPTGPTGSTG PTGPTGFNLPAGPASITLTSNETTA CVSTQGNNTLFFSGQVLVNGSPTPG VVVSFSFSNPSLAFMVPLAVITNAS GNFTAVFLAANGPGTVTVTASLLDS PGTMASVTITIVNCP |
| AA 1-21 of hypothetical protein bmyc0001_21510 (*B. mycoides* 2048) (SEQ ID NO: 33) | MDSKNIGPTFPPLPSINFPTG |
| Full length hypothetical protein bmyc0001_21510 (SEQ ID NO: 34) | MDSKNIGPTFPPLPSINFPTGVTGE TGATGETGATGATGETGATGETGET GATGATGATGATGETGATGATGATG AAGATGETGATGETGATGETGATGE TGATGVTGETGATGETGAAGETGIT GVTGPTGETGATGETGATGATGITG ATGITGVAGATGETGAAGETGPTGA TGAIGAIGATGATGITGVTGATGET GAAGATGITGVTGATGETGAAGATG ITGATGITGVAGATGITGPTGIPGT IPTTNLLYFTFSDGEKLIYTNADGI AQYGTTQILSPSEVSYINLFINGIL QPQPFYEVTAGQLTLLDDEPPSQGS SIILQFIIIN |
| AA 1-22 of collagen triple helix repeat protein (*B. thuringiensis* 35646) (SEQ ID NO: 35) | MIGPENIGPTFPILPPIYIPTG |
| Full length collagen triple helix repeat protein (SEQ ID NO: 36) | MIGPENIGPTFPILPPIYIPTGETG PTGITGATGETGPTGITGPTGITGA TGETGSTGITGATGETGSTGITGPI GITGATGETGPIGITGATGETGPTG ITGSTGITGLTGVTGLTGETGPIGI TGPTGITGPTGVTGATGPTGGIGPI TTTNLLYYTFADGEKLIYTDTDGIP QYGTTNILSPSEVSYINLFVNGILQ PQPLYEVSTGKLTLLDTQPPSQGSS IILQFIIIN |

AA = amino acids

*Bacillus* is a genus of rod-shaped bacteria. The *Bacillus cereus* family of bacteria includes the species *Bacillus anthracis, Bacillus cereus, Bacillus thuringiensis, Bacillus mycoides, Bacillus pseudomycoides*, and *Bacillus weihenstephensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein BclA, while the basal layer is comprised of a number of different proteins. Another collagen-related protein, BclB, is also present in the exosporium and exposed on endospores of *Bacillus cereus* family members. BclA, the major constituent of the surface nap, has been shown to be attached to the exosporium with its amino-terminus (N-terminus) positioned at the basal layer and its carboxy-terminus (C-terminus) extending outward from the spore.

It was previously discovered that certain sequences from the N-terminal regions of BclA and BclB could be used to target a peptide or protein to the exosporium of a *Bacillus cereus* endospore (see U.S. Patent Application Nos. 2010/0233124 and 2011/0281316, and Thompson et al., Targeting of the BclA and BclB proteins to the *Bacillus anthracis* spore surface, Molecular Microbiology 70(2):421-34 (2008), the entirety of each of which is hereby incorporated by reference). It was also found that the BetA/BAS3290 protein of *Bacillus anthracis* localized to the exosporium.

In particular, amino acids 20-35 of BclA from *Bacillus anthracis* Sterne strain have been found to be sufficient for targeting to the exosporium. A sequence alignment of amino acids 1-41 of BclA (SEQ ID NO: 1) with the corresponding N-terminal regions of several other *Bacillus cereus* family exosporium proteins and *Bacillus cereus* family proteins having related sequences is shown in FIG. 1. The conserved targeting sequence region of BclA (amino acids 20-35 of SEQ ID NO: 1) is shown in bold, and a more highly conserved region spanning amino acids 25-35 within the targeting sequence is underlined. SEQ ID NOs. 3, 5, and 7 in FIG. 1 are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1, each of these sequences contains a conserved region corresponding to amino acids 20-35 of BclA (SEQ ID NO: 1; shown in bold), and a more highly conserved region corresponding to amino acids 20-35 of BclA (underlined).

Additional proteins from *Bacillus cereus* family members also contain the conserved targeting region. In particular, in FIG. 1, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG_04663, SEQ ID NO: 21 is amino acids 1-39 of *Bacillus weihenstephensis* KBAB4 YVTN θ-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, and SEQ ID NO: 35 is amino acids 1-22 of *Bacillus thuringiensis* 35646 collagen triple helix repeat protein. As shown in FIG. 1, each of the N-terminal regions of these proteins contains a region that is conserved with amino acids 20-35 of BclA (SEQ ID NO: 1), and a more highly conserved region corresponding to amino acids 25-35 of BclA.

In the fusion proteins of the present invention, any portion of BclA which includes amino acids 20-35, including full length BclA, can be used as the targeting sequence in the present invention.

Alternatively, any portion of BetA/BAS3290, BAS4623, BclB, BAS1882, the KBAB4 2280 gene product, the KBAB4 3572 gene product, *B. cereus* VD200 exosporium leader peptide, *B. cereus* VD166 exosporium leader peptide, *B. cereus* VD200 hypothetical protein IKG_04663, *B. weihenstephensis* KBAB4 YVTN β-propeller protein, *B. weihenstephensis* KBAB4 hypothetical protein bcerkbab4_2363, *B. weihenstephensis* KBAB4 hypothetical protein bcerkbab4_2131, *B. weihenstephensis* KBAB4 triple helix repeat containing collagen, *B. mycoides* 2048 hypothetical protein bmyco0001_21660, *B. mycoides* 2048 hypothetical protein bmyc0001_22540, *B. mycoides* 2048 hypothetical protein bmyc0001_21510, or *B. thuringiensis* 35646 collagen triple helix repeat protein which includes the amino acids corresponding to amino acids 20-35 of BclA can serve as the targeting sequence. As can be seen from FIG. 1, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of *B. cereus* VD200 exosporium leader peptide, amino acids 12-27 of *B. cereus* VD166 exosporium leader peptide, amino acids 18-33 of *B. cereus* VD200 hypothetical protein IKG_04663, amino acids 18-33 *B. weihenstephensis* KBAB4 YVTN β-propeller protein, amino acids 9-24 of *B. weihenstephensis* KBAB4 hypothetical protein bcerkbab4_2363, amino acids 9-24 of *B. weihenstephensis* KBAB4 hypothetical protein bcerkbab4_2131, amino acids 15-30 of *B. weihenstephensis* KBAB4 triple helix repeat containing collagen, amino acids 18-33 of *B. mycoides* 2048 hypothetical protein bmyco0001_21660, amino acids 9-24 of *B. mycoides* 2048 hypothetical protein bmyc0001_22540, amino acids 1-15 of *B. mycoides* 2048 hypothetical protein bmyc0001_21510, and amino acids 1-16 of *B. thuringiensis* 35646 collagen triple helix repeat protein correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids can serve as the targeting sequence.

Thus, the targeting sequence can comprise amino acids 1-35 of SEQ ID NO: 1, amino acids 20-35 of SEQ ID NO: 1, or SEQ ID NO: 1. Alternatively, the targeting sequence consists of amino acids 1-35 of SEQ ID NO: 1, amino acids 20-35 of SEQ ID NO: 1, or SEQ ID NO: 1. Alternatively, the targeting sequence can comprise full length BclA (SEQ ID NO: 2).

The targeting sequence can also comprise amino acids 1-27 of SEQ ID NO: 3, amino acids 12-27 of SEQ ID NO: 3, SEQ ID NO: 3, or full length BetA/BAS3290 (SEQ ID NO: 4).

The targeting sequence can also comprise amino acids 1-38 of SEQ ID NO: 5, amino acids 23-38 of SEQ ID NO: 5, SEQ ID NO: 5, or full length BAS4623 (SEQ ID NO: 6).

Alternatively, the targeting sequence can comprise amino acids 1-28 of SEQ ID NO: 7, amino acids 13-28 of SEQ ID NO: 7, SEQ ID NO: 7, or full length BclB (SEQ ID NO:8).

The targeting sequence can also comprise amino acids 1-24 of SEQ ID NO: 9, amino acids 9-24 of SEQ ID NO: 9, SEQ ID NO. 9, or full length BAS1882 (SEQ ID NO. 10).

The targeting sequence can also comprise amino acids 1-33 of SEQ ID NO:11, amino acids 18-33 of SEQ ID NO: 11, SEQ ID NO: 11, or the full length KBAB4 2280 gene product (SEQ ID NO: 12).

The targeting sequence can also comprise amino acids 1-33 of SEQ ID NO: 13, amino acids 18-33 of SEQ ID NO: 13, SEQ ID NO:13, or the full length KBAB4_3572 gene product (SEQ ID NO:14).

Alternatively, the targeting sequence can comprise amino acids 1-43 of SEQ ID NO: 15, amino acids 28-43 of SEQ ID NO: 15, SEQ ID NO:15, or full length *B. cereus* VD200 exosporium leader peptide (SEQ ID NO:16).

The targeting sequence can also comprise amino acids 1-27 of SEQ ID NO: 17, amino acids 12-27 of SEQ ID NO: 17, SEQ ID NO:17, or full-length *B. cereus* VD166 exosporium leader peptide (SEQ ID NO:18).

The targeting sequence can also comprise amino acids 1-33 of SEQ ID NO: 19, amino acids 18-33 of SEQ ID NO: 19, SEQ ID NO:19, or full length *B. cereus* VD200 hypothetical protein IKG_04663 (SEQ ID NO:20).

Alternatively, the targeting sequence comprises amino acids 1-33 of SEQ ID NO: 21, amino acids 18-33 of SEQ ID NO: 21, SEQ ID NO:21, or full length *B. weihenstephensis* KBAB4 YVTN β-propeller protein (SEQ ID NO:22).

The targeting sequence can also comprise amino acids 1-24 of SEQ ID NO: 23, amino acids 9-24 of SEQ ID NO: 23, SEQ ID NO:23, or full length *B. weihenstephensis* KBAB4 hypothetical protein bcerkbab4_2363 (SEQ ID NO:24).

The targeting sequence comprise amino acids 1-24 of SEQ ID NO: 25, amino acids 9-24 of SEQ ID NO: 25, SEQ ID NO:25, or full length *B. weihenstephensis* KBAB4 hypothetical protein bcerkbab4_2131 (SEQ ID NO:26).

Alternatively, the targeting sequence comprises amino acids 1-30 of SEQ ID NO: 27, amino acids 15-30 of SEQ ID NO: 27, SEQ ID NO:27, or full length *B. weihenstephensis* KBAB4 triple helix repeat containing collagen (SEQ ID NO:28).

The targeting sequence can also comprise amino acids 1-33 of SEQ ID NO: 29, amino acids 18-33 of SEQ ID NO: 29, SEQ ID NO:29, or full length *B. mycoides* 2048 hypothetical protein bmyco0001_21660 (SEQ ID NO:30).

The targeting sequence can also comprise amino acids 1-24 of SEQ ID NO: 31, amino acids 9-24 of SEQ ID NO: 31, SEQ ID NO:31, or full length *B. mycoides* 2048 hypothetical protein bmyc0001_22540 (SEQ ID NO:32).

Alternatively, the targeting sequence comprises amino acids 1-15 of SEQ ID NO: 33, SEQ ID NO:33, or full length *B. mycoides* 2048 hypothetical protein bmyc0001_21510 (SEQ ID NO:34).

The targeting sequence can also comprise amino acids 1-16 of SEQ ID NO: 35, SEQ ID NO:35, or full length *B. thuringiensis* 35646 collagen triple helix repeat protein (SEQ ID NO:36).

In addition, it can readily be seen from the sequence alignment in FIG. 1 that while amino acids 20-35 of BclA are conserved, and amino acids 25-35 are more conserved, some degree of variation can occur in this region without affecting the ability of the targeting sequence to target a protein to the exosporium. FIG. 1 lists the percent identity of each of corresponding amino acids of each sequence to amino acids 20-35 of BclA ("20-35% Identity") and to amino acids 25-35 of BclA ("25-35% Identity"). Thus, for example, as compared to amino acids 20-35 of BclA, the corresponding amino acids of BetA/BAS3290 are about 81.3% identical, the corresponding amino acids of BAS4623 are about 50.0% identical, the corresponding amino acids of BclB are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIG. 1.

With respect to amino acids 25-35 of BclA, the corresponding amino acids of BetA/BAS3290 are about 90.9% identical, the corresponding amino acids of BAS4623 are about 72.7% identical, the corresponding amino acids of BclB are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIG. 1.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence having at least about 43% identity with amino acids 20-35 of SEQ ID NO. 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively the targeting sequence consists of an amino acid sequence having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence having at least about 50% identity with amino acids 20-35 of SEQ ID NO: 1, wherein the identity with amino acids 25-35 is at least about 72%.

The targeting sequence can also comprises an amino acid sequence having at least about 56% identity with amino acids 20-35 of SEQ ID NO: 1, wherein the identity with amino acids 25-35 is at least about 63%. Alternatively, the targeting sequence consists of an amino acid sequence having at least about 56% identity with amino acids 20-35 of SEQ ID NO: 1, wherein the identity with amino acids 25-35 is at least about 63%.

Alternatively, the targeting sequence can comprise an amino sequence having at least about 62% identity with amino acids 20-35 of SEQ ID NO: 1, wherein the identity with amino acids 25-35 is at least about 72%. The targeting sequence can also consist of an amino acid sequence having at least about 62% identity with amino acids 20-35 of SEQ ID NO: 1, wherein the identity with amino acids 25-35 of SEQ ID NO:1 is at least about 72%.

The targeting sequence can also comprises an amino sequence having at least about 75% identity with amino acids 20-35 of SEQ ID NO: 1, wherein the identity with amino acids 25-35 is at least about 72%. Alternatively, the targeting sequence consists of an amino acid sequence having at least about 75% identity with amino acids 20-35 of SEQ ID NO: 1, wherein the identity with amino acids 25-35 of SEQ ID NO:1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence having at least about 75% identity with amino acids 20-35 of SEQ ID NO: 1, wherein the identity with amino acids 25-35 of SEQ ID NO:1 is at least about 81%.

The targeting sequence can also comprise an amino acid sequence having at least about 81% identity with amino acids 20-35 of SEQ ID NO:1, wherein the identity with amino acids 25-35 is at least about 81%. Alternatively, the targeting sequence consists of an amino acid sequence having at least about 81% identity with amino acids 20-35 of SEQ ID NO:1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of BclA, the corresponding amino acids of BetA/BAS3290, BAS4263, BclB, BAS1882, the KBAB4 2280 gene product, or the KBAB 3572 gene product, or a sequence comprising any of the above noted sequence identities to amino acids 20-35 and 25-35 of BclA is present.

In any of the above targeting sequences, the targeting sequence can comprise the amino acid sequence GXT at its carboxy terminus, wherein X is any amino acid.

Fusion Proteins

The present invention relates to fusion proteins comprising a targeting sequence and at least one plant growth stimulating protein or peptide, wherein the plant growth stimulating protein or peptide comprises a peptide hormone, a non-hormone peptide, or an enzyme involved in the production of a plant growth stimulating compound.

The present invention also relates to fusion proteins comprising a targeting sequence and at least one protein or peptide that protects a plant from a pathogen.

In addition, the present invention relates to fusion proteins comprising a targeting sequence and at least one root binding protein or peptide.

In any of the fusion proteins described herein, the targeting sequence can be any of the targeting sequences described above in the preceding section.

The fusion protein can be made using standard cloning and molecular biology methods known in the art. For example, a gene encoding a protein or peptide (e.g., a gene encoding a plant growth stimulating protein or peptide) can be amplified by polymerase chain reaction (PCR) and ligated to DNA coding for any of the above-described targeting sequences to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed with the vector can be readily identified and isolated. Where the vector is a plasmid, the plasmid suitably also comprises an origin of replication. The DNA encoding the fusion protein is suitably under the control of a promoter which will cause expression of the fusion protein on the exosporium of a *B. cereus* family member endospore (e.g., a native bclA promoter from a *B. cereus* family member).

The fusion protein can also comprise additional polypeptide sequences that are not part of the targeting sequence or the plant growth stimulating protein or peptide, the protein or peptide that protects a plant from a pathogen, or the root binding protein or peptide. For example, the fusion protein can include tags or markers to facilitate purification or visualization of the fusion protein (e.g., a polyhistidine tag or a fluorescent protein such as GFP or YFP).

Plant Growth Stimulating Proteins and Peptides

As noted above, the present invention relates to fusion proteins comprising a targeting sequence and at least one plant growth stimulating protein or peptide, wherein the plant growth stimulating protein or peptide comprises a peptide hormone, a non-hormone peptide, or an enzyme involved in the production of a plant growth stimulating compound.

For example, where the plant growth stimulating protein or peptide comprises a peptide hormone, the peptide hormone can comprise a phytosulfokine (e.g., phytosulfokine-α), clavata 3 (CLV3), systemin, Zm1GF, or a SCR/SP11.

Where the plant growth stimulating protein or peptide comprises a non-hormone peptide, the non-hormone peptide can comprise a RKN 16D10, Hg-Syv46, an eNOD40 peptide, RHPP, or kunitz trypsin inhibitor.

The plant growth stimulating protein or peptide can comprise an enzyme involved in the production of a plant growth stimulating compound. The enzyme involved in the production of a plant growth stimulating compound can be any enzyme that catalyzes any step in a biological synthesis pathway for a compound that stimulates plant growth.

The plant growth stimulating compound can comprise a compound produced by bacteria or fungi in the rhizosphere, e.g., 2,3-butanediol.

Alternatively, the plant growth stimulating compound can comprise a plant growth hormone, e.g., a cytokinin or an auxin.

Where the plant growth stimulating compound comprises a cytokinin, the cytokinin can comprise kinetin, cis-zeatin, trans-zeatin, 6-benzylaminopurine, dihydroxyzeatin, N6-(D2-isopentenyl) adenine, ribosylzeatin, N6-(D2-isopentenyl) adenosine, 2-methylthio-cis-ribosylzeatin, cis-ribosylzeatin, trans-ribosylzeatin, 2-methylthio-trans-ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, meta-methyltopolin, or a combination thereof.

Where the plant growth stimulating compound comprises an auxin, the auxin can comprise indole-3-acetic acid, indole-3-pyruvic acid, ndole-3-acetaldoxime, indole-3-acetamide, indole-3-acetonitrile, indole-3-ethanol, indole-3-pyruvate, indole-3-acetaldoxime, indole-3-butyric acid, a phenylacetic acid, or 4-chloroindole-3-acetic acid, or a combination thereof.

The enzyme involved in the production of a plant growth stimulating compound can comprise an acetoin reductase, an indole-3-acetamide hydrolase, a tryptophan monoxygenase, an acetolactate synthetase, an α-acetolactate decarboxylase, a pyruvate decarboxylase, a diacetyl reductase, a butanediol dehydrogenase, an aminotransferase (e.g., tryptophan aminotransferase), a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5' ribonucleotide phosphohydrolase, an adenosine nucleosidase, a zeatin cis-trans isomerase, a zeatin 0-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, or a zeatin reductase.

Where the enzyme comprises a protease or peptidase, the protease or peptidase can be a protease or peptidase that cleaves proteins or peptides to create a bioactive peptide. The bioactive peptide can be any peptide that exerts a biological activity.

Examples of bioactive peptides include RKN 16D10 and RHPP.

The protease or peptidase that cleaves proteins or peptides to create a bioactive peptide can comprise subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

The protease or peptidase can cleave proteins in a protein-rich meal (e.g., soybean meal or yeast extract).

Proteins and Peptides that Protects Plants from Pathogens

The present invention relates to fusion proteins comprising a targeting sequence and at least one protein or peptide that protects a plant from a pathogen.

For example, the protein or peptide that protects a plant from a pathogen can comprise a plant immune system enhancer protein or peptide. The plant immune system enhancer protein or peptide can be any protein or peptide that has a beneficial effect on the immune system of a plant. Suitable plant immune system enhancer proteins and peptides include harpins, α-elastins, β-elastins, cryptogeins, flagellin proteins, and flagellin peptides.

Alternatively, the protein or peptide that protects a plant from a pathogen can be a protein or peptide that has antibacterial activity, antifungal activity, or both antibacterial and antifungal activity. Examples of such proteins and peptides include bacteriocins, lysozymes, siderophores, avidins, streptavidins, conalbumins, albumins, or lactoferrins.

The protein that protects a plant from a pathogen can comprise an enzyme. Suitable enzymes include proteases and lactonases. The proteases and lactonases can be specific for a bacterial signaling molecule (e.g., a bacterial lactone homoserine signaling molecule).

Where the enzyme is a lactonase, the lactonase can comprise 1,4-lactonase, 2-pyrone-4,6-dicarboxylate lactonase, 3-oxoadipate enol-lactonase, actinomycin lactonase, deoxylimonate A-ring-lactonase, gluconolactonase L-rhamnono-1,4-lactonase, limonin-D-ring-lactonase, steroid-lactonase, triacetate-lactonase, or xylono-1,4-lactonase.

The enzyme can also be an enzyme that is specific for a cellular component of a bacterium or fungus. For example, the enzyme can comprise a β-1,3-glucanase, a β-1,4-glucanase, a β-1,6-glucanase, a chitosinase, a chitinase, a chitosinase-like enzyme, a lyticase, a peptidase, a proteinase, a protease (e.g., an alkaline protease, an acid protease, or a neutral protease), a mutanolysin, a stapholysin, or a lysozyme.

For any of the above fusion proteins comprising a protein or peptide that protects a plant from a pathogen, the pathogen can be a bacterial pathogen or a fungal pathogen. For example, the pathogen can comprise an α-class Proteobacterium, a β-class Proteobacterium, a γ-class Proteobacterium, or a combination thereof. Particular bacterial pathogens include *Agrobacterium tumefaciens, Pantoea stewartii, Envinia carotovora, Ralstonia solanacearum, Pseudomonas syringae, Pseudomonas aeruginosa, Xanthomonas campestris*, and combinations thereof.

Other pathogens include *Acarosporina microspora, Aceria guerreronis, Achlya conspicua, Achlya klebsiana, Achlysiella williamsi, Acholeplasmataceae, Acidovorax avenae, Acremonium strictum, Acrocalymma medicaginis, Acrodontium simplex, Acrophialophora fusispora, Acrosporium tingitaninum, Aecidium, Aecidium aechmantherae, Aecidium amaryllidis, Aecidium breyniae, Aecidium campanulastri, Aecidium cannabis, Aecidium cantensis, Aecidium caspicum, Aecidium foeniculi, Agrobacterium tumefaciens, Albonectria rigidiuscula, Albugo bliti, Albugo candida, Albugo ipomoeae-panduratae, Albugo laibachii, Albugo occidentalis, Albugo tragopogonis, Alternaria, Alternaria alternata, Alternaria brassicae, Alternaria brassicicola, Alternaria carthami, Alternaria cinerariae, Alternaria citri, Alternaria dauci, Alternaria dianthi, Alternaria dianthicola, Alternaria euphorbiicola, Alternaria helianthi, Alternaria helianthicola, Alternaria japonica, Alternaria leucanthemi, Alternaria limicola, Alternaria linicola, Alternaria mali, Alternaria padwickii, Alternaria panax, Alternaria radicina, Alternaria raphani, Alternaria saponariae, Alternaria senecionis, Alternaria solani, Alternaria tenuissima, Alternaria triticina, Alternaria zinniae, Amazonia, Amphobotrys ricini, Anguillosporella vermiformis, Anguina* (genus), *Anguina agrostis, Anguina amsinckiae, Anguina australis, Anguina balsamophila, Anguina funesta, Anguina graminis, Anguina spermophaga, Anguina tritici, Anisogramma anomala, Anthostomella pullulans, Antrodia albida, Antrodia serialiformis, Antrodia serialis, Aphanomyces cladogamus, Aphanomyces cochlioides, Aphanomyces euteiches, Aphanomyces euteiches* f. sp. *pisi, Aphanomyces raphani, Aphelenchoides, Aphelenchoides arachidis, Aphelenchoides besseyi, Aphelenchoides fragariae, Aphelenchoides parietinus, Aphelenchoides ritzemabosi, Aphelenchus avenae, Apiognomonia errabunda, Apiognomonia veneta, Apiospora montagnei, Appendiculella, Armillaria, Armillaria affinis, Armillaria apalosclera, Armillaria camerunensis, Armillaria duplicate, Armillaria fellea, Armillaria fumosa, Armillaria fuscipes, Armillaria griseomellea, Armillaria heimii, Armillaria mellea, Armillaria melleorubens, Armillaria montagnei, Armillaria omnituens, Armillaria pallidula, Armillaria paulensis, Armillaria pelliculata, Armillaria procera, Armillaria puiggarii, Armillaria singular, Armillaria socialis, Armillaria solidipes, Armillaria tabescens, Armillaria tigrensis, Armillaria umbrinobrunnea, Armillaria viridiflava, Armillaria yungensis, Arthrocladiella, Arthuriomyces peckianus, Ascochyta asparagine, Ascochyta bohemica, Ascochyta caricae, Ascochyta doronici, Ascochyta fabae* f. sp. *lentis, Ascochyta graminea, Ascochyta hordei, Ascochyta humuli, Ascochyta pisi, Ascochyta prasadii, Ascochyta sorghi, Ascochyta spinaciae, Ascochyta tarda, Ascochyta tritici, Ascospora ruborum, Ashbya gossypii, Aspergillus aculeatus, Aspergillus fischerianus, Aspergillus niger, Asperisporium caricae, Asperisporium minutulum, Asteridiella, Asteridiella perseae, Asteroma caryae, Asteroma coryli, Asteroma inconspicuum, Athelia arachnoidea, Athelia rolfsii, Aurantiporus fissilis, Belonolaimus, Belonolaimus gracilis, Belonolaimus longicaudatus, Beniowskia sphaeroidea, Bionectria ochroleuca, Bipolaris, Bipolaris cactivora, Bipolaris cookie, Bipolaris incurvata, Bipolaris sacchari, Biscogniauxia capnodes* var. *capnodes, Biscogniauxia marginata, Biscogniauxia nummularia, Bjerkandera adusta, Blakeslea trispora, Blumeria graminis, Botryodiplodia oncidii, Botryodiplodia ulmicola, Botryosphaeria cocogena, Botryosphaeria corticola, Botryosphaeria disrupta, Botryosphaeria dothidea, Botryosphaeria marconii, Botryosphaeria obtuse, Botryosphaeria quercuum, Botryosphaeria rhodina, Botryosphaeria ribis, Botryosphaeria stevensii, Botryosporium pulchrum, Botryotinia, Botryotinia fuckeliana, Botrytis anthophila, Botrytis cinerea, Botrytis fabae, Bremia lactucae, Brenneria salicis, Briosia ampelophaga, Bulbomicrosphaera, Burkholderia andropogonis, Burkholderia caryophylli, Burkholderia glumae, Cadophora malorum, Caespitotheca, Calonectria indusiata, Calonectria kyotensis, Calonectria quinqueseptata, Calvatia versispora, Camarosporium pistaciae, Camarotella acrocomiae, Camarotella costaricensis, Candidatus Liberibacter, Capitorostrum cocoes, Capnodium footii, Capnodium mangiferum, Capnodium ramosum, Capnodium theae, Caulimoviridae, Cephaleuros virescens, Cephalosporium gramineum, Ceratobasidium cereal, Ceratobasidium cornigerum, Ceratobasidium noxium, Ceratobasidium ramicola, Ceratobasidium setariae, Ceratobasidium stevensii, Ceratocystis adiposa, Ceratocystis coerulescens, Ceratocystis fimbriata, Ceratocystis moniliformis, Ceratocystis paradoxa, Ceratocystis pilifera, Ceratocystis pluriannulata, Ceratorhiza hydrophila, Ceratospermopsis, Cercoseptoria ocellata, Cercospora, Cercospora angreci, Cercospora apii, Cercospora apii* f. sp. *clerodendri, Cercospora apiicola, Cercospora arachidicola, Cercospora asparagi, Cercospora atrofiliformis, Cercospora beticola, Cercospora brachypus, Cercospora brassicicola, Cercospora brunkii, Cercospora cannabis, Cercospora cantuariensis, Cercospora capsici, Cercospora carotae, Cercospora corylina, Cercospora fragariae, Cercospora fuchsiae, Cercospora fusca, Cercospora fusimaculans, Cercospora gerberae, Cercospora halstedii, Cercospora handelii, Cercospora hayi, Cercospora hydrangea, Cercospora kikuchii, Cercospora lentis, Cercospora liquidambaris, Cercospora longipes, Cercospora longissima, Cercospora mamaonis, Cercospora mangiferae, Cercospora medicaginis, Cercospora melongenae, Cercospora minima, Cercospora minuta, Cercospora nicotianae, Cercospora odontoglossi, Cercospora papaya, Cercospora penniseti, Cercospora pisa-sativae, Cercospora platanicola, Cercospora puderii, Cercospora pulcherrima, Cercospora rhapidicola, Cercospora rosicola, Cercospora rubrotincta, Cercospora sojina, Cercospora solani, Cercospora solanituberosi, Cercospora sorghi, Cercospora theae, Cercospora tuberculans, Cercospora vexans, Cercospora vicosae, Cercospora zeae-maydis, Cercospora zebrina, Cercospora zonata, Cercosporella rubi, Cereal cyst nematode, Ceriporia spissa, Ceriporia xylostromatoides, Cerrena unicolor, Ceuthospora lauri, Choanephora, Choanephora cucurbitarum, Choanephora infundibulifera, Chondrostereum purpureum, Chrysomyxa ledi* var. *rhododendri, Chrysomyxa ledicola, Chrysomyxa piperiana, Chrysomyxa roanensis, Cladosporium, Cladosporium arthropodii, Cladosporium caryigenum, Cladosporium cladosporioides, Cladosporium cladosporioides* f. sp. *pisicola, Cladosporium cucumerinum, Cladosporium herbarum, Cladosporium musae, Cladosporium oncobae, Clavibacter michiganensis, Claviceps fusiformis, Claviceps purpurea, Claviceps sorghi, Claviceps zizaniae, Climacodon pulcherrimus, Climacodon septentrionalis, Clitocybe parasitica, Clonostachys rosea* f. *rosea,*

*Clypeoporthe iliau, Cochliobolus, Cochliobolus carbonum, Cochliobolus cymbopogonis, Cochliobolus hawaiiensis, Cochliobolus heterostrophus, Cochliobolus lunatus, Cochliobolus miyabeanus, Cochliobolus ravenelii, Cochliobolus sativus, Cochliobolus setariae, Cochliobolus spicifer, Cochliobolus stenospilus, Cochliobolus tuberculatus, Cochliobolus victoriae, Coleosporium helianthi, Coleosporium Ipomoeae, Coleosporium madiae, Coleosporium pacificum, Coleosporium tussilaginis, Colletotrichum acutatum, Colletotrichum arachidis, Colletotrichum capsici, Colletotrichum cereale, Colletotrichum crassipes, Colletotrichum dematium, Colletotrichum dematium* f. *spinaciae, Colletotrichum derridis, Colletotrichum destructivum, Colletotrichum fragariae, Colletotrichum gossypii, Colletotrichum higginsianum, Colletotrichum kahawae, Colletotrichum lindemuthianum, Colletotrichum lini, Colletotrichum mangenotii, Colletotrichum musae, Colletotrichum nigrum, Colletotrichum orbiculare, Colletotrichum pisi, Colletotrichum sublineolum, Colletotrichum trichellum, Colletotrichum trifolii, Colletotrichum truncatum, Coniella castaneicola, Coniella diplodiella, Coniella fragariae, Coniothecium chomatosporum, Coniothyrium celtidis-australis, Coniothyrium henriquesii, Coniothyrium rosarum, Coniothyrium wernsdorffiae, Coprinopsis psychromorbida, Cordana johnstonii, Cordana musae, Coriolopsis floccose, Coriolopsis gallica, Corticium invisum, Corticium penicillatum, Corticium theae, Coryneopsis rubi, Corynespora cassiicola, Coryneum rhododendri, Crinipellis sarmentosa, Cronartium ribicola, Cryphonectriaceae, Cryptocline cyclaminis, Cryptomeliola, Cryptoporus volvatus, Cryptosporella umbrina, Cryptosporiopsis tarraconensis, Cryptosporium minimum, Curvularia caricae-papayae, Curvularia penniseti, Curvularia senegalensis, Curvularia trifolii, Cylindrocarpon candidum, Cylindrocarpon ianthothele* var. *ianthothele, Cylindrocarpon magnusianum, Cylindrocarpon musae, Cylindrocladiella camelliae, Cylindrocladiella parva, Cylindrocladium clavatum, Cylindrocladium lanceolatum, Cylindrocladium peruvianum, Cylindrocladium pteridis, Cylindrosporium cannabinum, Cylindrosporium juglandis, Cylindrosporium rubi, Cymadothea trifolii, Cytospora, Cytospora palmarum, Cytospora personata, Cytospora platani, Cytospora sacchari, Cytospora sacculus, Cytospora terebinthi, Cytosporina ludibunda, Dactuliophora elongata, Daedaleopsis confragosa, Dasineura urticae, Datronia scutellata, Davidiella carinthiaca, Davidiella dianthi, Davidiella tassiana, Deightoniella papuana, Deightoniella torulosa, Dendrophoma marconii, Dendrophora erumpens, Denticularia mangiferae, Dermea pseudotsugae, Diaporthaceae, Diaporthe, Diaporthe arctii, Diaporthe citri, Diaporthe dulcamarae, Diaporthe eres, Diaporthe helianthi, Diaporthe lagunensis, Diaporthe lokoyae, Diaporthe melonis, Diaporthe orthoceras, Diaporthe perniciosa, Diaporthe phaseolorum, Diaporthe phaseolorum* var. *caulivora, Diaporthe phaseolorum* var. *phaseolorum, Diaporthe phaseolorum* var. *sojae, Diaporthe rudis, Diaporthe tanakae, Diaporthe toxica, Dibotryon morbosum, Dicarpella dryina, Didymella bryoniae, Didymella fabae, Didymella lycopersici, Didymosphaeria arachidicola, Didymosphaeria taiwanensis, Dilophospora alopecuri, Dimeriella sacchari, Diplocarpon earlianum, Diplocarpon mali, Diplocarpon mespili, Diplocarpon rosae, Diplodia laelio-cattleyae, Diplodia manihoti, Diplodia paraphysaria, Diplodia theae-sinensis, Discosia artocreas, Guignardia fulvida, Discostroma corticola, Distocercospora, Distocercospora livistonae, Ditylenchus, Ditylenchus africanus, Ditylenchus angustus, Ditylenchus destructor, Ditylenchus dipsaci, Dolichodorus heterocephalus, Dothideomycetes, Dothiorella aromatic, Dothiorella dominicana, Dothiorella gregaria, Dothiorella ulmi, Drechslera avenacea, Drechslera campanulata, Drechslera dematioidea, Drechslera gigantea, Drechslera glycines, Drechslera musae-sapientium, Drechslera teres* f. *maculate, Drechslera wirreganensis, Durandiella pseudotsugae, Eballistra lineata, Eballistra oryzae, Eballistraceae, Echinodontium tinctorium, Ectendomeliola, Elsinoe ampelina, Elsinoe australis, Elsinoe batatas, Elsinoe brasiliensis, Elsinoe fawcettii, Elsinoe leucospila, Elsinoe mangiferae, Elsinoe pini, Elsinoe randii, Elsinoe rosarum, Elsinoe sacchari, Elsinoe theae, Elsinoe veneta, Endomeliola, Endothia radicalis, Endothiella gyrosa, Entoleuca mammata, Entorrhizomycetes, Entyloma ageratinae, Entyloma dahlia, Entyloma ellisii, Epicoccum nigrum, Ergot, Erwinia, Envinia chrysanthemi, Erwinia psidii, Erysiphaceae, Erysiphales, Erysiphe, Erysiphe alphitoides, Erysiphe betae, Erysiphe brunneopunctata, Erysiphe cichoracearum, Erysiphe cruciferarum, Erysiphe flexuosa, Erysiphe graminis f.* sp. *avenae, Erysiphe graminis* f. sp. *tritici, Erysiphe heraclei, Erysiphe pisi, Eutypella parasitica, Eutypella scoparia, Exobasidium burtii, Exobasidium reticulatum, Exobasidium vaccinii* var. *japonicum, Exobasidium vaccinii-uliginosi, Exobasidium vexans, Exophiala, Flavescence doree, Fomes fasciatus, Fomes lamaensis, Fomes meliae, Fomitopsis cajanderi, Fomitopsis palustris, Fomitopsis rosea, Fomitopsis spraguei, Fomitopsis supina, Forma specialis, Frommeella tormentillae, Fusarium, Fusarium affine, Fusarium arthrosporioides, Fusarium circinatum, Fusarium crookwellense, Fusarium culmorum, Fusarium graminearum, Fusarium incarnatum, Fusarium solani, Fusarium merismoides, Fusarium oxysporum* f. sp. *albedinis, Fusarium oxysporum* f. sp. *asparagi, Fusarium oxysporum* f. sp. *batatas, Fusarium oxysporum* f. sp. *betae, Fusarium oxysporum* f. sp. *cannabis, Fusarium oxysporum* f. sp. *citri, Fusarium oxysporum* f. sp. *coffea, Fusarium oxysporum* f. sp. *cubense, Fusarium oxysporum* f. sp. *cyclaminis, Fusarium oxysporum* f. sp. *dianthi, Fusarium oxysporum* f. sp. *lentis, Fusarium oxysporum* f. sp. *lini, Fusarium oxysporum* f. sp. *lycopersici, Fusarium oxysporum* f. sp. *medicaginis, Fusarium oxysporum* f. sp. *pisi, Fusarium oxysporum* f. sp. *radicis-lycopersici, Fusarium pallidoroseum, Fusarium proliferatum, Fusarium redolens, Fusarium sacchari, Fusarium solani* f. sp. *pisi, Fusarium sporotrichioides, Fusarium subglutinans, Fusarium sulphureum, Fuscoporia torulosa, Fusicladium pisicola, Fusicoccum aesculi, Fusicoccum amygdali, Gaeumannomyces graminis* var *tritici, Gaeumannomyces graminis* var. *avenae, Gaeumannomyces graminis* var. *graminis, Galactomyces candidum, Ganoderma brownii, Ganoderma lobatum, Ganoderma orbiforme, Ganoderma philippii, Ganoderma tornatum, Ganoderma zonatum, Geastrumia polystigmatis, Georgefischeriaceae, Georgefischeriales, Geosmithia morbida, Geotrichum, Geotrichum candidum, Geotrichum candidum* var. *citri-aurantii, Geotrichum klebahnii, Gibberella, Gibberella acuminata, Gibberella avenacea, Gibberella baccata, Gibberella cyanogena, Gibberella fujikuroi, Gibberella fujikuroi* var. *subglutinans, Gibberella intricans, Gibberella pulicaris, Gibberella stilboides, Gibberella xylarioides, Gibberella zeae, Gibellina cerealis, Gilbertella persicaria, Gjaerumiaceae, Gliocladium vermoeseni, Globodera pallida, Globodera rostochiensis, Globodera tabacum, Gloeocercospora sorghi, Gloeocystidiellum porosum, Gloeophyllum mexicanum, Gloeophyllum trabeum, Gloeoporus dichrous, Gloeosporium cattleyae, Gloeosporium theae-sinensis, Glomerella cingulate, Glomerella glycines, Glomerella graminicola, Glomerella tucumanensis, Gnomo-* nia caryae, Gnomonia comari, Gnomonia dispora, Gnomonia iliau, Gnomonia leptostyla, Gnomonia nerviseda, Gnomonia rubi, Golovinomyces cichoracearum var. latisporus, Granulobasidium vellereum, Graphiola phoenicis, Graphium rigidum, Graphium rubrum, Graphyllium pentamerum, Grovesinia pyramidalis, Guignardia bidwellii f. muscadinii, Guignardia camelliae, Guignardia citricarpa, Guignardia mangiferae, Guignardia musae, Guignardia philoprina, Gummosis, Gymnoconia nitens, Gymnopus dryophilus, Gymnosporangium clavipes, Gymnosporangium sabinae, Gymnosporangium globosum, Gymnosporangium jumperi-virginianae, Gymnosporangium kernianum, Gymnosporangium nelsonii, Gymnosporangium yamadae, Haematonectria haematococca, Hansenula subpelliculosa, Hapalosphaeria deformans, Haplobasidion musae, Haustorium, Helicobasidium compactum, Helicobasidium longisporum, Helicobasidium purpureum, Helicoma muelleri, Helicotylenchus, Helicotylenchus dihystera, Helicotylenchus multicinctus, Helminthosporium cookei, Helminthosporium papulosum, Helminthosporium solani, Helotiales, Hemicriconemoides kanayaensis, Hemicriconemoides mangiferae, Hemicycliophora arenaria, Hemlock woolly adelgid, Hendersonia creberrima, Hendersonia theicola, Hericium coralloides, Heterobasidion annosum, Heterodera, Heterodera amygdali, Heterodera arenaria, Heterodera aucklandica, Heterodera avenae, Heterodera bergeniae, Heterodera bifenestra, Heterodera cacti, Heterodera cajani, Heterodera canadensis, Heterodera cardiolata, Heterodera carotae, Heterodera ciceri, Heterodera cruciferae, Heterodera delvii, Heterodera elachista, Heterodera filipjevi, Heterodera gambiensis, Heterodera goettingiana, Heterodera hordecalis, Heterodera humuli, Heterodera latipons, Heterodera medicaginis, Heterodera oryzae, Heterodera oryzicola, Heterodera rosii, Heterodera sacchari, Heterodera schachtii, Heterodera tabacum, Heterodera trifolii, Heteroderidae, Hexagonia hydnoides, Hirschmanniella oryzae, Hoplolaimus galeatus, Hoplolaimidae, Hoplolaimus columbus, Hoplolaimus indicus, Hoplolaimus magnistylus, Hoplolaimus pararobustus, Hoplolaimus seinhorsti, Hoplolaimus uniformis, Huanglongbing, Hyaloperonospora, Hyaloperonospora arabidopsidis, Hyaloperonospora brassicae, Hyaloperonospora parasitica, Hymenula affinis, Hyphodermella corrugata, Hyphodontia aspera, Hyphodontia sambuci, Hypochnus, Hypoxylon tinctor, Idriella lunata, Inonotus arizonicus, Inonotus cuticularis, Inonotus dryophilus, Inonotus hispidus, Inonotus ludovicianus, Inonotus munzii, Inonotus tamaricis, Irenopsis, Irpex destruens, Irpex lacteus, Isariopsis clavispora, Johncouchia mangiferae, Kabatiella caulivora, Kabatiella lini, Karnal bunt, Khuskia oryzae, Kretzschmaria deusta, Kretzschmaria zonata, Kuehneola uredinis, Kutilakesa pironii, Labrella coryli, Laeticorticium roseum, Laetiporus baudonii, Lagenocystis radicicola, Laricifomes officinalis, Lasiodiplodia theobromas, Leandria momordicae, Leifsonia xyli xyli, Lentinus tigrinus, Lenzites betulina, Lenzites elegans, Lepteutypa cupressi, Leptodontidium elatius var. elatius, Leptographium microsporum, Leptosphaeria acuta, Leptosphaeria cannabina, Leptosphaeria coniothyrium, Leptosphaeria libanotis, Leptosphaeria lindquistii, Leptosphaeria maculans, Leptosphaeria musarum, Leptosphaeria pratensis, Leptosphaeria sacchari, Leptosphaeria woroninii, Leptosphaerulina crassiasca, Leptosphaerulina trifolii, Leptothyrium nervisedum, Leptotrochila medicaginis, Leucocytospora leucostoma, Leucostoma auerswaldii, Leucostoma kunzei, Leucostoma persoonii, Leveillula compositarum f. helianthi, Leveillula leguminosarum f. lentis, Leveillula taurica, Ligniera pilorum, Limacinula tenuis, Linochora graminis, Longidorus africanus, Longidorus maximus, Longidorus sylphus, Lopharia crassa, Lophodermium, Lophodermium aucupariae, Lophodermium schweinitzii, Lophodermium seditiosum, Macrophoma mangiferae, Macrophoma theicola, Macrophomina phaseolina, Macrosporium cocos, Magnaporthe, Magnaporthe grisea, Magnaporthe salvinii, Mamianiella coryli, Marasmiellus cocophilus, Marasmiellus inoderma, Marasmiellus scandens, Marasmiellus stenophyllus, Marasmius crinis-equi, Marasmius sacchari, Marasmius semiustus, Marasmius stenophyllus, Marasmius tenuissimus, Massarina walkeri, Mauginiella scaettae, Melampsora, Melampsora lini var. lini, Melampsora medusae, Melampsora occidentalis, Melanconis carthusiana, Melanconium juglandinum, Meliola, Meliola mangiferae, Meliolaceae, Meloidogyne acronea, Meloidogyne arenaria, Meloidogyne artiellia, Meloidogyne brevicauda, Meloidogyne chitwoodi, Meloidogyne enterolobii, Meloidogyne fruglia, Meloidogyne gajuscus, Meloidogyne incognita, Meloidogyne javanica, Meloidogyne naasi, Meloidogyne partityla, Meloidogyne thamesi, Meripilus giganteus, Merlinius brevidens, Meruliopsis ambigua, Mesocriconema xenoplax, Microascus brevicaulis, Microbotryum violaceum, Microdochium bolleyi, Microdochium dimerum, Microdochium panattonianum, Microdochium phragmitis, Microsphaera, Microsphaera coryli, Microsphaera diffusa, Microsphaera ellisii, Microsphaera euphorbiae, Microsphaera hommae, Microsphaera penicillata, Microsphaera penicillata var. vaccinii, Microsphaera vaccinii, Microsphaera verruculosa, Microstroma juglandis, Moesziomyces bullatus, Monilinia azaleae, Monilinia fructicola, Monilinia fructigena, Monilinia laxa, Monilinia mali, Moniliophthora perniciosa, Moniliophthora roreri, Monilochaetes infuscans, Monochaetia coryli, Monochaetia mali, Monographella albescens, Monographella cucumerina, Monographella nivalis var. neglecta, Monographella nivalis var. nivalis, Mononegavirales, Monosporascus cannonballus, Monosporascus eutypoides, Monostichella coryli, Mucor circinelloides, Mucor hiemalis, Mucor hiemalis f. silvaticus, Mucor mucedo, Mucor paronychius, Mucor piriformis, Mucor racemosus, Mycena citricolor, Mycena maculate, Mycocentrospora acerina, Mycoleptodiscus terrestris, Mycosphaerella angulata, Mycosphaerella arachidis, Mycosphaerella areola, Mycosphaerella berkeleyi, Mycosphaerella bolleana, Mycosphaerella brassicicola, Mycosphaerella caricae, Mycosphaerella caryigena, Mycosphaerella cerasella, Mycosphaerella citri, Mycosphaerella coffeicola, Mycosphaerella confusa, Mycosphaerella cruenta, Mycosphaerella dendroides, Mycosphaerella eumusae, Mycosphaerella fragariae, Mycosphaerella gossypina, Mycosphaerella graminicola, Mycosphaerella henningsii, Mycosphaerella horii, Mycosphaerella juglandis, Mycosphaerella lageniformis, Mycosphaerella linicola, Mycosphaerella louisianae, Mycosphaerella musae, Mycosphaerella musicola, Mycosphaerella palmicola, Mycosphaerella pinodes, Mycosphaerella pistaciarum, Mycosphaerella pistacina, Mycosphaerella platanifolia, Mycosphaerella polymorpha, Mycosphaerella pomi, Mycosphaerella punctiformis, Mycosphaerella pyri, Didymella rabiei, Mycosphaerella recutita, Mycosphaerella rosicola, Mycosphaerella rubi, Mycosphaerella stigmina-platani, Mycosphaerella striatiformans, Mycovellosiella concors, Mycovellosiella fulva, Mycovellosiella koepkei, Mycovellosiella vaginae, Myriogenospora aciculispora, Myrothecium roridum, Myrothecium verrucaria, Nacobbus aberrans, Nacobbus dorsalis, Naevala perexigua, Naohidemyces vaccinii, Nectria, Nectria cinnabarina, Nectria coccinea, *Nectria ditissima*, *ectria foliicola*, *Nectria mammoidea* var. *rubi*, *Nectria mauritiicola*, *Nectria peziza*, *Nectria pseudotrichia*, *Nectria radicicola*, *Nectria ramulariae*, *Nectriella pironii*, *Nemania diffusa*, *Nemania serpens* var. *serpens*, *Nematospora coryli*, *Neocosmospora vasinfecta*, *Neodeightonia phoenicum*, *Neoerysiphe*, *Neofabraea malicorticis*, *Neofabraea perennans*, *Neofusicoccum mangiferae*, *Neonectria galligena*, *Oidiopsis gossypii*, *Oidium* (genus), *Oidium arachidis*, *Oidium caricae-papayae*, *Oidium indicum*, *Oidium mangiferae*, *Oidium manihotis*, *Oidium tingitaninum*, *Olpidium brassicae*, *Omphalia tralucida*, *Oncobasidium theobromas*, *Onnia tomentosa*, *Ophiobolus anguillides*, *Ophiobolus cannabinus*, *Ophioirenina*, *Ophiostoma ulmi*, *Ophiostoma wageneri*, *Ovulariopsis papayae*, *Ovulinia azaleae*, *Ovulitis azaleae*, *Oxyporus corticola*, *Oxyporus latemarginatus*, *Oxyporus populinus*, *Oxyporus similis*, *Ozonium texanum* var. *parasiticum*, *Paecilomyces fulvus*, *Paralongidorus maximus*, *Paratrichodorus christiei*, *Paratrichodorus minor*, *Paratylenchus curvitatus*, *Paratylenchus elachistus*, *Paratylenchus hamatus*, *Paratylenchus macrophallus*, *Paratylenchus microdorus*, *Paratylenchus projectus*, *Paratylenchus tenuicaudatus*, *Pathovar*, *Pauahia*, *Peach latent mosaic viroid*, *Pectobacterium carotovorum*, *Peltaster fructicola*, *Penicillium aurantiogriseum*, *Penicillium digitatum*, *Penicillium expansum*, *Penicillium funiculosum*, *Penicillium glabrum*, *Penicillium italicum*, *Penicillium purpurogenum*, *Penicillium ulaiense*, *Peniophora*, *Peniophora albobadia*, *Peniophora cinerea*, *Peniophora quercina*, *Peniophora sacrata*, *Perenniporia fraxinea*, *Perenniporia fraxinophila*, *Perenniporia medulla-panis*, *Perenniporia subacida*, *Periconia circinata*, *Periconiella cocoes*, *Peridermium californicum*, *Peronosclerospora miscanthi*, *Peronosclerospora sacchari*, *Peronosclerospora sorghi*, *Peronospora*, *Peronospora anemones*, *Peronospora antirrhini*, *Peronospora arborescens*, *Peronospora conglomerata*, *Peronospora destructor*, *Peronospora dianthi*, *Peronospora dianthicola*, *Peronospora farinosa*, *Peronospora farinosa* f. sp. *betae*, *Peronospora hyoscyami* f. sp. *tabacina*, *Peronospora manshurica*, *Peronospora potentillae*, *Peronospora sparsa*, *Peronospora trifoliorum*, *Peronospora valerianellae*, *Peronospora viciae*, *Pestalosphaeria concentrica*, *Pestalotia longiseta*, *Pestalotia longisetula*, *Pestalotia rhododendri*, *Pestalotiopsis*, *Pestalotiopsis adusta*, *Pestalotiopsis arachidis*, *Pestalotiopsis disseminata*, *Pestalotiopsis guepini*, *Pestalotiopsis leprogena*, *Pestalotiopsis longiseta*, *Pestalotiopsis mangiferae*, *Pestalotiopsis palmarum*, *Pestalotiopsis sydowiana*, *Pestalotiopsis theae*, *Pestalotiopsis versicolor*, *Phacidiopycnis padwickii*, *Phacidium infestans*, *Phaeochoropsis mucosa*, *Phaeocytostroma iliau*, *Phaeocytostroma sacchari*, *Phaeoisariopsis bataticola*, *Phaeolus schweinitzii*, *Phaeoramularia angolensis*, *Phaeoramularia dissiliens*, *Phaeoramularia heterospora*, *Phaeoramularia manihotis*, *Phaeoseptoria musae*, *Phaeosphaerella mangiferae*, *Phaeosphaerella theae*, *Phaeosphaeria avenaria* f. sp. *avenaria*, *Phaeosphaeria avenaria* f. sp. *triticae*, *Phaeosphaeria herpotrichoides*, *Phaeosphaeria microscopica*, *Phaeosphaeria nodorum*, *Phaeosphaeriopsis obtusispora*, *Phaeotrichoconis crotalariae*, *Phakopsora gossypii*, *Phakopsora pachyrhizi*, *Phanerochaete allantospora*, *Phanerochaete arizonica*, *Phanerochaete avellanea*, *Phanerochaete burtii*, *Phanerochaete carnosa*, *Phanerochaete chrysorhizon*, *Phanerochaete radicata*, *Phanerochaete salmonicolor*, *Phanerochaete tuberculata*, *Phanerochaete velutina*, *Phellinus ferreus*, *Phellinus gilvus*, *Phellinus igniarius*, *Phellinus pini*, *Phellinus pomaceus*, *Phellinus weirii*, *Phialophora asteris*, *Phialophora cinerescens*, *Phialophora gregata*, *Phialophora tracheiphila*, *Phloeospora multimaculans*, *Pholiota variicystis*, *Phoma*, *Phoma caricae-papayae*, *Phoma clematidina*, *Phoma costaricensis*, *Phoma cucurbitacearum*, *Phoma destructiva*, *Phoma draconis*, *Phoma eupyrena*, *Phoma exigua*, *Phoma exigua* var. *exigua*, *Phoma exigua* var. *foveata*, *Phoma exigua* var. *linicola*, *Phoma glomerata*, *Phoma glycinicola*, *Phoma herbarum*, *Phoma insidiosa*, *Phoma medicaginis*, *Phoma microspora*, *Phoma nebulosa*, *Phoma oncidii-sphacelati*, *Phoma pinodella*, *Phoma scabra*, *Phoma sclerotioides*, *Phoma strasseri*, *Phoma tracheiphila*, *Phomopsis arnoldiae*, *Phomopsis asparagi*, *Phomopsis asparagicola*, *Phomopsis azadirachtae*, *Phomopsis cannabina*, *Phomopsis caricae-papayae*, *Phomopsis coffeae*, *Phomopsis elaeagni*, *Phomopsis ganjae*, *Phomopsis javanica*, *Phomopsis lokoyae*, *Phomopsis mangiferae*, *Phomopsis obscurans*, *Phomopsis perseae*, *Phomopsis prunorum*, *Phomopsis scabra*, *Phomopsis sclerotioides*, *Phomopsis tanakae*, *Phomopsis theae*, *Photoassimilate*, *Phragmidium*, *Phragmidium mucronatum*, *Phragmidium rosae-pimpinellifoliae*, *Phragmidium rubi-idaei*, *Phragmidium violaceum*, *Phyllachora cannabis*, *Phyllachora graminis* var. *graminis*, *Phyllachora gratissima*, *Phyllachora musicola*, *Phyllachora pomigena*, *Phyllachora sacchari*, *Phyllactinia*, *Phyllactinia angulata*, *Phyllactinia guttata*, *Phyllody*, *Phyllosticta*, *Phyllosticta alliariaefoliae*, *Phyllosticta anacardiacearum*, *Phyllosticta arachidis-hypogaeae*, *Phyllosticta batatas*, *Phyllosticta capitalensis*, *Phyllosticta caricae-papayae*, *Phyllosticta carpogena*, *Phyllosticta circumscissa*, *Phyllosticta coffeicola*, *Phyllosticta concentrica*, *Phyllosticta coryli*, *Phyllosticta cucurbitacearum*, *Phyllosticta cyclaminella*, *Phyllosticta erratica*, *Phyllosticta haw aiiensis*, *Phyllosticta lentisci*, *Phyllosticta manihotis*, *Phyllosticta micropuncta*, *Phyllosticta mortonii*, *Phyllosticta nicotianae*, *Phyllosticta palmetto*, *Phyllosticta penicillariae*, *Phyllosticta perseae*, *Phyllosticta platani*, *Phyllosticta pseudocapsici*, *Phyllosticta sojaecola*, *Phyllosticta solitaria*, *Phyllosticta theae*, *Phyllosticta theicola*, *Phymatotrichopsis omnivora*, *Physalospora abdita*, *Physalospora disrupta*, *Physalospora perseae*, *Physarum cinereum*, *Physoderma alfalfae*, *Physoderma leproides*, *Physoderma trifolii*, *Physopella ampelopsidis*, *Phytophthora*, *Phytophthora alni*, *Phytophthora boehmeriae*, *Phytophthora cactorum*, *Phytophthora cajani*, *Phytophthora cambivora*, *Phytophthora capsici*, *Phytophthora cinnamomi*, *Phytophthora citricola*, *Phytophthora citrophthora*, *Phytophthora cryptogea*, *Phytophthora drechsleri*, *Phytophthora erythroseptica*, *Phytophthora fragariae*, *Phytophthora fragariae* var. *rubi*, *Phytophthora gallica*, *Phytophthora hibernalis*, *Phytophthora infestans*, *Phytophthora inflata*, *Phytophthora iranica*, *Phytophthora katsurae*, *Phytophthora kernoviae*, *Phytophthora lateralis*, *Phytophthora medicaginis*, *Phytophthora megakarya*, *Phytophthora megasperma*, *Phytophthora nicotianae*, *Phytophthora palmivora*, *Phytophthora phaseoli*, *Phytophthora plurivora*, *Phytophthora ramorum*, *Phytophthora sojae*, *Phytophthora syringae*, *Phytophthora tentaculata*, *Phytoplasma*, *Pichia membranifaciens*, *Pichia subpelliculosa*, *Pileolaria terebinthi*, *Pilidiella quercicola*, *Plasmodiophora brassicae*, *Plasmopara*, *Plasmopara halstedii*, *Plasmopara helianthi* f. *helianthi*, *Plasmopara lactucae-radicis*, *Plasmopara nivea*, *Plasmopara obducens*, *Plasmopara penniseti*, *Plasmopara pygmaea*, *Plasmopara viticola*, *Platychora ulmi*, *Plenodomus destruens*, *Plenodomus meliloti*, *Pleochaeta*, *Pleosphaerulina sojicola*, *Pleospora alfalfae*, *Pleospora betae*, *Pleospora herbarum*, *Pleospora lycopersici*, *Pleospora tarda*, *Pleospora theae*, *Pleurotus dryinus*, *Podosphaera*, *Podosphaera clandestina* var. *clandestine*, *Podosphaera fusca*, *Podosphaera leucotri-* cha, *Podosphaera macularis*, *Podosphaera pannosa*, *Podosphaera tridactyla*, *Podosphaera tridactyla* var. *tridactyla*, *Podosphaera xanthii*, *Polymyxa graminis*, *Polyscytalum pustulans*, *Polystigma fulvum*, *Poria hypobrunnea*, *Postia tephroleuca*, Potato cyst nematode, *Pratylenchus alleni*, *Pratylenchus brachyurus*, *Pratylenchus coffeae*, *Pratylenchus crenatus*, *Pratylenchus dulscus*, *Pratylenchus fallax*, *Pratylenchus flakkensis*, *Pratylenchus goodeyi*, *Pratylenchus hexincisus*, *Pratylenchus loosi*, *Pratylenchus minutus*, *Pratylenchus mulchandi*, *Pratylenchus musicola*, *Pratylenchus neglectus*, *Pratylenchus penetrans*, *Pratylenchus pratensis*, *Pratylenchus reniformia*, *Pratylenchus scribneri*, *Pratylenchus thornei*, *Pratylenchus vulnus*, *Pratylenchus zeae*, *Pseudocercospora*, *Pseudocercospora arecacearum*, *Pseudocercospora cannabina*, *Pseudocercospora fuligena*, *Pseudocercospora gunnerae*, *Pseudocercospora kaki*, *Pseudocercospora mali*, *Pseudocercospora pandoreae*, *Pseudocercospora puderi*, *Pseudocercospora purpurea*, *Pseudocercospora rhapisicola*, *Pseudocercospora subsessilis*, *Pseudocercospora theae*, *Pseudocercospora vitis*, *Pseudocercosporella capsellae*, *Pseudocochliobolus eragrostidis*, *Pseudoepicoccum cocos*, *Pseudomonas amygdali*, *Pseudomonas asplenii*, *Pseudomonas avellanae*, *Pseudomonas caricapapayae*, *Pseudomonas cichorii*, *Pseudomonas coronafaciens*, *Pseudomonas corrugate*, *Pseudomonas ficuserectae*, *Pseudomonas flavescens*, *Pseudomonas fuscovaginae*, *Pseudomonas helianthi*, *Pseudomonas marginalis*, *Pseudomonas meliae*, *Pseudomonas oryzihabitans*, *Pseudomonas palleroniana*, *Pseudomonas papaveris*, *Pseudomonas salomonii*, *Pseudomonas savastanoi*, *Pseudomonas syringae*, *Pseudomonas tomato*, *Pseudomonas tremae*, *Pseudomonas turbinellae*, *Pseudomonas viridiflava*, *Pseudoperonospora cannabina*, *Pseudoperonospora cubensis*, *Pseudoperonospora humuli*, *Pseudopezicula tetraspora*, *Pseudopezicula tracheiphila*, *Pseudopeziza jonesii*, *Pseudopeziza medicaginis*, *Pseudopeziza trifolii*, *Pseudoseptoria donacis*, *Puccinia*, *Puccinia angustata*, *Puccinia arachidis*, *Puccinia aristidae*, *Puccinia asparagi*, *Puccinia cacabata*, *Puccinia campanulae*, *Puccinia carthami*, *Puccinia coronate*, *Puccinia coronata* var. *hordei*, *Puccinia dioicae*, *Puccinia erianthi*, *Puccinia extensicola* var. *hieraciata*, *Puccinia helianthi*, *Puccinia hordei*, *Puccinia jaceae* var. *solstitialis*, *Puccinia kuehnii*, *Puccinia mariae-wilsoniae*, *Puccinia melanocephala*, *Puccinia menthae*, *Puccinia pelargonii-zonalis*, *Puccinia pittieriana*, *Puccinia poarum*, *Puccinia psidii*, *Puccinia purpurea*, *Puccinia recondita*, *Puccinia schedonnardii*, *Puccinia sessilis*, *Puccinia striiformis* f. sp. *hordei*, *Puccinia striiformis* var. *striiformis*, *Puccinia subnitens*, *Puccinia substriata* var. *indica*, *Puccinia verruca*, *Puccinia xanthii*, *Pucciniaceae*, *Pucciniastrum*, *Pucciniastrum americanum*, *Pucciniastrum arcticum*, *Pucciniastrum coryli*, *Pucciniastrum epilobii*, *Pucciniastrum hydrangeas*, *Punctodera chalcoensis*, *Pycnoporus cinnabarinus*, *Pycnoporus sanguineus*, *Pycnostysanus azaleae*, *Pyrenochaeta lycopersici*, *Pyrenochaeta terrestris*, *Pyrenopeziza brassicae*, *Pyrenophora*, *Pyrenophora avenae*, *Pyrenophora chaetomioides*, *Pyrenophora graminea*, *Pyrenophora seminiperda*, *Pyrenophora teres*, *Pyrenophora teres* f. *maculata*, *Pyrenophora teres* f. *teres*, *Pyrenophora tritici-repentis*, *Pythiaceae*, *Pythiales*, *Pythium*, *Pythium acanthicum*, *Pythium aphanidermatum*, *Pythium aristosporum*, *Pythium arrhenomanes*, *Pythium buismaniae*, *Pythium debaryanum*, *Pythium deliense*, *Pythium dissotocum*, *Pythium graminicola*, *Pythium heterothallicum*, *Pythium hypogynum*, *Pythium irregulare*, *Pythium iwayamae*, *Pythium mastophorum*, *Pythium middletonii*, *Pythium myriotylum*, *Pythium okanoganense*, *Pythium paddicum*, *Pythium paroecandrum*, *Pythium perniciosum*, *Pythium rostratum*, *Pythium scleroteichum*, *Pythium spinosum*, *Pythium splendens*, *Pythium sulcatum*, *Pythium sylvaticum*, *Pythium tardicrescens*, *Pythium tracheiphilum*, *Pythium ultimum*, *Pythium ultimum* var. *ultimum*, *Pythium vexans*, *Pythium violae*, *Pythium volutum*, *Quinisulcius acutus*, *Quinisulcius capitatus*, *Radopholous similis*, *Radopholus similis*, *Ralstonia solanacearum*, *Ramichloridium musae*, *Ramularia*, *Ramularia beticola*, *Ramularia brunnea*, *Ramularia coryli*, *Ramularia cyclaminicola*, *Ramularia macrospora*, *Ramularia menthicola*, *Ramularia necator*, *Ramularia primulae*, *Ramularia spinaciae*, *Ramularia subtilis*, *Ramularia tenella*, *Ramulispora sorghi*, *Ramulispora sorghicola*, *Resinicium bicolor*, *Rhabdocline pseudotsugae*, *Rhabdocline weirii* *Rhabdoviridae*, *Rhinocladium corticola*, *Rhizoctonia*, *Rhizoctonia leguminicola*, *Rhizoctonia rubi*, *Rhizoctonia solani*, *Rhizomorpha subcorticalis*, *Rhizophydium graminis*, *Rhizopus arrhizus*, *Rhizopus circinans*, *Rhizopus microsporus* var. *microspores*, *Rhizopus oryzae*, *Rhodococcus fascians*, *Rhynchosporium*, *Rhynchosporium secalis*, *Rhytidhysteron rufulum*, *Rhytisma acerinum*, *Rhytisma vitis*, *Rigidoporus lineatus*, *Rigidoporus microporus*, *Rigidoporus ulmarius*, *Rigidoporus vinctus*, *Rosellinia arcuata*, *Rosellinia bunodes*, *Rosellinia necatrix*, *Rosellinia pepo*, *Rosellinia subiculata*, *Rotylenchulus*, *Rotylenchulus parvus*, *Rotylenchulus reniformis*, *Rotylenchus brachyurus*, *Rotylenchus robustus*, *Saccharicola taiwanensis*, *Saccharomyces florentinus*, *Saccharomyces kluyveri*, *Sarocladium oryzae*, *Saw adaea*, *Saw adaea tulasnei*, *Schiffnerula cannabis*, *Schizoparme straminea*, *Schizophyllum commune*, *Schizopora flavipora*, *Schizothyrium pomi*, *Scleroderris canker*, *Sclerophthora macrospora*, *Sclerophthora rayssiae*, *Sclerospora graminicola*, *Sclerospora mischanthi*, *Sclerotinia borealis*, *Sclerotinia minor*, *Sclerotinia ricini*, *Sclerotinia sclerotiorum*, *Sclerotinia spermophila*, *Sclerotinia trifoliorum*, *Sclerotium*, *Sclerotium cinnamomi*, *Sclerotium delphinii*, *Scutellonema brachyurum*, *Scutellonema cavenessi*, *Scytinostroma galactinum*, *Seimatosporium mariae*, *Seimatosporium rhododendri*, *Selenophoma linicola*, *Septobasidium*, *Septobasidium bogoriense*, *Septobasidium pilosum*, *Septobasidium pseudopedicellatum*, *Septobasidium theae*, *Septocyta ruborum*, *Septogloeum potentillae*, *Septoria*, *Septoria aciculosa*, *Septoria ampelina*, *Septoria azalea*, *Septoria bataticola*, *Septoria campanulae*, *Septoria cannabis*, *Septoria caryae*, *Septoria citri*, *Septoria cucurbitacearum*, *Septoria darrowii*, *Septoria dianthi*, *Septoria eumusae*, *Septoria fragariae*, *Septoria fragariaecola*, *Septoria glycines*, *Septoria helianthi*, *Septoria humuli*, *Septoria hydrangeas*, *Septoria lactucae*, *Septoria liquidambaris*, *Septoria lycopersici*, *Septoria lycopersici* var. *malagutii*, *Septoria menthae*, *Septoria ostryae*, *Septoria passerinii*, *Septoria pisi*, *Septoria pistaciae*, *Septoria platanifolia*, *Septoria rhododendri*, *Septoria secalis*, *Septoria selenophomoides*, *Setosphaeria rostrata*, *Setosphaeria turcica*, *Sirosporium diffusum*, *Sparassis*, *Sphaceloma*, *Sphaceloma arachidis*, *Sphaceloma coryli*, *Sphaceloma menthae*, *Sphaceloma perseae*, *Sphaceloma poinsettiae*, *Sphaceloma pyrinum*, *Sphaceloma randii*, *Sphaceloma sacchari*, *Sphaceloma theae*, *Sphacelotheca reiliana*, *Sphaerella platanifolia*, *Sphaeropsis tumefaciens*, *Sphaerotheca*, *Sphaerotheca castagnei*, *Sphaerotheca fitliginea*, *Sphaerulina oryzina*, *Sphaerulina rehmiana*, *Sphaerulina rubi*, *Sphenospora kevorkianii*, *Spiniger meineckellus*, *Spiroplasma*, *Spongipellis unicolor*, *Sporisorium cruentum*, *Sporisorium ehrenbergi*, *Sporisorium scitamineum*, *Sporisorium sorghi*, *Sporonema phacidioides*, *Stagonospora avenae* f. sp. *triticae*, *Stagonospora meliloti*, *Stagonospora recedens*, *Stagonospora sac-

*chari, Stagonospora tainanensis, Steccherinum ochraceum, Stegocintractia junci, Stegophora ulmea, Stemphylium alfalfa, Stemphylium bolickii, Stemphylium cannabinum, Stemphylium globuliferum, Stemphylium lycopersici, Stemphylium sarciniforme, Stemphylium solani, Stemphylium vesicarium, Stenella anthuriicola, Stereum, Stereum hirsutum, Stereum rameale, Stereum sanguinolentum, Stigmatomycosis, Stigmella platani-racemosae, Stigmina carpophila, Stigmina liquidambaris, Stigmina palmivora, Stigmina platani, Stigmina platani-racemosae, Subanguina radicicola, Subanguina wevelli, Sydowia polyspora, Sydowiella depressula, Sydowiellaceae, Synchytrium endobioticum, Synchytrium fragariae, Synchytrium liquidambaris, Taiwanofungus camphoratus, Tapesia acuformis, Tapesia yallundae, Taphrina aurea, Taphrina bullata, Taphrina caerulescens, Taphrina coryli, Taphrina deformans, Taphrina entomospora, Taphrina johansonii, Taphrina potentillae, Taphrina ulmi, Taphrina wiesneri, Thanatephorus cucumeris, Thielaviopsis, Thielaviopsis basicola, Thyrostroma compactum, Tilletia barclayana, Tilletia caries, Tilletia controversa, Tilletia laevis, Tilletia tritici, Tilletia walkeri, Tilletiariaceae, Tobacco necrosis virus, Togniniaceae, Trachysphaera fructigena, Trametes gibbosa, Trametes hirsute, Trametes nivosa, Trametes pubescens, Tranzschelia discolor* f. sp. *persica, Tranzschelia pruni-spinosae* var. *discolor, Trichaptum biforme, Trichoderma harzianum, Trichoderma koningii, Trichoderma viride, Trichothecium roseum, Tripospermum acerinum, Truncatella, Truncatella laurocerasi, Tubercularia lateritia, Tubercularia ulmea, Tubeufia pezizula, Tunstallia aculeata, Tylenchorhynchus, Tylenchorhynchus brevilineatus, Tylenchorhynchus claytoni, Tylenchorhynchus dubius, Tylenchorhynchus maximus, Tylenchorhynchus nudus, Tylenchorhynchus phaseoli, Tylenchorhynchus vulgaris, Tylenchorhynchus zeae, Tylenchulus semipenetrans, Typhula idahoensis, Typhula incarnate, Typhula ishikariensis, Typhula ishikariensis* var. *canadensis, Typhula variabilis, Typhulochaeta, Tyromyces calkinsii, Tyromyces chioneus, Tyromyces galactinus, Ulocladium atrum, Ulocladium consortiale, Uncinula, Uncinula macrospora, Uncinula necator, Uredo behnickiana, Uredo kriegeriana, Uredo musae, Uredo nigropuncta, Uredo rangelii, Urocystis, Urocystis agropyri, Urocystis brassicae, Urocystis occulta, Uromyces, Uromyces apiosporus, Uromyces beticola, Uromyces ciceris-arietini, Uromyces dianthi, Uromyces euphorbiae, Uromyces graminis, Uromyces inconspicuus, Uromyces lineolatus* subsp. *nearcticus, Uromyces medicaginis, Uromyces musae, Uromyces oblongus, Uromyces pisi-sativi, Uromyces proeminens* var. *poinsettiae, Uromyces trifolii-repentis* var. *fallens, Uromyces viciae-fabae* var. *viciae-fabae, Urophlyctis leproides, Urophlyctis trifolii, Urophora cardui, Ustilaginales, Ustilaginoidea virens, Ustilaginomycetes, Ustilago, Ustilago avenae, Ustilago hordei, Ustilago maydis, Ustilago nigra, Ustilago nuda, Ustilago scitaminea, Ustilago tritici, Valsa abietis, Valsa ambiens, Valsa auerswaldii, Valsa ceratosperma, Valsa kunzei, Valsa nivea, Valsa sordida, Valsaria insitiva, Venturia carpophila, Venturia inaequalis, Venturia pirina, Venturia pyrina, Veronaea musae, Verticillium, Verticillium albo-atrum, Verticillium albo-atrum* var. *menthae, Verticillium dahliae, Verticillium longisporum, Verticillium theobromas, Villosiclava virens, Virescence, Waitea circinata, Wuestneiopsis Georgiana, Xanthomonas ampelina, Xanthomonas axonopodis, Xanthomonas campestris, Xanthomonas campestris* pv. *campestris, Xanthomonas oryzae, Xeromphalina fraxinophila, Xiphinema americanum, Xiphinema bakeri, Xiphinema brevicolle, Xiphinema diversicaudatum, Xiphinema insigne, Xiphinema rivesi, Xiphinema vuittenezi, Xylaria mali, Xylaria polymorpha, Xylella fastidiosa, Xylophilus, Xylophilus ampelinus, Zopfia rhizophila, Zygosaccharomyces bailiff,* and *Zygosaccharomyces florentinus.*

Root Binding Proteins and Peptides

The invention also relates to fusion proteins comprising a targeting sequence and at least one root binding protein or peptide. The root binding protein or peptide can be any protein or peptide that is capable of specifically or non-specifically binding to a plant root.

Suitable root binding proteins and peptides include adhesins (e.g., rhicadhesin), flagellins, omptins, lectins, pilus proteins, curlus proteins, intimins, invasins, agglutinins, and afimbrial proteins.

Recombinant *Bacillus cereus* Family Members that Express the Fusion Proteins

The present invention also relates to a recombinant *Bacillus cereus* family member that expresses a fusion protein. The fusion protein can be any of the fusion proteins discussed above.

The recombinant *Bacillus cereus* family member can coexpress two or more of any of the fusion proteins discussed above. For example, the recombinant *Bacillus cereus* family member can coexpress at least one fusion protein that comprises a root binding protein or peptide, together with at least one fusion protein comprising a plant growth stimulating protein or peptide or at least one fusion protein comprising a protein or peptide that protects a plant from a pathogen.

The recombinant *Bacillus cereus* family member can comprise *Bacillus anthracis, Bacillus cereus, Bacillus thuringiensis, Bacillus mycoides, Bacillus pseudomycoides, Bacillus weihenstephensis*, or a combination thereof.

To generate a recombinant *Bacillus cereus* family member expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. The recombinant *Bacillus cereus* family member can then exposed to conditions which will induce sporulation. Suitable conditions for inducing sporulation are known in the art. For example, the recombinant *Bacillus cereus* family member can be plated onto agar plates, and incubated at a temperature of about 30° C. for several days (e.g., 3 days).

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family spores expressing the fusion protein have been generated, they can be inactivated to prevent further germination once in use. Any method for inactivating bacterial spores that is known in the art can be used. Suitable methods include, without limitation, UV exposure, heat treatment, and irradiation. Alternatively, spores derived from nontoxigenic strains, or genetically or physically inactivated strains, can be used.

Formulations

The present invention also relates to formulations comprising any of the recombinant *Bacillus cereus* family members discussed in the preceding section and an agriculturally acceptable carrier.

The agriculturally acceptable carrier can be any carrier suitable for agricultural use. For example, suitable agriculturally acceptable carriers include, but are not limited to dispersants, surfactants, additives, water, thickeners, anti-caking agents, residue breakdown, composting formulations, granular applications, diatomaceous earth, oils, coloring agents, stabilizers, preservatives, polymers, coatings, and combinations thereof.

The additive can comprise an oil, a gum, a resin, a clay, a polyoxyethylene glycol, a terpene, a viscid organic, a fatty acid ester, a sulfated alcohol, an alkyl sulfonate, a petroleum sulfonate, an alcohol sulfate, a sodium alkyl butane diamate, a polyester of sodium thiobutane dioate, a benzene acetonitrile derivative, a proteinaceous material (e.g., a milk product, wheat flour, soybean meal, blood, albumin, gelatin, or a combination thereof), or a combination thereof.

The thickener can comprise a long chain alkylsulfonate of polyethylene glycol, a polyoxyethylene oleate, or a combination thereof.

The surfactant can comprise a heavy petroleum oil, a heavy petroleum distillate, a polyol fatty acid ester, a polyethoxylated fatty acid ester, an aryl alkyl polyoxyethylene glycol, an alkyl amine acetate, an alkyl aryl sulfonate, a polyhydric alcohol, an alkyl phosphate, or a combination thereof.

The anti-caking agent comprises a sodium salt, a calcium carbonate, a sodium sulfite, a sodium sulfate, diatomaceous earth, or a combination thereof. For example, the sodium salt can comprise a sodium salt of monomethyl naphthalene sulfonate, a sodium salt of dimethyl naphthalene sulfonate, or a combination thereof.

Suitable agriculturally acceptable carriers include vermiculite, charcoal, sugar factory carbonation press mud, rice husk, carboxymethyl cellulose, peat, perlite, fine sand, calcium carbonate, flour, alum, a starch, talc, polyvinyl pyrrolidone, or a combination thereof.

The formulation can comprise a seed coating formulation, a liquid formulation for application to plants or to a plant growth medium, or a solid formulation for application to plants or to a plant growth medium.

For example, the seed coating formulation can comprise an aqueous or oil-based solution for application to seeds. Alternatively, the seed coating formulation can comprise a powder or granular formulation for application to seeds.

The liquid formulation for application to plants or to a plant growth medium can comprise a concentrated formulation or a working form formulation.

The solid formulation for application to plants or to a plant growth medium can comprises a granular formulation or a powder agent.

Any of the above formulations can also comprise an agrochemical, for example, a fertilizer, a micronutrient fertilizer material, an insecticide, a herbicide, a plant growth amendment, a fungicide, an insecticide, a molluscicide, an algicide, a bacterial inoculant, a fungal inoculant, or a combination thereof.

The fertilizer can comprise a liquid fertilizer.

The fertilizer can comprise ammonium sulfate, ammonium nitrate, ammonium sulfate nitrate, ammonium chloride, ammonium bisulfate, ammonium polysulfide, ammonium thiosulfate, aqueous ammonia, anhydrous ammonia, ammonium polyphosphate, aluminum sulfate, calcium nitrate, calcium ammonium nitrate, calcium sulfate, calcined magnesite, calcitic limestone, calcium oxide, calcium nitrate, dolomitic limestone, hydrated lime, calcium carbonate, diammonium phosphate, monoammonium phosphate, magnesium nitrate, magnesium sulfate, potassium nitrate, potassium chloride, potassium magnesium sulfate, potassium sulfate, sodium nitrates, magnesian limestone, magnesia, urea, urea-formaldehydes, urea ammonium nitrate, sulfur-coated urea, polymer-coated urea, isobutylidene diurea, $K_2SO_4$-$2MgSO_4$, kainite, sylvinite, kieserite, Epsom salts, elemental sulfur, marl, ground oyster shells, fish meal, oil cakes, fish manure, blood meal, rock phosphate, super phosphates, slag, bone meal, wood ash, manure, bat guano, peat moss, compost, green sand, cottonseed meal, feather meal, crab meal, fish emulsion, or a combination thereof.

The micronutrient fertilizer material can comprise boric acid, a borate, a boron frit, copper sulfate, a copper frit, a copper chelate, a sodium tetraborate decahydrate, an iron sulfate, an iron oxide, iron ammonium sulfate, an iron frit, an iron chelate, a manganese sulfate, a manganese oxide, a manganese chelate, a manganese chloride, a manganese frit, a sodium molybdate, molybdic acid, a zinc sulfate, a zinc oxide, a zinc carbonate, a zinc frit, zinc phosphate, a zinc chelate, or a combination thereof.

The insecticide can comprise an organophosphate, a carbamate, a pyrethroid, an acaricide, an alkyl phthalate, boric acid, a borate, a fluoride, sulfur, a haloaromatic substituted urea, a hydrocarbon ester, a biologically-based insecticide, or a combination thereof.

The herbicide can comprise a chlorophenoxy compound, a nitrophenolic compound, a nitrocresolic compound, a dipyridyl compound, an acetamide, an aliphatic acid, an anilide, a benzamide, a benzoic acid, a benzoic acid derivative, anisic acid, an anisic acid derivative, a benzonitrile, benzothiadiazinone dioxide, a thiocarbamate, a carbamate, a carbanilate, chloropyridinyl, a cyclohexenone derivative, a dinitroaminobenzene derivative, a fluorodinitrotoluidine compound, isoxazolidinone, nicotinic acid, isopropylamine, an isopropylamine derivatives, oxadiazolinone, a phosphate, a phthalate, a picolinic acid compound, a triazine, a triazole, a uracil, a urea derivative, endothall, sodium chlorate, or a combination thereof.

The fungicide can comprise a substituted benzene, a thiocarbamate, an ethylene bis dithiocarbamate, a thiophthalidamide, a copper compound, an organomercury compound, an organotin compound, a cadmium compound, anilazine, benomyl, cyclohexamide, dodine, etridiazole, iprodione, metlaxyl, thiamimefon, triforine, or a combination thereof.

The fungal inoculant can comprise a fungal inoculant of the family Glomeraceae, a fungal inoculant of the family Claroidoglomeraceae, a fungal inoculant of the family Gigasporaceae, a fungal inoculant of the family Acaulosporaceae, a fungal inoculant of the family Sacculosporaceae, a fungal inoculant of the family Entrophosporaceae, a fungal inoculant of the family Pacidsporaceae, a fungal inoculant of the family Diversisporaceae, a fungal inoculant of the family Paraglomeraceae, a fungal inoculant of the family Archaeosporaceae, a fungal inoculant of the family Geosiphonaceae, a fungal inoculant of the family Ambisporaceae, a fungal inoculant of the family Scutellosporaceae, a fungal inoculant of the family Dentiscultataceae, a fungal inoculant of the family Racocetraceae, a fungal inoculant of the phylum Basidiomycota, a fungal inoculant of the phylum Ascomycota, a fungal inoculant of the phylum Zygomycota, or a combination thereof.

The bacterial inoculant can comprise a bacterial inoculant of the genus *Rhizobium*, a bacterial inoculant of the genus *Bradyrhizobium*, a bacterial inoculant of the genus *Mesorhizobium*, a bacterial inoculant of the genus *Azorhizobium*, a bacterial inoculant of the genus *Allorhizobium*, a bacterial inoculant of the genus *Sinorhizobium*, a bacterial inoculant of the genus *Kluyvera*, a bacterial inoculant of the genus *Azotobacter*, a bacterial inoculant of the genus

*Pseudomonas*, a bacterial inoculant of the genus *Azospirillium*, a bacterial inoculant of the genus *Bacillus*, a bacterial inoculant of the genus *Streptomyces*, a bacterial inoculant of the genus *Paenibacillus*, a bacterial inoculant of the genus *Paracoccus*, a bacterial inoculant of the genus *Enterobacter*, a bacterial inoculant of the genus *Alcaligenes*, a bacterial inoculant of the genus *Mycobacterium*, a bacterial inoculant of the genus *Trichoderma*, a bacterial inoculant of the genus *Gliocladium*, a bacterial inoculant of the genus *Glomus*, a bacterial inoculant of the genus *Klebsiella*, or a combination thereof.

Methods for Promoting Plant Growth

The present invention also relates to methods for stimulating plant growth. The method for stimulating plant growth comprises introducing into a plant growth medium any of the recombinant *Bacillus cereus* family members discussed above or any of the formulations discussed above. Alternatively, any of the recombinant *Bacillus cereus* family members discussed above or any of the formulations discussed above can be applied to the foliage of a plant, to a plant seed, or to an area surrounding a plant. In such methods, the plant growth stimulating protein or peptide is physically attached to the exosporium of the recombinant *Bacillus* family member.

Alternatively, the method for stimulating plant growth comprises introducing a recombinant *Bacillus cereus* family member expressing a fusion protein into a plant growth medium or applying a recombinant *Bacillus cereus* family member expressing a fusion protein to foliage of a plant, a plant seed, or an area surrounding a plant. The fusion protein comprises at least one plant growth stimulating protein or peptide and a targeting sequence. The targeting sequence can be any of the targeting sequences discussed herein.

The plant growth stimulating protein can comprise an enzyme. For example, the enzyme can comprise an enzyme that degrades or modifies a bacterial, fungal, or plant nutrient source. Such enzymes include cellulases, lipases, lignin oxidases, proteases, glycoside hydrolases, phosphatases, nitrogenases, and nucleases.

Suitable cellulases include endocellulases (e.g., a *Bacillus subtilis* endoglucanase, a *Bacillus thuringiensis* endoglucanase, a *Bacillus cereus* endoglucanase, or a *Bacillus clausii* endoglucanase), exocellulases (e.g., a *Trichoderma reesei* exocellulase), and β-glucosidases (e.g., a *Bacillus subtilis* β-glucosidase, a *Bacillus thuringiensis* β-glucosidase, a *Bacillus cereus* β-glucosidase, or a *Bacillus clausii* β-glucosidase).

The lipase can comprise a *Bacillus subtilis* lipase, a *Bacillus thuringiensis* lipase, a *Bacillus cereus* lipase, or a *Bacillus clausii* lipase.

Suitable lignin oxidases comprise lignin peroxidases, laccases, glyoxal oxidases, liginases, and manganese peroxidases.

The protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

The phosphatase can comprise a phosphoric monoester hydrolase, a phosphomonoesterase, a phosphoric diester hydrolase, a phosphodiesterase, a triphosphoric monoester hydrolase, a phosphoryl anhydride hydrolase, a pyrophosphatase, a phytase, a trimetaphosphatase, or a triphosphatase.

The nitrogenase can comprise a Nif family nitrogenase.

In any of the above methods for stimulating plant growth, plants grown in the plant growth medium comprising the recombinant *Bacillus cereus* family member exhibit increased growth as compared to the growth of plants in the identical plant growth medium that does not contain the recombinant *Bacillus cereus* family member.

Methods for Protecting a Plant from a Pathogen

The present invention further relates to methods for protecting a plant from a pathogen. Such methods comprise introducing any of the recombinant *Bacillus cereus* family members discussed above or any of the formulations discussed above into a plant growth medium. Alternatively, such methods comprise applying any of the recombinant *Bacillus cereus* family members discussed above or any of the formulations discussed above to foliage of a plant, to a plant seed, or to an area surrounding a plant. In these methods, the protein or peptide that protects a plant from a pathogen is physically attached to the exosporium of the recombinant *Bacillus cereus* family member.

Plants grown in the plant growth medium comprising the recombinant *Bacillus cereus* family member are less susceptible to infection with the pathogen as compared to plants grown in the identical plant growth medium that does not contain the recombinant *Bacillus cereus* family member.

Methods for Immobilizing *Bacillus* Spores on a Root System

The present invention is also directed to methods for immobilizing a recombinant *Bacillus cereus* family member spore on a root system of a plant. These methods comprise introducing any of the recombinant *Bacillus cereus* family members discussed above or any of the formulations discussed above into a plant growth medium. Alternatively, such methods comprise applying any of the recombinant *Bacillus cereus* family members discussed above or any of the formulations discussed above to foliage of a plant, to a plant seed, or to an area surrounding a plant. The root binding protein or peptide is physically attached to the exosporium of the recombinant *Bacillus* family member.

These methods allow the *Bacillus cereus* family member spore to bind to a root of a plant, such that the spore is maintained at the plant's root structure instead of dissipating into the plant growth medium.

In any of the methods for immobilizing a recombinant *Bacillus cereus* family member spore on a root system of a plant, the root binding protein or peptide can selectively target and maintain the *Bacillus cereus* family member at plant roots and substructures of plant roots.

Plant Growth Medium

In any of the above methods, the plant growth medium is material that is capable of supporting the growth of a plant. The plant growth medium can comprise soil, water, an aqueous solution, sand, gravel, a polysaccharide, mulch, compost, peat moss, straw, logs, clay, soybean meal, yeast extract, or a combination thereof. For example, the plant growth medium comprises soil, compost, peat moss, or a combination thereof.

The plant growth medium can optionally be supplemented with a substrate for an enzyme. For example, the substrate can comprise tryptophan, an adenosine monophosphate, an adenosine diphosphate, an adenosine triphosphate (e.g., adenosine-3-triphosphate), indole, a trimetaphosphate, ferrodoxin, acetoin, diacetyl, pyruvate, acetolactate, or a combination thereof.

Application Methods

In any of the above methods, the recombinant *Bacillus cereus* family member or formulation can be introduced into the plant growth medium or applied to foliage of a plant, to a plant seed, or to an area surrounding a plant.

For example, the method can comprise coating seeds with the recombinant *Bacillus cereus* family member or a formulation containing the recombinant *Bacillus cereus* family member prior to planting.

Alternatively, the method can comprise applying the recombinant *Bacillus cereus* family member or formulation to plant foliage.

The method can comprise introducing the recombinant *Bacillus cereus* family member into the plant growth medium by applying a liquid or solid formulation containing the recombinant *Bacillus cereus* family member to the medium (e.g., soil, compost, peat moss, or a combination thereof).

The formulation can be applied to the plant growth medium prior to, concurrently with, or after planting of seeds, seedlings, cuttings, bulbs, or plants in the plant growth medium.

Co-Application of Agrochemicals.

Any of the above methods can further comprise introducing at least one agrochemical into the plant growth medium or applying at least one agrochemical to plants or seeds. The agrochemical can be any of those listed above for inclusion in the formulations, or any combination thereof.

Plants

The above methods can be practiced with a variety of plants. For example, the plant can be a dicotyledon, a monocotyledon, or a gymnosperm.

For example, where the plant is a dicotyledon, the dicotyledon can be selected from the group consisting of bean, pea, tomato, pepper, squash, alfalfa, almond, aniseseed, apple, apricot, arracha, artichoke, avocado, bambara groundnut, beet, bergamot, black pepper, black wattle, blackberry, blueberry, bitter orange, bok-choi, Brazil nut, breadfruit, broccoli, broad bean, Brussels sprouts, buckwheat, cabbage, camelina, Chinese cabbage, cacao, cantaloupe, caraway seeds, cardoon, carob, carrot, cashew nuts, cassava, castor bean, cauliflower, celeriac, celery, cherry, chestnut, chickpea, chicory, chili pepper, chrysanthemum, cinnamon, citron, clementine, clove, clover, coffee, cola nut, colza, corn, cotton, cottonseed, cowpea, crambe, cranberry, cress, cucumber, currant, custard apple, drumstick tree, earth pea, eggplant, endive, fennel, fenugreek, fig, filbert, flax, geranium, gooseberry, gourd, grape, grapefruit, guava, hemp, hempseed, henna, hop, horse bean, horseradish, indigo, jasmine, Jerusalem artichoke, jute, kale, kapok, kenaf, kohlrabi, kumquat, lavender, lemon, lentil, lespedeza, lettuce, lime, liquorice, litchi, loquat, lupine, macadamia nut, mace, mandarin, mangel, mango, medlar, melon, mint, mulberry, mustard, nectarine, niger seed, nutmeg, okra, olive, opium, orange, papaya, parsnip, pea, peach, peanut, pear, pecan nut, persimmon, pigeon pea, pistachio nut, plantain, plum, pomegranate, pomelo, poppy seed, potato, sweet potato, prune, pumpkin, quebracho, quince, trees of the genus *Cinchona*, quinoa, radish, ramie, rapeseed, raspberry, rhea, rhubarb, rose, rubber, rutabaga, safflower, sainfoin, salsify, sapodilla, Satsuma, scorzonera, sesame, shea tree, soybean, spinach, squash, strawberry, sugar beet, sugarcane, sunflower, swede, sweet pepper, tangerine, tea, teff, tobacco, tomato, trefoil, tung tree, turnip, urena, vetch, walnut, watermelon, yerba mate, wintercress, shepherd's purse, garden cress, peppercress, watercress, pennycress, star anise, laurel, bay laurel, cassia, jamun, dill, tamarind, peppermint, oregano, rosemary, sage, soursop, pennywort, calophyllum, balsam pear, kukui nut, Tahitian chestnut, basil, huckleberry, hibiscus, passionfruit, star apple, sassafras, cactus, St. John's wort, loosestrife, hawthorn, cilantro, curry plant, kiwi, thyme, zucchini, ulluco, jicama, waterleaf, spiny monkey orange, yellow mombin, starfruit, amaranth, wasabi, Japanese pepper, yellow plum, mashua, Chinese toon, New Zealand spinach, bower spinach, ugu, tansy, chickweed, jocote, Malay apple, paracress, sowthistle, Chinese potato, horse parsley, hedge mustard, campion, agate, cassod tree, thistle, burnet, star gooseberry, saltwort, glasswort, sorrel, silver lace fern, collard greens, primrose, cowslip, purslane, knotgrass, terebinth, tree lettuce, wild betel, West African pepper, yerba santa, tarragon, parsley, chervil, land cress, burnet saxifrage, honeyherb, butterbur, shiso, water pepper, perilla, bitter bean, oca, kampong, Chinese celery, lemon basil, Thai basil, water mimosa, cicely, cabbage-tree, moringa, mauka, ostrich fern, rice paddy herb, yellow sawah lettuce, lovage, pepper grass, maca, bottle gourd, hyacinth bean, water spinach, catsear, fishwort, Okinawan spinach, lotus sweetjuice, gallant soldier, culantro, arugula, cardoon, caigua, mitsuba, chipilin, samphire, mampat, ebolo, ivy gourd, cabbage thistle, sea kale, chaya, huauzontle, Ethiopian mustard, magenta spreen, good king henry, epazole, lamb's quarters, centella plumed cockscomb, caper, rapini, napa cabbage, mizuna, Chinese savoy, kai-lan, mustard greens, Malabar spinach, chard, marshmallow, climbing wattle, China jute, paprika, annatto seed, spearmint, savory, marjoram, cumin, chamomile, lemon balm, allspice, bilberry, cherimoya, cloudberry, damson, pitaya, durian, elderberry, feijoa, jackfruit, jambul, jujube, physalis, purple mangosteen, rambutan, redcurrant, blackcurrant, salal berry, satsuma, ugli fruit, azuki bean, black bean, black-eyed pea, borlotti bean, common bean, green bean, kidney bean, lima bean, mung bean, navy bean, pinto bean, runner bean, mangetout, snap pea, broccoflower, calabrese, nettle, bell pepper, raddichio, daikon, white radish, skirret, tat soi, broccolini, black radish, burdock root, fava bean, broccoli raab, lablab, lupin, sterculia, velvet beans, winged beans, yam beans, mulga, ironweed, umbrella bush, tjuntjula, wakalpulka, witchetty bush, wiry wattle, chia, beech nut, candlenut, colocynth, mamoncillo, Maya nut, mongongo, ogbono nut, paradise nut, and cempedak.

Alternatively, the dicotyledon can be from a family selected from the group consisting of Acanthaceae (acanthus), Aceraceae (maple), Achariaceae, Achatocarpaceae (achatocarpus), Actinidiaceae (Chinese gooseberry), Adoxaceae (moschatel), Aextoxicaceae, Aizoaceae (fig marigold), Akaniaceae, Alangiaceae, Alseuosmiaceae, Alzateaceae, Amaranthaceae (amaranth), Amborellaceae, Anacardiaceae (sumac), Ancistrocladaceae, Anisophylleaceae, Annonaceae (custard apple), Apiaceae (carrot), Apocynaceae (dogbane), Aquifoliaceae (holly), Araliaceae (ginseng), Aristolochiaceae (birthwort), Asclepiadaceae (milkweed), Asteraceae (aster), Austrobaileyaceae, Balanopaceae, Balanophoraceae (balanophora), Balsaminaceae (touch-me-not), Barbeyaceae, Barclayaceae, Basellaceae (basella), Bataceae (saltwort), Begoniaceae (begonia), Berberidaceae (barberry), Betulaceae (birch), Bignoniaceae (trumpet creeper), Bixaceae (lipstick tree), Bombacaceae (kapok tree), Boraginaceae (borage), Brassicaceae (mustard, also Cruciferae), Bretschneideraceae, Brunelliaceae (brunellia), Bruniaceae, Brunoniaceae, Buddlejaceae (butterfly bush), Burseraceae (frankincense), Buxaceae (boxwood), Byblidaceae, Cabombaceae (water shield), Cactaceae (cactus), Caesalpiniaceae, Callitrichaceae (water starwort), Calycanthaceae (strawberry shrub), Calyceraceae (calycera), Campanulaceae (bellflower), Canellaceae (canella), Cannabaceae (hemp), Capparaceae (caper), Caprifoliaceae (honeysuckle), Cardiopteridaceae, Caricaceae (papaya), Caryocaraceae (souari), Caryophyllaceae (pink), Casuarinaceae (she-oak), Cecropiaceae (cecropia), Celastraceae (bittersweet), Cephalotaceae, Ceratophyllaceae (hornwort), Cercidiphyllaceae (katsura tree), Chenopodiaceae (goosefoot), Chloranthaceae (chloranthus), Chrysobalanaceae (cocoa plum), Circaeasteraceae, Cistaceae (rockrose), Clethraceae (clethra), Clusiaceae (mangosteen, also Guttiferae), Cneoraceae, Columelliaceae, Combretaceae (Indian almond), Compositae (aster), Connaraceae (cannarus), Convolvulaceae (morning glory), Coriariaceae, Cornaceae (dogwood), Corynocarpaceae (karaka), Crassulaceae (stonecrop), Crossosomataceae (crossosoma), Crypteroniaceae, Cucurbitaceae (cucumber), Cunoniaceae (cunonia), Cuscutaceae (dodder), Cyrillaceae (cyrilla), Daphniphyllaceae, Datiscaceae (datisca), Davidsoniaceae, Degeneriaceae, Dialypetalanthaceae, Diapensiaceae (diapensia), Dichapetalaceae, Didiereaceae, Didymelaceae, Dilleniaceae (dillenia), Dioncophyllaceae, Dipentodontaceae, Dipsacaceae (teasel), Dipterocarpaceae (meranti), Donatiaceae, Droseraceae (sundew), Duckeodendraceae, Ebenaceae (ebony), Elaeagnaceae (oleaster), Elaeocarpaceae (elaeocarpus), Elatinaceae (waterwort), Empetraceae (crowberry), Epacridaceae (epacris), Eremolepidaceae (catkin-mistletoe), Ericaceae (heath), Erythroxylaceae (coca), Eucommiaceae, Eucryphiaceae, Euphorbiaceae (spurge), Eupomatiaceae, Eupteleaceae, Fabaceae (pea or legume), Fagaceae (beech), Flacourtiaceae (flacourtia), Fouquieriaceae (ocotillo), Frankeniaceae (frankenia), Fumariaceae (fumitory), Garryaceae (silk tassel), Geissolomataceae, Gentianaceae (gentian), Geraniaceae (geranium), Gesneriaceae (gesneriad), Globulariaceae, Gomortegaceae, Goodeniaceae (goodenia), Greyiaceae, Grossulariaceae (currant), Grubbiaceae, Gunneraceae (gunnera), Gyrostemonaceae, Haloragaceae (water milfoil), Hamamelidaceae (witch hazel), Hernandiaceae (hernandia), Himantandraceae, Hippocastanaceae (horse chestnut), Hippocrateaceae (hippocratea), Hippuridaceae (mare's tail), Hoplestigmataceae, Huaceae, Hugoniaceae, Humiriaceae, Hydnoraceae, Hydrangeaceae (hydrangea), Hydrophyllaceae (waterleaf), Hydrostachyaceae, Icacinaceae (icacina), Idiospermaceae, Illiciaceae (star anise), Ixonanthaceae, Juglandaceae (walnut), Julianiaceae, Krameriaceae (krameria), Lacistemataceae, Lamiaceae (mint, also Labiatae), Lardizabalaceae (lardizabala), Lauraceae (laurel), Lecythidaceae (brazil nut), Leeaceae, Leitneriaceae (corkwood), Lennoaceae (lennoa), Lentibulariaceae (bladderwort), Limnanthaceae (meadow foam), Linaceae (flax), Lissocarpaceae, Loasaceae (loasa), Loganiaceae (logania), Loranthaceae (showy mistletoe), Lythraceae (loosestrife), Magnoliaceae (magnolia), Malesherbiaceae, Malpighiaceae (barbados cherry), Malvaceae (mallow), Marcgraviaceae (shingle plant), Medusagynaceae, Medusandraceae, Melastomataceae (melastome), Meliaceae (mahogany), Melianthaceae, Mendonciaceae, Menispermaceae (moonseed), Menyanthaceae (buckbean), Mimosaceae, Misodendraceae, Mitrastemonaceae, Molluginaceae (carpetweed), Monimiaceae (monimia), Monotropaceae (Indian pipe), Moraceae (mulberry), Moringaceae (horseradish tree), Myoporaceae (myoporum), Myricaceae (bayberry), Myristicaceae (nutmeg), Myrothamnaceae, Myrsinaceae (myrsine), Myrtaceae (myrtle), Nelumbonaceae (lotus lily), Nepenthaceae (East Indian pitcherplant), Neuradaceae, Nolanaceae, Nothofagaceae, Nyctaginaceae (four-o'clock), Nymphaeaceae (water lily), Nyssaceae (sour gum), Ochnaceae (ochna), Olacaceae (olax), Oleaceae (olive), Oliniaceae, Onagraceae (evening primrose), Oncothecaceae, Opiliaceae, Orobanchaceae (broom rape), Oxalidaceae (wood sorrel), Paeoniaceae (peony), Pandaceae, Papaveraceae (poppy), Papilionaceae, Paracryphiaceae, Passifloraceae (passionflower), Pedaliaceae (sesame), Pellicieraceae, Penaeaceae, Pentaphragmataceae, Pentaphylacaceae, Peridiscaceae, Physenaceae, Phytolaccaceae (pokeweed), Piperaceae (pepper), Pittosporaceae (pittosporum), Plantaginaceae (plantain), Platanaceae (plane tree), Plumbaginaceae (leadwort), Podostemaceae (river weed), Polemoniaceae (phlox), Polygalaceae (milkwort), Polygonaceae (buckwheat), Portulacaceae (purslane), Primulaceae (primrose), Proteaceae (protea), Punicaceae (pomegranate), Pyrolaceae (shinleaf), Quiinaceae, Rafflesiaceae (rafflesia), Ranunculaceae (buttercup orranunculus), Resedaceae (mignonette), Retziaceae, Rhabdodendraceae, Rhamnaceae (buckthorn), Rhizophoraceae (red mangrove), Rhoipteleaceae, Rhynchocalycaceae, Rosaceae (rose), Rubiaceae (madder), Rutaceae (rue), Sabiaceae (sabia), Saccifoliaceae, Salicaceae (willow), Salvadoraceae, Santalaceae (sandalwood), Sapindaceae (soapberry), Sapotaceae (sapodilla), Sarcolaenaceae, Sargentodoxaceae, Sarraceniaceae (pitcher plant), Saururaceae (lizard's tail), Saxifragaceae (saxifrage), Schisandraceae (schisandra), Scrophulariaceae (figwort), Scyphostegiaceae, Scytopetalaceae, Simaroubaceae (quassia), Simmondsiaceae (jojoba), Solanaceae (potato), Sonneratiaceae (sonneratia), Sphaerosepalaceae, Sphenocleaceae (spenoclea), Stackhousiaceae (stackhousia), Stachyuraceae, Staphyleaceae (bladdernut), Sterculiaceae (cacao), Stylidiaceae, Styracaceae (storax), Surianaceae (suriana), Symplocaceae (sweetleaf), Tamaricaceae (tamarix), Tepuianthaceae, Tetracentraceae, Tetrameristaceae, Theaceae (tea), Theligonaceae, Theophrastaceae (theophrasta), Thymelaeaceae (mezereum), Ticodendraceae, Tiliaceae (linden), Tovariaceae, Trapaceae (water chestnut), Tremandraceae, Trigoniaceae, Trimeniaceae, Trochodendraceae, Tropaeolaceae (nasturtium), Turneraceae (turnera), Ulmaceae (elm), Urticaceae (nettle), Valerianaceae (valerian), Verbenaceae (verbena), Violaceae (violet), Viscaceae (Christmas mistletoe), Vitaceae (grape), Vochysiaceae, Winteraceae (wintera), Xanthophyllaceae, and Zygophyllaceae (creosote bush).

Where the plant is a monocotyledon, the monocotyledon can be selected from the group consisting of corn, wheat, oat, rice, barley, millet, banana, onion, garlic, asparagus, ryegrass, millet, fonio, raishan, nipa grass, turmeric, saffron, galangal, chive, cardamom, date palm, pineapple, shallot, leek, scallion, water chestnut, ramp, Job's tears, bamboo, ragi, spotless watermeal, arrowleaf elephant ear, Tahitian spinach, abaca, areca, bajra, betel nut, broom millet, broom sorghum, citronella, coconut, cocoyam, maize, dasheen, durra, durum wheat, edo, Pique, formio, ginger, orchard grass, esparto grass, Sudan grass, guinea corn, Manila hemp, henequen, hybrid maize, jowar, lemon grass, maguey, bulrush millet, finger millet, foxtail millet, Japanese millet, proso millet, New Zealand flax, oats, oil palm, palm palmyra, sago palm, redtop, sisal, sorghum, spelt wheat, sweet corn, sweet sorghum, taro, teff, timothy grass, triticale, vanilla, wheat, and yam.

Alternatively, the monocotyledon can be from a family selected from the group consisting of Acoraceae (calamus), Agavaceae (century plant), Alismataceae (water plantain), Aloeaceae (aloe), Aponogetonaceae (cape pondweed), Araceae (arum), Arecaceae (palm), Bromeliaceae (bromeliad), Burmanniaceae (burmannia), Butomaceae (flowering rush), Cannaceae (canna), Centrolepidaceae, Commelinaceae (spiderwort), Corsiaceae, Costaceae (costus), Cyanastraceae, Cyclanthaceae (Panama hat), Cymodoceaceae (manatee grass), Cyperaceae (sedge), Dioscoreaceae (yam), Eriocaulaceae (pipewort), Flagellariaceae, Geosiridaceae, Haemodoraceae (bloodwort), Hanguanaceae (hanguana), Heliconiaceae (heliconia), Hydatellaceae, Hydrocharitaceae (tape grass), Iridaceae (iris), Joinvilleaceae (joinvillea), Juncaceae (rush), Juncaginaceae (arrow grass), Lemnaceae (duckweed), Liliaceae (lily), Limnocharitaceae (water poppy), Lowiaceae, Marantaceae (prayer plant), Mayacaceae (mayaca), Musaceae (banana), Najadaceae (water nymph), Orchidaceae (orchid), Pandanaceae (screw pine), Petrosaviaceae, Philydraceae (philydraceae), Poaceae (grass), Pontederiaceae (water hyacinth), Posidoniaceae (posidonia), Potamogetonaceae (pondweed), Rapateaceae, Restionaceae, Ruppiaceae (ditch grass), Scheuchzeriaceae (scheuchzeria), Smilacaceae (catbrier), Sparganiaceae (bur reed), Stemonaceae (stemona), Strelitziaceae, Taccaceae (tacca), Thurniaceae, Triuridaceae, Typhaceae (cattail), Velloziaceae, Xanthorrhoeaceae, Xyridaceae (yellow-eyed grass), Zannichelliaceae (horned pondweed), Zingiberaceae (ginger), and Zosteraceae (eelgrass).

Where the plant is a gymnosperm, the gymnosperm can be from a family selected from the group consisting of Araucariaceae, Boweniaceae, Cephalotaxaceae, Cupressaceae, Cycadaceae, Ephedraceae, Ginkgoaceae, Gnetaceae, Pinaceae, Podocarpaceae, Taxaceae, Taxodiaceae, Welwitschiaceae, and Zamiaceae.

EXAMPLES

The following non-limiting examples are provided to further illustrate the present invention.

Example 1. Use of a Recombinant *Bacillus cereus* Family Member Displaying a Lipase or an Endogluconase to Stimulate Plant Growth in Soybeans The *Bacillus subtilis* lipase and endoglucanase genes were amplified via polymerase chain reaction (PCR) using the following primers shown below in Table 2:

TABLE 2

| | lipase | endogluconase |
|---|---|---|
| forward | ggatccatggctgaa cacaatcc (SEQ ID NO: 37) | ggatccatgaaacgg tcaatc (SEQ ID NO: 39) |
| reverse | ggatccttaattcgt attctggcc (SEQ ID NO: 38) | ggatccttactaatt tggttctgt (SEQ ID NO: 40) |

To create fusion constructs, genes were fused to the native bclA promoter of *Bacillus thuringiensis* DNA encoding the first 35 amino acids of BclA (amino acids 1-35 of SEQ ID NO:1) using the splicing by overlapping extension (SOE) technique. Correct amplicons were cloned into the *E. coli/Bacillus* shuttle vector pHP13, and correct clones screened by DNA sequencing. Correct clones were electroporated into *Bacillus thuringiensis* (Cry-, plasmid-) and screened for chloramphenicol resistance. Correct transformants were grown in Brain Heart Infusion broth overnight at 30° C., plated onto nutrient agar plates, and incubated at 30° C. for 3 days. Spores expressing the fusion construct (BEMD spores) were collected off of the plates by washing in phosphate buffered saline (PBS) and purified by centrifugation and additional washes in PBS. Non-transformed control *Bacillus thuringiensis* (B.t.) spores were created identically.

Soybeans (strain Jake 011-28-04) were planted 1 inch (2.54 cm) deep in 10 cm deep pots filled with standard loam topsoil. Spores were diluted to a concentration of $1\times10^4$/ml in 50 ml of water and applied to each seed at planting. Plants were grown under ideal light using T5 lamps, 54 watts, and exposed to 11 hours of light a day under controlled temperature conditions between 60-78° F. (15.5-25.5° C.). Plants were watered to saturation every three days over a two week trial. At the end of two weeks, the height of each plant was measured and measurements were normalized to control *Bacillus thuringiensis* spores. Two independent trials were performed.

Results are shown in Table 3, together with the standard error of the mean. In both trials, soybeans grown in the presence of BEMD spores displaying either lipase or endoglucanase grew significantly taller than control B.t. spore treated soybeans (statistical analysis assayed via a t-test).

TABLE 3

| | Treatment | Soybeans Avg. Height, Inches (cm) | Comparison to Control | SEM |
|---|---|---|---|---|
| Trial #1 | Control Bt | 5.525 (14.034) | 100.0% | .521 |
| | Lipase, BEMD | 7.06 (17.93) | 127.8% | .395 |
| | Endocellulase, BEMD | 6.42 (16.31) | 116.2% | .411 |
| Trial #2 | Control Bt | 6.06 (15.39) | 100.0% | .749 |
| | Lipase, BEMD | 7.54 (19.15) | 124.4% | .428 |
| | Endocellulase, BEMD | 6.95 (17.65) | 114.7% | .313 |

Example 2. Use of a Recombinant *Bacillus cereus* Family Member Displaying an Endoglucanase to Stimulate Plant Growth in Corn BEMD spores expressing endoglucanase were created in an identical fashion as described above in Example 1. Field corn was planted 1.5 inches (3.8 cm) deep in 10 cm deep pots filled with standard loam topsoil. Spores, control and BEMD expressing endoglucanase, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 60-78° F. (15.5-25.5° C.). Plants were watered to saturation every three days over the one week trial. At the end of one week, the height of each plant was measured, and measurements were normalized to control *Bacillus thuringiensis* spores.

Results are shown in Table 4, together with the standard error of the mean. Corn grown in the presence of BEMD spores displaying endoglucanase grew significantly taller than both control B.t. spore treated soybeans and water-only control plants (statistical analysis assayed via a t-test).

TABLE 4

| | Height, inches (cm) | Comparison | SEM |
|---|---|---|---|
| $H_2O$ | 6.08 (15.44) | 100% | 0.318 |
| Bt | 7.45 (18.92) | 122.50% | 0.645 |
| BEMD Endo | 8.73 (22.71) | 143.40% | 0.616 |

Example 3. Use of a Recombinant *Bacillus cereus* Family Member Displaying an Endogluconase or a Protease to Stimulate Plant Growth in Wheat BEMD spores expressing endoglucanase were created in an identical fashion as described above in Example 1. BEMD spores expressing *E. coli* protease PtrB were created using similar methods to those described above in Example 1 and the following primers: ggatccatgctaccaaaagcc (forward, SEQ ID NO: 41) and ggatccttagtccgcaggcgtagc (reverse, SEQ ID NO: 42).

Winter hard wheat was planted 1 inch (2.54 cm) deep in 10 cm deep pots filled with standard loam topsoil. Spores, control and BEMD expressing endoglucanase or protease, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 60-78° F. (15.5-25.5° C.). Plants were watered to saturation every three days over the one week trial. At the end of one week, the height of each plant was measured, and measurements were normalized to control water only plants.

Results are shown in Table 5, together with the standard error of the mean. Wheat grown in the presence of BEMD spores displaying endoglucanase or protease grew significantly taller than control B.t. spore treated or water control soybeans (statistical analysis assayed via a t-test).

TABLE 5

| | Height, inches (cm) | Comparison | SEM |
|---|---|---|---|
| $H_2O$ | 7.13 (18.11) | 100% | 0.721 |
| Bt Control | 7.86 (19.96) | 110.33% | 0.752 |
| BEMD Endo | 9.75 (24.76) | 136.80% | 0.21 |
| BEMD Protease | 8.8 (22.35) | 123.40% | 0.354 |

Example 4. Use of Recombinant *Bacillus cereus* Family Members Displaying an Endogluconase to Stimulate Plant Growth in Ryegrass BEMD spores expressing endogluconase were created in an identical fashion as described above in Example 1. Perennial ryegrass was planted 0.25 inches (6.4 mm) deep in 10 cm deep pots filled with standard loam topsoil. Spores, both control and BEMD expressing endogluconase, were diluted to a concentration of $1\times10^4$/ml in 50 ml of water and applied to each plant at planting. A water-only control was also included. Plants were grown under ideal light using T5 lamps, 54 watts, and exposed to 11 hours of light a day under controlled temperature conditions between 60-78° F. (15.5-25.5° C.). Plants were watered to saturation every three days over the two week trial. At the end of two weeks, the height of each plant was measured, and measurements were normalized to control water only plants.

Results are shown in Table 6, together with the standard error of the mean. Ryegrass grown in the presence of BEMD spores displaying endocellulase grew significantly taller than control B.t. spore treated or water control ryegrass (statistical analysis assayed via a t-test).

TABLE 6

| | Height, inches (cm) | Comparison | SEM |
|---|---|---|---|
| $H_2O$ | 4.5 (11.43) | 100.0% | 0.137 |
| Bt Control | 4.84 (12.29) | 107.7% | 0.128 |
| BEMD Endo | 5.03 (12.78) | 111.9% | 0.137 |

Example 5. Use of Recombinant *Bacillus cereus* Family Members Displaying Enzymes Involved in the Synthesis of Plant Hormones to Stimulate Plant Growth The BEMD system can also be used to display enzymes involved in the synthesis of plant hormones. For example, the plant hormone indole-3-acetic acid is a potent growth stimulator in plants. Indole-3-acetic acid is synthesized in vivo from tryptophan by the enzymes tryptophan monoxygenase and indole-3-acetamide hydrolase. Indole-3-acetic acid and other auxin hormones can also be synthesized in vivo from tryptophan and/or indole by the enzymes nitrilase, tryptophan aminotransferase, indole-3-acetaldehyde dehydrogenase, indole-3-pyruvate decarboxylase, amine oxidase, tryptophan decarboxylase, and tryptophan side chain oxidases.

Related plant growth hormones (auxins) include indole-3-pyruvic acid, indole-3-acetaldoxime, indole-3-acetamide, indole-3-acetonitrile, indole-3-ethanol, indole-3-pyruvate, indole-3-butyric acid, phenylacetic acids, 4-chloroindole-3-acetic acid, and indole-3-acetaldoxime. These hormones are synthesized from tryptophan and/or indole in vivo via the enzymes tryptophan monoxygenase, indole-3-acetamide hydrolase, nitrilase, nitrile hydrolase, acetolactate synthetase, alpha acetolactate decarboxylase, tryptophan aminotransferase, indole-3-acetaldehyde dehydrogenase, indole-3-pyruvate decarboxylase, amine oxidase, tryptophan decarboxylase, and tryptophan side chain oxidases.

Growth hormones of the cytokinin family can also be synthesized by enzymes expressed in the BEMD system. Examples of cytokinins include kinetin, zeatin (cis and trans), 6-benzylaminopurine, dihydroxyzeatin, N6-(D2-isopentenyl) adenine, ribosylzeatin, N6-(D2-isopentenyl) adenosine, 2 methylthio-cis-ribosylzeatin, cis ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, and meta-methyltopolin. These plant growth stimulating compounds are synthesized in vivo from mevalonate or adenosine mono/di/triphosphate by enzymes including adenosine phosphate isopentenyltransferases, phosphatases, adenosine kinases, adenine phosphoribosyltransferase, CYP735A, 5' ribonucleotide phosphohydrolase, adenosine nucleosidases, zeatin cis-trans isomerase, zeatin O-glucosyltransferases, β-glucosidases, cis-hydroxylases, CK cis-hydroxylases, CK N-glucosyltransferases, 2,5-ribonucleotide phosphohydrolases, adenosine nucleosidases, purine nucleoside phosphorylases, and zeatin reductases.

Using methods similar to those described above in Example 1, any of these enzymes can be incorporated into the BEMD system for display on BEMD spores by creating a fusion construct comprising the enzyme and a targeting sequence that targets the expressed enzyme to the exosporium when the fusion construct is expressed in a *Bacillus cereus* family member. A recombinant *Bacillus cereus* family member expressing such a construct can then be added to the soil or other plant growth medium or applied directly to plant foliage using methods similar to those described above in Example 1 for stimulation of plant growth.

The plant growth medium can be supplemented with precursors or substrates for the enzymes. For example, the plant growth medium can be supplemented with tryptophan, adenosine monophosphates, adenosine diphosphates, adenosine triphosphates, or indole. Suitable concentrations of these substrates are between 100 nM and 100 μM.

Example 6. Use of Recombinant *Bacillus cereus* Family Members Displaying Proteases or Peptidases that Cleave Proteins or Peptides into Bioactive Peptides for Stimulation of Plant Growth Proteases and peptidases can be expressed in the BEMD system that can enzymatically cleave available proteins in the plant growth media to bioactive peptides that can act on the plant directly or indirectly. Examples include the enzymatic cleavage of soybean meal, yeast extract, or other protein rich meals added to the plant growth medium into active peptides that can directly stimulate plant growth. Bioactive peptides generated by enzymatic cleavage of protein meals include RHPP and RKN 16D10, potent stimulators of plant root development.

Using methods similar to those described above in Example 1, any of these proteases and peptidases can be incorporated into the BEMD system for display on BEMD spores by creating a fusion construct comprising the protease or peptidase and a targeting sequence that targets the expressed enzyme to the exosporium when the fusion construct is expressed in a *Bacillus cereus* family member. A recombinant *Bacillus cereus* family member expressing such a construct can then be added to soil or other plant growth medium supplemented with soybean meal, yeast extract, or another-protein-rich meal for stimulation of plant growth. The soybean meal, yeast extract, or other protein-rich meal is suitably added to the plant growth medium in the form of a liquid composition comprising about 10 μg/L to about 100 mg/L of the protein meal, yeast extract, or other protein-rich meal.

Example 7. Use of Recombinant *Bacillus cereus* Family Members Displaying Proteins or Peptides Involved in the Stimulation of Plant Growth The BEMD system can also be used to display proteins or peptides that are directly involved in the promotion of plant growth. For example, plant peptide hormones or non-hormone peptides that stimulate plant growth can be expressed in the BEMD system. For example, non-hormone peptides that directly bind to and active plant receptors can be expressed in the BEMD system to directly act on receptors in the plant and roots of target plants. Such peptide hormones and bioactive peptides include phytosulfokine, calcalva 3 (CLV3), systemin, RKN 16D10, Hg-Syv46, eNOD40, Zm1GF, SCR/SP11 family proteins and peptides, RHPP, and KTI (kunitz trypsin inhibitor). These peptides and related peptides can be expressed in the BEMD system and delivered to plant growth medium or directly applied to foliage to stimulate plant growth.

Using methods similar to those described above in Example 1, any of these proteins or peptides can be incorporated into the BEMD system for display on BEMD spores by creating a fusion construct comprising the enzyme and a targeting sequence that targets the expressed enzyme to the exosporium when the fusion construct is expressed in a *Bacillus cereus* family member. A recombinant *Bacillus cereus* family member expressing such a construct can then be added to the soil or other plant growth medium or applied directly to plant foliage using methods similar to those described above in Example 1 for stimulation of plant growth.

Example 8. Use of Recombinant *Bacillus cereus* Family Members Displaying Enzymes that Degrade or Modify a Bacterial, Fungal, or Plant Nutrient Source to Stimulate Plant Growth The BEMD system can also be used display enzymes that degrade or modify beneficially a bacterial, fungal, or plant nutrient source present in soil or another plant growth medium. Such enzymes degrade products present in the soil or other plant growth medium into forms that can easily be taken up by plants and/or the beneficial bacteria and/or fungi of the rhizosphere. Such enzymes include, for example, glucoside hydrolases to degrade complex carbohydrates, cellulases to degrade cellulose; lipases to degrade lipids, including oil, fats, and waxes; lignin oxidases to degrade down lignin and humic acids; and proteases to degrade polypeptides. The resultant products, including simple sugars, amino acids, fatty acids, and other nutrients will be readily available for direct uptake by plants and/or for stimulating beneficial bacteria and/or fungi to grow and thrive in the rhizospheres of the plants.

In addition, enzymes and other biological molecules can be utilized to release or sequester phosphate, nitrogen, and other key elemental nutrients for plant uptake from their various organic and inorganic forms in soil. For example, phosphatases can be used to degrade phosphates in the environment into usable inorganic phosphates for plant use. The phosphates can be naturally occurring phosphates present in a plant growth medium. Alternatively, the plant growth medium can be supplemented with phosphates such as trimetaphosphate, a common agricultural amendment. Examples of useful phosphatases include phosphoric monoester hydrolases, phosphomonoesterases, phosphoric diester hydrolases, phosphodiesterases, triphosphoric monoester hydrolases, phosphoryl anhydride hydrolases, pyrophosphatases, phytase, trimetaphosphatases, and triphosphatases. For example, the enzymes trimetaphosphatase, triphosphatase, and pyrophosphatase sequentially break down trimetaphosphate into usable inorganic phosphate.

The nitrogenase family of enzymes convert atmospheric nitrogen ($N_2$) into ammonia, thereby converting nitrogen that would otherwise be unaccessible to plants into a usable form. Suitable enzymes belong to the Nif family of nitrogenases.

Chemical energy can also be directly added into the plant growth medium as adenosine-3-triphosphate, ferrodoxin, or additional enzymes that create such energy into the BEMD system. These are cofactors for the nitrogenases and are limited in soil. Thus, such cofactors can be added to soil to enhance the reactions described above.

Using methods similar to those described above in Example 1, any of these enzymes can be incorporated into the BEMD system for display on BEMD spores by creating a fusion construct comprising the enzyme and a targeting sequence for targeting the fusion construct to the exosporium of a *Bacillus cereus* family member. The fusion construct can then be expressed in a *Bacillus cereus* family member, and this recombinant *Bacillus cereus* family member can be added to soil or another plant growth medium using methods similar to those described above in Example 1 for stimulation of plant growth.

Example 9. Use of Recombinant *Bacillus cereus* Family Members Displaying Enzymes Involved in the Synthesis of 2,3-Butanediol for Stimulation of Plant Growth The BEMD system can also be used display enzymes involved in the synthesis of the plant growth promoting compound 2,3-butanediol. In vivo, 2,3-butanediol is synthesized by beneficial bacteria and fungi in the rhizosphere from acetoin, diacetyl, acetolactate, or pyruvate by the enzymes acetolactate synthetase, α-acetolactate decarboxylase, pyruvate decarboxylase, diacetyl reductase, butanediol dehydrogenases, and acetoin reductase.

Any of these enzymes can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for stimulation of plant growth.

To increase the effect of the enzymes displayed on BEMD, the soil can be supplemented with substrates for the enzymes. For example, the soil can be supplemented with acetoin, which is a substrate for acetoin reductase; pyruvate, which is a substrate for pyruvate decarboxylase; diacetyl, which is a substrate for diacetyl reductase; and/or acetolactate, which is a substrate for acetolactate decarboxylase.

Example 10. Use of Recombinant *Bacillus cereus* Family Members Displaying Proteases for Protecting Plants from Pathogens The BEMD system can also be used display proteases that protect plants from one or more pathogens. For example, certain bacterial pathogens can communicate between individual members via secretion of bacterial lactone homoserines or related signaling molecules. Thus, proteases specific for bacterial lactone homoserine signaling molecules can protect plants from such bacterial pathogens by disrupting communication between bacteria, a step essential for the bacteria to secrete toxins and upregulate virulence factors. Suitable proteases specific for bacterial lactone homoserine signaling molecules include endopeptidases and exopeptidases.

Proteases specific for bacterial lactone homoserine signaling molecules can be incorporated into the BEMD system using methods similar to those described above in Example 1. A fusion construct can be prepared that comprises the protease and a targeting sequence that targets the protease to the exosporium when the fusion construct is expressed in a *Bacillus cereus* family member. The fusion construct is then expressed in a *Bacillus cereus* family member, and the *Bacillus cereus* family member is added to soil or another plant growth medium. The protease can then degrade the bacterial lactone homoserine signaling molecules, blocking a key step in the virulence of these organisms and thereby helping to protect the plant from these pathogens.

Example 11. Use of Recombinant *Bacillus cereus* Family Members Displaying Antimicrobial Proteins and Peptides for Protecting Plants from Pathogens The BEMD system can also be used display enzymes that exhibit antibacterial and/or antifungal activities that can help protect plants from one or more pathogens. For example, antibacterial proteins such as bacteriocins, lysozymes, siderophores, avidins, streptavidins, conalbumin, albumin, and lactoferrin can all be expressed in the BEMD system to exert their effect on bacterial and fungal pathogens of plants. Bacteriocins, albumin, conalbumin, lysozymes, and lactoferrin exert direct antimicrobial action on their targets, whereas siderophores, avidins, streptavidins bind essential nutrients that pathogens require for virulence. For example, the peptide lactoferrin, when expressed on the surface of the BEMD system would lyse bacteria cells that are susceptible to the lactoferrin peptides in the plant growth medium. These proteins and peptides have specific action on select microbes, and can selectively target a group of pathogens without obstructing all microbes in the plant growth medium.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from one or more pathogens.

Example 12. Use of Recombinant *Bacillus cereus* Family Members Displaying Enzymes for Protecting Plants from Pathogens The BEMD system can also be used display enzymes that protect plants from one or more pathogens. For example, yeast and mold cell walls are degraded by enzymes such as β-1,3-glucanases, β-1,4-glucanases, β-1,6-glucanases, chitosinases, chitinases, chitosinase-like proteins, and lyticases. Bacteria cell walls are degraded by enzymes selected from proteinases, proteases, mutanolysin, stapholysin, and lysozymes. Each of these cell wall degrading enzymes can be expressed on the BEMD system and added to plant growth medium for selective inhibition of pathogenic microbes in the rhizosphere.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from pathogens.

Example 13. Use of Recombinant *Bacillus cereus* Family Members Displaying Plant Immune System Stimulatory Peptides or Proteins for Protecting Plants from Pathogens The BEMD system can also be used display plant immune system enhancer peptides and proteins. These proteins can be expressed on the outside of the BEMD spore and delivered into the plant growth medium to stimulate the plant immune system to allow the plant to protect itself from plant pathogens. Example proteins and peptides include harpin, α-elastins, β-elastins, cryptogein, and flagellin proteins and peptides. Exposure of plants to these proteins and peptides will stimulate resistance to many plant pathogens in plants.

Any of these proteins or peptides can be incorporated into the BEMD system for display on BEMD spores using methods similar to those described above in Example 1. A fusion construct can be prepared that comprises the enzyme and a targeting sequence that targets the enzyme to the exosporium when the fusion construct is expressed in a *Bacillus cereus* family member. The fusion construct is then expressed in a *Bacillus cereus* family member, and the *Bacillus cereus* family member is added to soil or another plant growth medium for protection of plants from pathogens.

Example 14. Use of Recombinant *Bacillus cereus* Family Members Displaying a Root Binding Protein or Peptide to Immobilize the Recombinant *Bacillus cereus* Family Member on a Root System of a Plant Root binding proteins and peptides can also be incorporated into the BEMD system to allow the BEMD spores to be immobilized on a root system of a plant. Display of such root binding ligands on the BEMD spores allows for targeting of the spores to the root system of a plant or to substructures of the root system to maintain the BEMD spores at an optimal location for other displayed biological molecules and enzymes to be effective.

For example, rhicadhesin is a root binding ligand that binds to root hairs. Thus, display of rhicadhesin on the BEMD spores thus targets the spores to root hairs. Additional proteins that could be utilized for selective binding to plants include adhesins, falgellin, omptins, lectins, pili proteins, curlus proteins, intimins, invasins, agglutinin, and afimbrial proteins.

Such root binding proteins and peptides can be incorporated into the BEMD system using methods similar to those described above in Example 1. A fusion construct can be prepared that comprises the root binding protein or peptide and a targeting sequence that targets the protein or peptide to the exosporium when the construct is expressed in a *Bacillus cereus* family member. The fusion construct containing the root binding ligand is then expressed in a *Bacillus cereus* family member. Such fusion constructs can be coexpressed with one or more additional fusion constructs comprising any of the beneficial enzymes discussed herein (e.g., an enzyme involved in the synthesis of a plant hormone, an enzyme that degrades a nutrient source, or a proteases that protects a plant from a pathogen). The recombinant *Bacillus cereus* family member is added to soil or another plant growth medium. The root binding ligand targets the *Bacillus cereus* family member to the root system of the plant and immobilizes it there, thus allowing the coexpressed fusion construct to exert its effects in close proximity to the root system.

In view of the above, it will be seen that the several objects of the invention are achieved and other advantageous results attained.

As various changes could be made in the above fusion proteins, *Bacillus cereus* family members, formulations, and methods without departing from the scope of the invention, it is intended that all matter contained in the above description and shown in the accompanying drawing shall be interpreted as illustrative and not in a limiting sense.

What is claimed is:

1. A plant seed coated with a recombinant *Bacillus cereus* family member, wherein the recombinant *Bacillus cereus* family member expresses a fusion protein and the fusion protein comprises at least one plant growth stimulating protein or peptide and a targeting sequence or exosporium protein that targets the fusion protein to the exosporium of the recombinant *Bacillus cereus* family member, wherein plants grown from the coated plant seeds exhibit increased growth as compared to plants grown from plant seeds to which the recombinant *Bacillus cereus* family member has not been applied, under the same conditions.

2. A plant seed of claim 1, wherein the plant seed is coated with a seed coating formulation comprising the recombinant *Bacillus cereus* family member and an agriculturally acceptable carrier.

3. A plant seed of claim 1, wherein the fusion protein comprises a targeting sequence comprising an amino acid sequence having at least about 43% identity with amino acids 20-35 of SEQ ID NO: 1, wherein the identity with amino acids 25-35 is at least about 54%.

4. A plant seed of claim 1, wherein the targeting sequence comprises an amino acid sequence having at least about 50% identity with amino acids 20-35 of SEQ ID NO: 1, wherein the identity with amino acids 25-35 is at least about 63%.

5. A plant seed of claim 1, wherein the targeting sequence comprises an amino sequence having at least about 62% identity with amino acids 20-35 of SEQ ID NO: 1, wherein the identity with amino acids 25-35 is at least about 72%.

6. A plant seed of claim 1, wherein the targeting sequence comprises an amino acid sequence having at least about 81% identity with amino acids 20-35 of SEQ ID NO: 1, wherein the identity with amino acids 25-35 is at least about 90%.

7. A plant seed of claim 1, wherein the targeting sequence consists of:

(a) a 16 amino acid sequence having at least about 43% identity with amino acids 20-35 of SEQ ID NO: 1, wherein the identity with amino acids 25-35 is at least about 54%;

(b) amino acids 1-35 of SEQ ID NO: 1;
(c) amino acids 20-35 of SEQ ID NO: 1; or
(d) SEQ ID NO: 1.

8. A plant seed of claim 1, wherein the fusion protein comprises:
(a) a targeting sequence comprising amino acids 1-35 of SEQ ID NO: 1;
(b) a targeting sequence comprising amino acids 20-35 of SEQ ID NO: 1;
(c) a targeting sequence comprising SEQ ID NO: 1;
(d) an exosporium protein comprising SEQ ID NO: 2;
(e) a targeting sequence comprising amino acids 1-27 of SEQ ID NO: 3;
(f) a targeting sequence comprising amino acids 12-27 of SEQ ID NO: 3;
(g) a targeting sequence comprising SEQ ID NO: 3;
(h) an exosporium protein comprising SEQ ID NO: 4;
(i) a targeting sequence comprising amino acids 1-38 of SEQ ID NO: 5;
(j) a targeting sequence comprising amino acids 23-38 of SEQ ID NO: 5;
(k) a targeting sequence comprising SEQ ID NO: 5;
(l) an exosporium protein comprising SEQ ID NO: 6;
(m) a targeting sequence comprising amino acids 1-28 of SEQ ID NO: 7;
(n) a targeting sequence comprising amino acids 13-28 of SEQ ID NO: 7;
(o) a targeting sequence comprising SEQ ID NO: 7;
(p) an exosporium protein comprising SEQ ID NO: 8;
(q) a targeting sequence comprising amino acids 1-24 of SEQ ID NO: 9;
(r) a targeting sequence comprising amino acids 9-24 of SEQ ID NO: 9;
(s) a targeting sequence comprising SEQ ID NO: 9;
(t) an exosporium protein comprising SEQ ID NO: 10;
(u) a targeting sequence comprising amino acids 1-33 of SEQ ID NO: 11;
(v) a targeting sequence comprising amino acids 18-33 of SEQ ID NO: 11;
(w) a targeting sequence comprising SEQ ID NO: 11;
(x) an exosporium protein comprising SEQ ID NO: 12;
(y) a targeting sequence comprising amino acids 1-33 of SEQ ID NO: 13;
(z) a targeting sequence comprising amino acids 18-33 of SEQ ID NO: 13;
(aa) a targeting sequence comprising amino SEQ ID NO: 13;
(ab) an exosporium protein comprising SEQ ID NO: 14;
(ac) a targeting sequence comprising amino acids 1-43 of SEQ ID NO: 15;
(ad) a targeting sequence comprising amino acids 28-43 of SEQ ID NO: 15;
(ae) a targeting sequence comprising amino SEQ ID NO: 15;
(af) an exosporium protein comprising SEQ ID NO: 16;
(ag) a targeting sequence comprising amino acids 1-27 of SEQ ID NO: 17;
(ah) a targeting sequence comprising amino acids 12-27 of SEQ ID NO: 17;
(ai) a targeting sequence comprising amino SEQ ID NO: 17;
(aj) an exosporium protein comprising SEQ ID NO: 18;
(ak) a targeting sequence comprising amino acids 1-33 of SEQ ID NO: 19;
(al) a targeting sequence comprising amino acids 18-33 of SEQ ID NO: 19;
(am) a targeting sequence comprising amino SEQ ID NO: 19;
(an) an exosporium protein comprising SEQ ID NO: 20;
(ao) a targeting sequence comprising amino acids 1-33 of SEQ ID NO: 21;
(ap) a targeting sequence comprising amino acids 18-33 of SEQ ID NO: 21;
(aq) a targeting sequence comprising amino SEQ ID NO: 21;
(ar) an exosporium protein comprising SEQ ID NO: 22;
(as) a targeting sequence comprising amino acids 1-24 of SEQ ID NO: 23;
(at) a targeting sequence comprising amino acids 9-24 of SEQ ID NO: 23;
(au) a targeting sequence comprising amino SEQ ID NO: 23;
(av) an exosporium protein comprising SEQ ID NO: 24;
(aw) a targeting sequence comprising amino acids 1-24 of SEQ ID NO: 25;
(ax) a targeting sequence comprising amino acids 9-24 of SEQ ID NO: 25;
(ay) a targeting sequence comprising amino SEQ ID NO: 25;
(az) an exosporium protein comprising SEQ ID NO: 26;
(ba) a targeting sequence comprising amino acids 1-30 of SEQ ID NO: 27;
(bb) a targeting sequence comprising amino acids 15-30 of SEQ ID NO: 27;
(bc) a targeting sequence comprising amino SEQ ID NO: 27;
(bd) an exosporium protein comprising SEQ ID NO: 28;
(be) a targeting sequence comprising amino acids 1-33 of SEQ ID NO: 29;
(bf) a targeting sequence comprising amino acids 18-33 of SEQ ID NO: 29;
(bg) a targeting sequence comprising amino SEQ ID NO: 29;
(bh) an exosporium protein comprising SEQ ID NO: 30;
(bi) a targeting sequence comprising amino acids 1-24 of SEQ ID NO: 31;
(bj) a targeting sequence comprising amino acids 9-24 of SEQ ID NO: 31;
(bk) a targeting sequence comprising amino SEQ ID NO: 31;
(bl) an exosporium protein comprising SEQ ID NO: 32;
(bm) a targeting sequence comprising amino acids 1-15 of SEQ ID NO: 33;
(bn) a targeting sequence comprising amino SEQ ID NO: 33;
(bo) an exosporium protein comprising SEQ ID NO: 34;
(bp) a targeting sequence comprising amino acids 1-16 of SEQ ID NO: 35;
(bq) a targeting sequence comprising amino SEQ ID NO: 35; or
(br) an exosporium protein comprising SEQ ID NO: 36.

9. A plant seed of claim 1, wherein the targeting sequence comprises the amino acid sequence GXT at its carboxy terminus, wherein X is any amino acid.

10. A plant seed of claim 1, wherein the plant growth stimulating protein or peptide comprises an enzyme.

11. A plant seed of claim 10, wherein the enzyme comprises an enzyme that degrades or modifies a bacterial, fungal, or plant nutrient source.

12. A plant seed of claim 10, wherein the enzyme comprises a cellulase, a lipase, a lignin oxidase, a protease, a glycoside hydrolase, a phosphatase, a nitrogenase, or a nuclease.

13. A plant seed of claim 12, wherein the cellulase comprises an endocellulase, an exocellulase, or a β-glucosidase.

14. A plant seed of claim 13, wherein the endocellulase comprises a *Bacillus subtilis* endoglucanase, a *Bacillus thuringiensis* endoglucanase, a *Bacillus cereus* endoglucanase, or a *Bacillus clausii* endoglucanase.

15. A plant seed of claim 12, wherein the lipase comprises a *Bacillus subtilis* lipase, a *Bacillus thuringiensis* lipase, a *Bacillus cereus* lipase, or a *Bacillus clausii* lipase.

16. A plant seed of claim 12, wherein the lignin oxidase comprises a lignin peroxidase, a laccase, a glyoxal oxidase, a ligninase, or a manganese peroxidase.

17. A plant seed of claim 12, wherein the protease comprises a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

18. A plant seed of claim 12, wherein the phosphatase comprises a phosphoric monoester hydrolase, a phosphomonoesterase, a phosphoric diester hydrolase, a phosphodiesterase, a triphosphoric monoester hydrolase, a phosphoryl anhydride hydrolase, a pyrophosphatase, a phytase, a trimetaphosphatase, or a triphosphatase.

19. A plant seed of claim 12, wherein the nitrogenase comprises a Nif family nitrogenase.

20. A plant seed of claim 1, wherein the plant growth stimulating protein or peptide comprises a peptide hormone.

21. A plant seed of claim 20, wherein the peptide hormone comprises a phytosulfokine, clavata 3 (CLV3), systemin, ZmlGF, or a SCR/SP11.

22. A plant seed of claim 1, wherein the plant growth stimulating protein or peptide comprises a non-hormone peptide.

23. A plant seed of claim 22, wherein the non-hormone peptide comprises a RKN 16D10, Hg-Syv46, an eNOD40 peptide, RHPP, or kunitz trypsin inhibitor.

24. A plant seed of claim 1, wherein the plant growth stimulating protein or peptide comprises an enzyme involved in the production of a plant growth stimulating compound.

25. A plant seed of claim 24, wherein the plant growth stimulating compound comprises 2,3-butanediol or a plant growth hormone.

26. A plant seed of claim 25, wherein the plant growth hormone comprises a cytokinin or an auxin.

27. A plant seed of claim 24, wherein the enzyme involved in the production of a plant growth stimulating compound comprises an acetoin reductase, an indole-3-acetamide hydrolase, a tryptophan monoxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin O-glucosyltransferase, a β-glucosidase, a cishydroxylase, a CK cis-hydroxylase, a CK N-glucosyltransferase, a 2,5-ribonucleotide phosphohydrolase, an adenosine nucleosidase, a purine nucleoside phosphorylase, or a zeatin reductase.

28. A plant seed of claim 27, wherein the enzyme comprises a protease or peptidase that cleaves proteins or peptides to create a bioactive peptide, the protease or peptidase comprising subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

29. A plant seed of claim 1, wherein the plant growth stimulating protein or peptide comprises at least one protein or peptide that protects a plant from a pathogen.

30. A plant seed of claim 29, wherein the protein or peptide that protects a plant from a pathogen comprises a plant immune system enhancer protein or peptide.

31. A plant seed of claim 30, wherein the plant immune system enhancer protein or peptide comprises a harpin, an α-elastin, a β-elastin, a cryptogein, a flagellin protein, or a flagellin peptide.

32. A plant seed of claim 29, wherein the protein or peptide that protects a plant from a pathogen has antibacterial activity, antifungal activity, or both antibacterial and antifungal activity.

33. A plant seed of claim 29, wherein the protein or peptide that protects a plant from a pathogen comprises a bacteriocin, a lysozyme, a siderophore, an avidin, a streptavidin, a conalbumin, an albumin, or a lactoferrin.

34. A plant seed of claim 29, wherein the protein that protects a plant from a pathogen comprises an enzyme.

35. A plant seed of claim 34, wherein the enzyme comprises a protease or a lactonase.

36. A plant seed of claim 35, wherein the protease or lactonase is specific for a bacterial lactone homoserine signaling molecule.

37. A plant seed of claim 36, wherein the bacterial lactone homoserine signaling molecule comprises a bacterial lactone homoserine signaling molecule and the lactonase comprises 1,4-lactonase, 2-pyrone-4,6-dicarboxylate lactonase, 3-oxoadipate enol-lactonase, actinomycin lactonase, deoxylimonate A-ring-lactonase, gluconolactonase L-rhamnono-1,4-lactonase, limonin-D-ring-lactonase, steroid-lactonase, triacetate-lactonase, or xylono-1,4-lactonase.

38. A plant seed of claim 34, wherein the enzyme is specific for a cellular component of a bacterium or fungus, the enzyme comprising a β-1,3-glucanase, a β-1,4-glucanase, a β-1,6-glucanase, a chitosinase, a chitinase, a chitosinase-like enzyme, a lyticase, a peptidase, a proteinase, a protease, a mutanolysin, a stapholysin, or a lysozyme.

39. A plant seed of claim 29, wherein the protein or peptide that protects a plant from a pathogen protects the plant from a bacterial or fungal pathogen, the bacterial pathogen comprising:

an α-class Proteobacterium, a β-class Proteobacterium, a γ-class Proteobacterium, or a combination thereof; or

*Agrobacterium tumefaciens, Pantoea stewartii, Erwinia carotovora, Ralstonia solanacearum, Pseudomonas syringae, Pseudomonas aeruginosa, Xanthomonas campestris*, or a combination thereof.

40. A plant seed of claim 1, wherein the plant growth stimulating protein or peptide comprises at least one root binding protein or peptide.

41. A plant seed of claim 40, wherein the root binding protein or peptide comprises an adhesin, a rhicadhesin, a flagellin, an omptin, a lectin, a pilus protein, a curlus protein, an intimin, an invasin, an agglutinin, or an afimbrial protein.

42. A plant seed of claim 1, wherein the recombinant *Bacillus cereus* family member comprises *Bacillus anthra-*

*cis, Bacillus cereus, Bacillus thuringiensis, Bacillus mycoides, Bacillus pseudomycoides, Bacillus weihenstephensis*, or a combination thereof.

43. A plant seed of claim 1, wherein the plant growth stimulating protein or peptide is physically attached to the exosporium of the recombinant *Bacillus cereus* family member.

44. A plant seed of claim 1, wherein the recombinant *Bacillus cereus* family member is inactivated.

45. A plant seed of claim 1, wherein the plant growth stimulating protein or peptide comprises a cellulase and the targeting sequence comprises amino acids 20-35 of SEQ ID NO: 1.

46. A plant seed of claim 45, wherein the cellulase comprises an endoglucanase.

47. A plant seed of claim 1, wherein the plant growth stimulating protein or peptide comprises a lipase and the targeting sequence comprises amino acids 20-35 of SEQ ID NO: 1.

48. A plant seed of claim 1, wherein the plant growth stimulating protein or peptide comprises a flagellin peptide and the targeting sequence comprises amino acids 20-35 of SEQ ID NO: 1.

49. A plant seed of claim 1, wherein the plant growth stimulating protein or peptide comprises a lactonase and the targeting sequence comprises amino acids 20-35 of SEQ ID NO: 1.

* * * * *

```
                         SEQUENCE LISTING

<160> NUMBER OF SEQ ID NOS: 42

<210> SEQ ID NO 1
<211> LENGTH: 41
<212> TYPE: PRT
<213> ORGANISM: Bacillus anthracis

<400> SEQUENCE: 1

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40


<210> SEQ ID NO 2
<211> LENGTH: 332
<212> TYPE: PRT
<213> ORGANISM: Bacillus anthracis

<400> SEQUENCE: 2

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly Pro Thr Gly Pro Phe Thr Thr
        35                  40                  45

Gly Pro Thr Gly Pro Thr Gly Pro Thr Gly Pro Thr Gly Pro Thr Gly
    50                  55                  60
```

```
Pro Thr Gly Pro Thr Gly Pro Thr Gly Asp Thr Gly Thr Thr Gly Pro
65                  70                  75                  80

Thr Gly Pro Thr Gly Pro Thr Gly Pro Thr Gly Pro Thr Gly Pro Thr
                85                  90                  95

Gly Pro Thr Gly Pro Thr Gly Pro Thr Gly Phe Thr Pro Thr Gly Pro
            100                 105                 110

Thr Gly Pro Thr Gly Pro Thr Gly Asp Thr Gly Thr Thr Gly Pro Thr
        115                 120                 125

Gly Pro Thr Gly Pro Thr Gly Pro Thr Gly Pro Thr Gly Asp Thr Gly
    130                 135                 140

Thr Thr Gly Pro Thr Gly Pro Thr Gly Pro Thr Gly Pro Thr Gly Pro
145                 150                 155                 160

Thr Gly Pro Thr Gly Pro Thr Phe Thr Gly Pro Thr Gly Pro Thr Gly
                165                 170                 175

Pro Thr Gly Ala Thr Gly Leu Thr Gly Pro Thr Gly Pro Thr Gly Pro
            180                 185                 190

Ser Gly Leu Gly Leu Pro Ala Gly Leu Tyr Ala Phe Asn Ser Gly Gly
        195                 200                 205

Ile Ser Leu Asp Leu Gly Ile Asn Asp Pro Val Pro Phe Asn Thr Val
    210                 215                 220

Gly Ser Gln Phe Phe Thr Gly Thr Ala Ile Ser Gln Leu Asp Ala Asp
225                 230                 235                 240

Thr Phe Val Ile Ser Glu Thr Gly Phe Tyr Lys Ile Thr Val Ile Ala
                245                 250                 255

Asn Thr Ala Thr Ala Ser Val Leu Gly Gly Leu Thr Ile Gln Val Asn
            260                 265                 270

Gly Val Pro Val Pro Gly Thr Gly Ser Ser Leu Ile Ser Leu Gly Ala
        275                 280                 285

Pro Phe Thr Ile Val Ile Gln Ala Ile Thr Gln Ile Thr Thr Thr Pro
    290                 295                 300

Ser Leu Val Glu Val Ile Val Thr Gly Leu Gly Leu Ser Leu Ala Leu
305                 310                 315                 320

Gly Thr Ser Ala Ser Ile Ile Ile Glu Lys Val Ala
                325                 330


<210> SEQ ID NO 3
<211> LENGTH: 33
<212> TYPE: PRT
<213> ORGANISM: Bacillus anthracis

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly


<210> SEQ ID NO 4
<211> LENGTH: 209
<212> TYPE: PRT
<213> ORGANISM: Bacillus anthracis

<400> SEQUENCE: 4

Met Ser Glu Lys Tyr Ile Ile Leu His Gly Thr Ala Leu Glu Pro Asn
1               5                   10                  15
```

```
Leu Ile Gly Pro Thr Leu Pro Pro Ile Pro Pro Phe Thr Phe Pro Asn
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Leu Gly Ile Leu Pro Val Phe
65                  70                  75                  80

Gly Thr Ile Thr Thr Asp Val Gly Ile Gly Phe Ser Val Ile Val Asn
                85                  90                  95

Thr Asn Ile Asn Phe Thr Leu Pro Gly Pro Val Ser Gly Thr Thr Leu
            100                 105                 110

Asn Pro Val Asp Asn Ser Ile Ile Ile Asn Thr Thr Gly Val Tyr Ser
        115                 120                 125

Val Ser Phe Ser Ile Val Phe Val Ile Gln Ala Ile Ser Ser Ser Ile
    130                 135                 140

Leu Asn Leu Thr Ile Asn Asp Ser Ile Gln Phe Ala Ile Glu Ser Arg
145                 150                 155                 160

Ile Gly Gly Gly Pro Gly Val Arg Ala Thr Ser Ala Arg Thr Asp Leu
                165                 170                 175

Leu Ser Leu Asn Gln Gly Asp Val Leu Arg Val Arg Ile Arg Glu Ala
            180                 185                 190

Thr Gly Asp Ile Ile Tyr Ser Asn Ala Ser Leu Val Val Ser Lys Val
        195                 200                 205

Asp


<210> SEQ ID NO 5
<211> LENGTH: 44
<212> TYPE: PRT
<213> ORGANISM: Bacillus anthracis

<400> SEQUENCE: 5

Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
        35                  40


<210> SEQ ID NO 6
<211> LENGTH: 647
<212> TYPE: PRT
<213> ORGANISM: Bacillus anthracis

<400> SEQUENCE: 6

Val Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr Gly Ser Thr Gly
        35                  40                  45

Ala Thr Gly Asn Thr Gly Pro Thr Gly Glu Thr Gly Ala Thr Gly Ser
    50                  55                  60

Ala Gly Ile Thr Gly Ser Thr Gly Pro Thr Gly Asn Thr Gly Gly Thr
65                  70                  75                  80

Gly Ser Thr Gly Pro Thr Gly Asn Thr Gly Ala Thr Gly Ser Thr Gly
```

-continued

```
                85                  90                  95

Val Thr Gly Ser Thr Gly Val Thr Gly Ser Thr Gly Val Thr Gly Ser
            100                 105                 110

Thr Gly Val Thr Gly Ser Thr Gly Pro Thr Gly Glu Thr Gly Gly Thr
        115                 120                 125

Gly Ser Thr Gly Val Thr Gly Ser Thr Gly Ala Thr Gly Ser Thr Gly
    130                 135                 140

Val Thr Gly Asn Thr Gly Pro Thr Gly Ser Thr Gly Ala Thr Gly Asn
145                 150                 155                 160

Thr Gly Ser Ile Gly Glu Thr Gly Gly Thr Gly Ser Met Gly Pro Thr
                165                 170                 175

Gly Glu Thr Gly Val Thr Gly Ser Thr Gly Gly Thr Gly Ser Thr Gly
            180                 185                 190

Val Thr Gly Asn Thr Gly Pro Thr Gly Ser Thr Gly Val Thr Gly Ser
        195                 200                 205

Thr Gly Val Thr Gly Ser Thr Gly Pro Thr Gly Ser Thr Gly Val Thr
    210                 215                 220

Gly Ser Thr Gly Pro Thr Gly Ser Thr Gly Val Thr Gly Ser Thr Gly
225                 230                 235                 240

Val Thr Gly Asn Met Gly Pro Thr Gly Ser Thr Gly Val Thr Gly Asn
                245                 250                 255

Thr Gly Ser Thr Gly Thr Thr Gly Ala Thr Gly Glu Thr Gly Pro Met
            260                 265                 270

Gly Ser Thr Gly Ala Thr Gly Thr Thr Gly Pro Thr Gly Glu Thr Gly
        275                 280                 285

Glu Thr Gly Glu Thr Gly Gly Thr Gly Ser Thr Gly Pro Thr Gly Asn
    290                 295                 300

Thr Gly Ala Thr Gly Ser Thr Gly Val Thr Gly Ser Thr Gly Val Thr
305                 310                 315                 320

Gly Ser Thr Gly Val Thr Gly Glu Thr Gly Pro Thr Gly Ser Thr Gly
                325                 330                 335

Ala Thr Gly Asn Thr Gly Pro Thr Gly Glu Thr Gly Gly Thr Gly Ser
            340                 345                 350

Thr Gly Ala Thr Gly Ser Thr Gly Val Thr Gly Asn Thr Gly Pro Thr
        355                 360                 365

Gly Ser Thr Gly Val Thr Gly Asn Thr Gly Ala Thr Gly Glu Thr Gly
    370                 375                 380

Pro Thr Gly Asn Thr Gly Ala Thr Gly Asn Thr Gly Pro Thr Gly Glu
385                 390                 395                 400

Thr Gly Val Thr Gly Ser Thr Gly Pro Thr Gly Glu Thr Gly Val Thr
                405                 410                 415

Gly Ser Thr Gly Pro Thr Gly Asn Thr Gly Ala Thr Gly Glu Thr Gly
            420                 425                 430

Ala Thr Gly Ser Thr Gly Val Thr Gly Asn Thr Gly Ser Thr Gly Glu
        435                 440                 445

Thr Gly Pro Thr Gly Ser Thr Gly Pro Thr Gly Ser Thr Gly Ala Thr
    450                 455                 460

Gly Val Thr Gly Asn Thr Gly Pro Thr Gly Ser Thr Gly Ala Thr Gly
465                 470                 475                 480

Ala Thr Gly Ser Thr Gly Pro Thr Gly Ser Thr Gly Thr Thr Gly Asn
                485                 490                 495

Thr Gly Val Thr Gly Asp Thr Gly Pro Thr Gly Ala Thr Gly Val Ser
            500                 505                 510
```

```
Thr Thr Ala Thr Tyr Ala Phe Ala Asn Asn Thr Ser Gly Ser Val Ile
        515                 520                 525

Ser Val Leu Leu Gly Gly Thr Asn Ile Pro Leu Pro Asn Asn Gln Asn
    530                 535                 540

Ile Gly Pro Gly Ile Thr Val Ser Gly Gly Asn Thr Val Phe Thr Val
545                 550                 555                 560

Ala Asn Ala Gly Asn Tyr Tyr Ile Ala Tyr Thr Ile Asn Leu Thr Ala
                565                 570                 575

Gly Leu Leu Val Ser Ser Arg Ile Thr Val Asn Gly Ser Pro Leu Ala
            580                 585                 590

Gly Thr Ile Asn Ser Pro Thr Val Ala Thr Gly Ser Phe Ser Ala Thr
        595                 600                 605

Ile Ile Ala Ser Leu Pro Ala Gly Ala Ala Val Ser Leu Gln Leu Phe
    610                 615                 620

Gly Val Val Ala Leu Ala Thr Leu Ser Thr Ala Thr Pro Gly Ala Thr
625                 630                 635                 640

Leu Thr Ile Ile Arg Leu Ser
                645


<210> SEQ ID NO 7
<211> LENGTH: 34
<212> TYPE: PRT
<213> ORGANISM: Bacillus anthracis

<400> SEQUENCE: 7

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly


<210> SEQ ID NO 8
<211> LENGTH: 366
<212> TYPE: PRT
<213> ORGANISM: Bacillus anthracis

<400> SEQUENCE: 8

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly Ile Thr Gly Ala Thr Gly Ala Thr Gly Ile Thr Gly Ala Thr
        35                  40                  45

Gly Pro Thr Gly Thr Thr Gly Ala Thr Gly Ala Thr Gly Ile Thr Gly
    50                  55                  60

Val Thr Gly Ala Thr Gly Ile Thr Gly Val Thr Gly Ala Thr Gly Ile
65                  70                  75                  80

Thr Gly Val Thr Gly Ala Thr Gly Ile Thr Gly Val Thr Gly Pro Thr
                85                  90                  95

Gly Ile Thr Gly Ala Thr Gly Pro Thr Gly Ile Thr Gly Ala Thr Gly
            100                 105                 110

Pro Ala Gly Ile Thr Gly Val Thr Gly Pro Thr Gly Ile Thr Gly Ala
        115                 120                 125

Thr Gly Pro Thr Gly Thr Thr Gly Val Thr Gly Pro Thr Gly Asp Thr
    130                 135                 140
```

```
Gly Leu Ala Gly Ala Thr Gly Pro Thr Gly Ala Thr Gly Leu Ala Gly
145                 150                 155                 160

Ala Thr Gly Pro Thr Gly Asp Thr Gly Ala Thr Gly Pro Thr Gly Ala
                165                 170                 175

Thr Gly Leu Ala Gly Ala Thr Gly Pro Thr Gly Ala Thr Gly Leu Thr
            180                 185                 190

Gly Ala Thr Gly Ala Thr Gly Ala Thr Gly Gly Gly Ala Ile Ile Pro
        195                 200                 205

Phe Ala Ser Gly Thr Thr Pro Ala Leu Leu Val Asn Ala Val Leu Ala
    210                 215                 220

Asn Thr Gly Thr Leu Leu Gly Phe Gly Phe Ser Gln Pro Gly Ile Ala
225                 230                 235                 240

Pro Gly Val Gly Gly Thr Leu Thr Ile Leu Pro Gly Val Val Gly Asp
                245                 250                 255

Tyr Ala Phe Val Ala Pro Arg Asp Gly Ile Ile Thr Ser Leu Ala Gly
            260                 265                 270

Phe Phe Ser Ala Thr Ala Ala Leu Ala Pro Leu Thr Pro Val Gln Ile
        275                 280                 285

Gln Met Gln Ile Phe Ile Ala Pro Ala Ala Ser Asn Thr Phe Thr Pro
    290                 295                 300

Val Ala Pro Pro Leu Leu Leu Thr Pro Ala Leu Pro Ala Ile Ala Ile
305                 310                 315                 320

Gly Thr Thr Ala Thr Gly Ile Gln Ala Tyr Asn Val Pro Val Val Ala
                325                 330                 335

Gly Asp Lys Ile Leu Val Tyr Val Ser Leu Thr Gly Ala Ser Pro Ile
            340                 345                 350

Ala Ala Val Ala Gly Phe Val Ser Ala Gly Leu Asn Ile Val
        355                 360                 365
```

<210> SEQ ID NO 9
<211> LENGTH: 30
<212> TYPE: PRT
<213> ORGANISM: Bacillus anthracis

<400> SEQUENCE: 9

```
Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly
            20                  25                  30
```

<210> SEQ ID NO 10
<211> LENGTH: 77
<212> TYPE: PRT
<213> ORGANISM: Bacillus anthracis

<400> SEQUENCE: 10

```
Met Asp Glu Phe Leu Ser Ser Ala Ala Leu Asn Pro Gly Ser Val Gly
1               5                   10                  15

Pro Thr Leu Pro Pro Met Gln Pro Phe Gln Phe Arg Thr Gly Pro Thr
            20                  25                  30

Gly Ser Thr Gly Ala Lys Gly Ala Ile Gly Asn Thr Glu Pro Tyr Trp
        35                  40                  45

His Thr Gly Pro Pro Gly Ile Val Leu Leu Thr Tyr Asp Phe Lys Ser
    50                  55                  60

Leu Ile Ile Ser Phe Ala Phe Arg Ile Leu Pro Ile Ser
65                  70                  75
```

<210> SEQ ID NO 11
<211> LENGTH: 39
<212> TYPE: PRT
<213> ORGANISM: Bacillus weihenstephensis

<400> SEQUENCE: 11

```
Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35
```

<210> SEQ ID NO 12
<211> LENGTH: 299
<212> TYPE: PRT
<213> ORGANISM: Bacillus weihenstephensis

<400> SEQUENCE: 12

```
Met Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Val Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Val Thr Gly Pro Thr Gly Glu Thr
        115                 120                 125

Gly Pro Thr Gly Gly Thr Glu Gly Cys Leu Cys Asp Cys Cys Val Leu
    130                 135                 140

Pro Met Gln Ser Val Leu Gln Gln Leu Ile Gly Glu Thr Val Ile Leu
145                 150                 155                 160

Gly Thr Ile Ala Asp Thr Pro Asn Thr Pro Pro Leu Phe Phe Leu Phe
                165                 170                 175

Thr Ile Thr Ser Val Asn Asp Phe Leu Val Thr Val Thr Asp Gly Thr
            180                 185                 190

Thr Thr Phe Val Val Asn Ile Ser Asp Val Thr Gly Val Gly Phe Leu
        195                 200                 205

Pro Pro Gly Pro Pro Ile Thr Leu Leu Pro Pro Thr Asp Val Gly Cys
    210                 215                 220

Glu Cys Glu Cys Arg Glu Arg Pro Ile Arg Gln Leu Leu Asp Ala Phe
225                 230                 235                 240

Ile Gly Ser Thr Val Ser Leu Leu Ala Ser Asn Gly Ser Ile Ala Ala
                245                 250                 255

Asp Phe Ser Val Glu Gln Thr Gly Leu Gly Ile Val Leu Gly Thr Leu
            260                 265                 270

Pro Ile Asn Pro Thr Thr Thr Val Arg Phe Ala Ile Ser Thr Cys Lys
        275                 280                 285
```

```
Ile Thr Ala Val Asn Ile Thr Pro Ile Thr Met
    290                 295


<210> SEQ ID NO 13
<211> LENGTH: 39
<212> TYPE: PRT
<213> ORGANISM: Bacillus weihenstephensis

<400> SEQUENCE: 13

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly
        35


<210> SEQ ID NO 14
<211> LENGTH: 289
<212> TYPE: PRT
<213> ORGANISM: Bacillus weihenstephensis

<400> SEQUENCE: 14

Met Phe Asp Lys Asn Glu Met Lys Lys Thr Asn Glu Val Leu Gln Ala
1               5                   10                  15

Asn Ala Leu Asp Pro Asn Ile Ile Gly Pro Thr Leu Pro Pro Ile Pro
            20                  25                  30

Pro Phe Thr Leu Pro Thr Gly Pro Thr Gly Pro Thr Gly Pro Thr Gly
        35                  40                  45

Pro Thr Gly Pro Thr Gly Pro Thr Gly Pro Thr Gly Pro Thr Gly Pro
    50                  55                  60

Thr Gly Pro Thr Gly Pro Thr Gly Pro Thr Gly Pro Thr Gly Leu Thr
65                  70                  75                  80

Gly Pro Thr Gly Pro Thr Gly Leu Thr Gly Pro Thr Gly Leu Thr Gly
                85                  90                  95

Pro Thr Gly Pro Thr Gly Leu Thr Gly Gln Thr Gly Ser Thr Gly Pro
            100                 105                 110

Thr Gly Ala Thr Glu Gly Cys Leu Cys Asp Cys Cys Val Phe Pro Met
        115                 120                 125

Gln Glu Val Leu Arg Gln Leu Val Gly Gln Thr Val Ile Leu Ala Thr
    130                 135                 140

Ile Ala Asp Ala Pro Asn Val Ala Pro Arg Phe Phe Leu Phe Asn Ile
145                 150                 155                 160

Thr Ser Val Asn Asp Phe Leu Val Thr Val Thr Asp Pro Val Ser Asn
                165                 170                 175

Thr Thr Phe Val Val Asn Ile Ser Asp Val Ile Gly Val Gly Phe Ser
            180                 185                 190

Leu Thr Val Pro Pro Leu Thr Leu Leu Pro Pro Ala Asp Leu Gly Cys
        195                 200                 205

Glu Cys Asp Cys Arg Glu Arg Pro Ile Arg Glu Leu Leu Asp Thr Leu
    210                 215                 220

Ile Gly Ser Thr Val Asn Leu Leu Val Ser Asn Gly Ser Ile Ala Thr
225                 230                 235                 240

Gly Phe Asn Val Glu Gln Thr Ala Leu Gly Ile Val Ile Gly Thr Leu
                245                 250                 255

Pro Ile Pro Ile Asn Pro Pro Pro Pro Thr Leu Phe Arg Phe Ala Ile
            260                 265                 270
```

-continued

```
Ser Thr Cys Lys Ile Thr Ala Val Asp Ile Thr Pro Thr Pro Thr Ala
        275                 280                 285

Thr


<210> SEQ ID NO 15
<211> LENGTH: 49
<212> TYPE: PRT
<213> ORGANISM: Bacillus cereus

<400> SEQUENCE: 15

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly


<210> SEQ ID NO 16
<211> LENGTH: 189
<212> TYPE: PRT
<213> ORGANISM: Bacillus cereus

<400> SEQUENCE: 16

Met Ser Arg Lys Asp Lys Phe Asn Arg Ser Arg Met Ser Arg Lys Asp
1               5                   10                  15

Arg Phe Asn Ser Pro Lys Ile Lys Ser Glu Ile Ser Ile Ser Pro Asp
            20                  25                  30

Leu Val Gly Pro Thr Phe Pro Pro Ile Pro Ser Phe Thr Leu Pro Thr
        35                  40                  45

Gly Ile Thr Gly Pro Thr Phe Asn Ile Asn Phe Arg Ala Glu Lys Asn
    50                  55                  60

Val Ala Gln Ser Phe Thr Pro Pro Ala Asp Ile Gln Val Ser Tyr Gly
65                  70                  75                  80

Asn Ile Ile Phe Asn Asn Gly Gly Gly Tyr Ser Ser Val Thr Asn Thr
                85                  90                  95

Phe Thr Ala Pro Ile Asn Gly Ile Tyr Leu Phe Ser Ala Ser Ile Gly
            100                 105                 110

Phe Asn Pro Thr Leu Gly Thr Thr Ser Thr Leu Arg Ile Thr Ile Arg
        115                 120                 125

Lys Asn Leu Val Ser Val Ala Ser Gln Thr Gly Thr Ile Thr Thr Gly
    130                 135                 140

Gly Thr Pro Gln Leu Glu Ile Thr Thr Ile Ile Asp Leu Leu Ala Ser
145                 150                 155                 160

Gln Thr Ile Asp Ile Gln Phe Ser Ala Ala Glu Ser Gly Thr Leu Thr
                165                 170                 175

Val Gly Ser Ser Asn Phe Phe Ser Gly Ala Leu Leu Pro
            180                 185


<210> SEQ ID NO 17
<211> LENGTH: 33
<212> TYPE: PRT
<213> ORGANISM: Bacillus cereus

<400> SEQUENCE: 17

Met Asn Glu Glu Tyr Ser Ile Leu His Gly Pro Ala Leu Glu Pro Asn
1               5                   10                  15
```

```
Leu Ile Gly Pro Thr Leu Pro Ser Ile Pro Pro Phe Thr Phe Pro Thr
            20                  25                  30

Gly


<210> SEQ ID NO 18
<211> LENGTH: 84
<212> TYPE: PRT
<213> ORGANISM: Bacillus cereus

<400> SEQUENCE: 18

Met Asn Glu Glu Tyr Ser Ile Leu His Gly Pro Ala Leu Glu Pro Asn
1               5                   10                  15

Leu Ile Gly Pro Thr Leu Pro Ser Ile Pro Pro Phe Thr Phe Pro Thr
            20                  25                  30

Gly Pro Thr Gly Ile Thr Gly Pro Thr Gly Ala Thr Gly Phe Thr Gly
        35                  40                  45

Ile Gly Ile Thr Gly Pro Thr Gly Val Thr Gly Pro Thr Gly Ile Gly
    50                  55                  60

Ile Thr Gly Pro Thr Gly Ala Thr Gly Pro Thr Gly Ile Gly Ile Thr
65                  70                  75                  80

Gly Pro Thr Gly


<210> SEQ ID NO 19
<211> LENGTH: 39
<212> TYPE: PRT
<213> ORGANISM: Bacillus cereus

<400> SEQUENCE: 19

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly
        35


<210> SEQ ID NO 20
<211> LENGTH: 1056
<212> TYPE: PRT
<213> ORGANISM: Bacillus cereus

<400> SEQUENCE: 20

Met Lys Asn Arg Asp Asn Asn Arg Lys Gln Asn Ser Leu Ser Ser Asn
1               5                   10                  15

Phe Arg Ile Pro Pro Glu Leu Ile Gly Pro Thr Phe Pro Pro Val Pro
            20                  25                  30

Thr Gly Phe Thr Gly Ile Gly Ile Thr Gly Pro Thr Gly Pro Gln Gly
        35                  40                  45

Pro Thr Gly Pro Gln Gly Pro Arg Gly Leu Gln Gly Pro Met Gly Glu
    50                  55                  60

Met Gly Pro Thr Gly Pro Gln Gly Val Gln Gly Ile Gln Gly Ser Val
65                  70                  75                  80

Gly Pro Ile Gly Ala Thr Gly Pro Glu Gly Gln Gln Gly Pro Gln Gly
                85                  90                  95

Leu Arg Gly Pro Gln Gly Glu Thr Gly Ala Thr Gly Pro Gly Gly Val
            100                 105                 110

Gln Gly Leu Gln Gly Pro Ile Gly Pro Thr Gly Ala Thr Gly Ala Gln
        115                 120                 125
```

```
Gly Ile Gln Gly Ile Gln Gly Leu Gln Gly Pro Ile Gly Ala Thr Gly
    130                 135                 140

Pro Glu Gly Ser Gln Gly Ile Gln Gly Val Gln Gly Leu Pro Gly Ala
145                 150                 155                 160

Thr Gly Pro Gln Gly Ile Gln Gly Ala Gln Gly Ile Gln Gly Thr Pro
                165                 170                 175

Gly Pro Ser Gly Asn Thr Gly Ala Thr Gly Ala Thr Gly Ala Thr Gly
            180                 185                 190

Gln Gly Ile Thr Gly Pro Thr Gly Ile Thr Gly Pro Thr Gly Ile Thr
        195                 200                 205

Gly Pro Ser Gly Gly Pro Pro Gly Pro Thr Gly Pro Thr Gly Ala Thr
    210                 215                 220

Gly Pro Gly Gly Gly Pro Ser Gly Ser Thr Gly Ala Thr Gly Ala Thr
225                 230                 235                 240

Gly Asn Thr Gly Ala Thr Gly Ser Thr Gly Val Thr Gly Ala Thr Gly
                245                 250                 255

Ser Thr Gly Pro Thr Gly Ser Thr Gly Ala Gln Gly Leu Gln Gly Ile
            260                 265                 270

Gln Gly Ile Gln Gly Pro Ile Gly Pro Thr Gly Pro Glu Gly Ser Gln
        275                 280                 285

Gly Ile Gln Gly Ile Pro Gly Pro Thr Gly Val Thr Gly Glu Gln Gly
    290                 295                 300

Ile Gln Gly Val Gln Gly Ile Gln Gly Ala Thr Gly Ala Thr Gly Asp
305                 310                 315                 320

Gln Gly Pro Gln Gly Ile Gln Gly Val Ile Gly Pro Gln Gly Val Thr
                325                 330                 335

Gly Ala Thr Gly Asp Gln Gly Pro Gln Gly Ile Gln Gly Val Pro Gly
            340                 345                 350

Pro Ser Gly Glu Thr Gly Pro Gln Gly Val Gln Gly Ile Gln Gly Pro
        355                 360                 365

Met Gly Asp Ile Gly Pro Thr Gly Pro Glu Gly Pro Glu Gly Leu Gln
    370                 375                 380

Gly Pro Gln Gly Ile Gln Gly Val Pro Gly Pro Val Gly Ala Thr Gly
385                 390                 395                 400

Pro Glu Gly Pro Gln Gly Ile Gln Gly Ile Gln Gly Pro Val Gly Ala
                405                 410                 415

Thr Gly Pro Gln Gly Pro Gln Gly Ile Gln Gly Ile Gln Gly Val Gln
            420                 425                 430

Gly Ile Thr Gly Ala Thr Gly Val Gln Gly Ala Thr Gly Ile Gln Gly
        435                 440                 445

Ile Gln Gly Glu Ile Gly Ala Thr Gly Pro Glu Gly Pro Gln Gly Val
    450                 455                 460

Gln Gly Ala Gln Gly Ala Ile Gly Pro Thr Gly Pro Met Gly Pro Gln
465                 470                 475                 480

Gly Val Gln Gly Val Gln Gly Ile Gln Gly Ala Thr Gly Ala Gln Gly
                485                 490                 495

Val Gln Gly Pro Gln Gly Ile Gln Gly Ile Gln Gly Pro Thr Gly Ala
            500                 505                 510

Thr Gly Asp Met Gly Ala Thr Gly Ala Thr Gly Glu Gly Thr Thr Gly
        515                 520                 525

Pro Thr Gly Val Thr Gly Pro Thr Gly Val Thr Gly Pro Ser Gly Gly
    530                 535                 540

Pro Ala Gly Pro Thr Gly Pro Thr Gly Pro Ser Gly Pro Ala Gly Val
```

-continued

```
545                 550                 555                 560

Thr Gly Pro Ser Gly Gly Pro Pro Gly Pro Thr Gly Ala Thr Gly Ala
                565                 570                 575

Thr Gly Val Thr Gly Asp Thr Gly Ala Thr Gly Ser Thr Gly Val Thr
            580                 585                 590

Gly Ala Thr Gly Glu Thr Gly Ala Thr Gly Val Thr Gly Leu Gln Gly
        595                 600                 605

Pro Gln Gly Ile Gln Gly Val Gln Gly Glu Ile Gly Pro Thr Gly Pro
    610                 615                 620

Gln Gly Val Gln Gly Pro Gln Gly Ile Gln Gly Val Thr Gly Ala Thr
625                 630                 635                 640

Gly Asp Gln Gly Pro Gln Gly Ile Gln Gly Pro Gln Gly Asp Ile Gly
                645                 650                 655

Pro Thr Gly Pro Gln Gly Ile Gln Gly Pro Gln Gly Ser Gln Gly Ile
            660                 665                 670

Gln Gly Ala Thr Gly Gly Thr Gly Ala Gln Gly Pro Gln Gly Ile Gln
        675                 680                 685

Gly Pro Gln Gly Asp Ile Gly Leu Thr Gly Ser Gln Gly Pro Thr Gly
    690                 695                 700

Ile Gln Gly Ile Gln Gly Glu Ile Gly Pro Thr Gly Pro Glu Gly Pro
705                 710                 715                 720

Glu Gly Leu Gln Gly Pro Gln Gly Ile Gln Gly Ile Gln Gly Pro Val
                725                 730                 735

Gly Ala Thr Gly Pro Glu Gly Pro Gln Gly Ile Gln Gly Ile Gln Gly
            740                 745                 750

Val Gln Gly Ala Thr Gly Pro Gln Gly Pro Gln Gly Ile Gln Gly Ile
        755                 760                 765

Gln Gly Val Gln Gly Ile Thr Gly Ala Thr Gly Ala Gln Gly Ala Thr
    770                 775                 780

Gly Ile Gln Gly Ile Gln Gly Glu Ile Gly Ala Thr Gly Pro Glu Gly
785                 790                 795                 800

Pro Gln Gly Val Gln Gly Ile Gln Gly Ala Ile Gly Pro Thr Gly Pro
                805                 810                 815

Met Gly Ala Gln Gly Val Gln Gly Ile Gln Gly Ile Gln Gly Ala Thr
            820                 825                 830

Gly Ala Gln Gly Val Gln Gly Pro Gln Gly Ile Gln Gly Val Gln Gly
        835                 840                 845

Pro Thr Gly Ala Thr Gly Glu Thr Gly Ala Thr Gly Ala Thr Gly Glu
    850                 855                 860

Gly Thr Thr Gly Pro Thr Gly Val Thr Gly Pro Thr Gly Val Thr Gly
865                 870                 875                 880

Pro Ser Gly Gly Pro Ala Gly Pro Thr Gly Pro Thr Gly Pro Ser Gly
                885                 890                 895

Pro Ala Gly Val Thr Gly Pro Ser Gly Gly Pro Pro Gly Pro Thr Gly
            900                 905                 910

Ala Thr Gly Ala Thr Gly Val Thr Gly Asp Thr Gly Ala Thr Gly Ser
        915                 920                 925

Thr Gly Val Thr Gly Ala Thr Gly Ala Thr Gly Ala Thr Gly Val Thr
    930                 935                 940

Gly Leu Gln Gly Pro Gln Gly Ile Gln Gly Val Gln Gly Glu Ile Gly
945                 950                 955                 960

Pro Thr Gly Pro Gln Gly Ile Gln Gly Pro Gln Gly Ile Gln Gly Val
                965                 970                 975
```

```
Thr Gly Ala Thr Gly Ala Gln Gly Pro Gln Gly Ile Gln Gly Pro Gln
            980                 985                 990

Gly Asp Ile Gly Pro Thr Gly Ser  Gln Gly Ile Gln Gly  Pro Gln Gly
        995                 1000                 1005

Pro Gln  Gly Ile Gln Gly Ala  Thr Gly Ala Thr Gly  Ala Gln Gly
    1010                 1015                 1020

Pro Gln  Gly Ile Gln Gly Pro  Gln Gly Glu Ile Gly  Pro Thr Gly
    1025                 1030                 1035

Pro Gln  Gly Pro Gln Gly Ile  Gln Gly Pro Gln Gly  Ile Gln Gly
    1040                 1045                 1050

Pro Thr  Gly
    1055


<210> SEQ ID NO 21
<211> LENGTH: 39
<212> TYPE: PRT
<213> ORGANISM: Bacillus weihenstephensis

<400> SEQUENCE: 21

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly
        35


<210> SEQ ID NO 22
<211> LENGTH: 365
<212> TYPE: PRT
<213> ORGANISM: Bacillus weihenstephensis

<400> SEQUENCE: 22

Met Ser Asp Lys His Gln Met Lys Lys Ile Ser Glu Val Leu Gln Ala
1               5                   10                  15

His Ala Leu Asp Pro Asn Leu Ile Gly Pro Pro Leu Pro Pro Ile Thr
            20                  25                  30

Pro Phe Thr Phe Pro Thr Gly Ser Thr Gly Pro Thr Gly Ser Thr Gly
        35                  40                  45

Ser Thr Gly Pro Thr Gly Ser Thr Gly Asn Thr Gly Pro Thr Gly Pro
    50                  55                  60

Thr Gly Pro Pro Val Gly Thr Asn Leu Asp Thr Ile Tyr Val Thr Asn
65                  70                  75                  80

Asp Ile Ser Asn Asn Val Ser Ala Ile Asp Gly Asn Thr Asn Thr Val
                85                  90                  95

Leu Thr Thr Ile Pro Val Gly Thr Asn Pro Val Gly Val Gly Val Asn
            100                 105                 110

Ser Ser Thr Asn Leu Ile Tyr Val Val Asn Asn Gly Ser Asp Asn Ile
        115                 120                 125

Ser Val Ile Asn Gly Ser Thr Asn Thr Val Val Ala Thr Ile Pro Val
    130                 135                 140

Gly Thr Gln Pro Phe Gly Val Gly Val Asn Pro Ser Thr Asn Leu Ile
145                 150                 155                 160

Tyr Val Ala Asn Arg Thr Ser Asn Asn Val Ser Val Ile Lys Gly Gly
                165                 170                 175

Thr Asn Thr Val Leu Thr Thr Ile Pro Val Gly Thr Asn Pro Val Gly
            180                 185                 190
```

-continued

Val Gly Val Asn Ser Ser Thr Asn Leu Ile Tyr Val Thr Asn Glu Ile
195 200 205

Pro Asn Ser Val Ser Val Ile Lys Gly Gly Thr Asn Thr Val Val Ala
210 215 220

Thr Ile Pro Val Gly Leu Phe Pro Phe Gly Val Gly Val Asn Ser Leu
225 230 235 240

Thr Asn Leu Ile Tyr Val Val Asn Asn Ser Pro His Asn Val Ser Val
245 250 255

Ile Asp Gly Asn Thr Asn Thr Val Leu Thr Thr Ile Ser Val Gly Thr
260 265 270

Ser Pro Val Gly Val Gly Val Asn Leu Ser Thr Asn Leu Ile Tyr Val
275 280 285

Ala Asn Glu Val Pro Asn Asn Ile Ser Val Ile Asn Gly Asn Thr Asn
290 295 300

Thr Val Leu Thr Thr Ile Pro Val Gly Thr Thr Pro Phe Glu Val Gly
305 310 315 320

Val Asn Ser Ser Thr Asn Leu Ile Tyr Val Ser Asn Leu Asn Ser Asn
325 330 335

Asn Val Ser Val Ile Asn Gly Ser Ala Asn Thr Val Ile Ala Thr Val
340 345 350

Pro Val Gly Ser Val Pro Arg Gly Ile Gly Val Lys Pro
355 360 365

<210> SEQ ID NO 23
<211> LENGTH: 30
<212> TYPE: PRT
<213> ORGANISM: Bacillus weihenstephensis

<400> SEQUENCE: 23

Met Asp Glu Phe Leu Ser Phe Ala Ala Leu Asn Pro Gly Ser Ile Gly
1 5 10 15

Pro Thr Leu Pro Pro Val Pro Pro Phe Gln Phe Pro Thr Gly
20 25 30

<210> SEQ ID NO 24
<211> LENGTH: 160
<212> TYPE: PRT
<213> ORGANISM: Bacillus weihenstephensis

<400> SEQUENCE: 24

Met Asp Glu Phe Leu Ser Phe Ala Ala Leu Asn Pro Gly Ser Ile Gly
1 5 10 15

Pro Thr Leu Pro Pro Val Pro Pro Phe Gln Phe Pro Thr Gly Pro Thr
20 25 30

Gly Ser Thr Gly Ser Thr Gly Pro Thr Gly Ser Thr Gly Ser Thr Gly
35 40 45

Pro Thr Gly Phe Asn Leu Pro Ala Gly Pro Ala Ser Ile Thr Leu Thr
50 55 60

Ser Asn Glu Thr Thr Ala Cys Val Ser Thr Gln Gly Asn Asn Thr Leu
65 70 75 80

Phe Phe Ser Gly Gln Val Leu Val Asn Gly Ser Pro Thr Pro Gly Val
85 90 95

Val Val Ser Phe Ser Phe Ser Asn Pro Ser Leu Ala Phe Met Val Pro
100 105 110

Leu Ala Val Ile Thr Asn Ala Ser Gly Asn Phe Thr Ala Val Phe Leu
115 120 125

```
Ala Ala Asn Gly Pro Gly Thr Val Thr Val Thr Ala Ser Leu Leu Asp
    130                 135                 140

Ser Pro Gly Thr Met Ala Ser Val Thr Ile Thr Ile Val Asn Cys Pro
145                 150                 155                 160


<210> SEQ ID NO 25
<211> LENGTH: 30
<212> TYPE: PRT
<213> ORGANISM: Bacillus weihenstephensis

<400> SEQUENCE: 25

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly
            20                  25                  30


<210> SEQ ID NO 26
<211> LENGTH: 69
<212> TYPE: PRT
<213> ORGANISM: Bacillus weihenstephensis

<400> SEQUENCE: 26

Met Asp Glu Phe Leu Ser Ser Thr Ala Leu Asn Pro Cys Ser Ile Gly
1               5                   10                  15

Pro Thr Leu Pro Pro Met Gln Pro Phe Gln Phe Pro Thr Gly Pro Thr
            20                  25                  30

Gly Ser Thr Gly Thr Thr Gly Pro Thr Gly Ser Ile Gly Pro Thr Gly
        35                  40                  45

Asn Thr Gly Leu Thr Gly Asn Thr Gly Pro Thr Gly Ile Thr Gly Pro
    50                  55                  60

Thr Gly Asp Thr Gly
65


<210> SEQ ID NO 27
<211> LENGTH: 36
<212> TYPE: PRT
<213> ORGANISM: Bacillus weihenstephensis

<400> SEQUENCE: 27

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly
        35


<210> SEQ ID NO 28
<211> LENGTH: 934
<212> TYPE: PRT
<213> ORGANISM: Bacillus weihenstephensis

<400> SEQUENCE: 28

Met Lys Glu Arg Asp Arg Gln Asn Ser Leu Asn Ser Asn Phe Arg Ile
1               5                   10                  15

Ser Pro Asn Leu Ile Gly Pro Thr Phe Pro Pro Val Pro Thr Gly Phe
            20                  25                  30

Thr Gly Ile Gly Ile Thr Gly Pro Thr Gly Pro Gln Gly Pro Thr Gly
        35                  40                  45

Pro Gln Gly Pro Arg Gly Phe Gln Gly Pro Met Gly Glu Met Gly Pro
```

-continued

```
    50                  55                  60

Thr Gly Pro Gln Gly Val Gln Gly Ile Gln Gly Pro Ala Gly Gln Met
65                  70                  75                  80

Gly Ala Thr Gly Pro Glu Gly Gln Gln Gly Pro Gln Gly Leu Arg Gly
                85                  90                  95

Pro Gln Gly Glu Thr Gly Ala Thr Gly Pro Gln Gly Val Gln Gly Leu
            100                 105                 110

Gln Gly Pro Ile Gly Pro Thr Gly Ala Thr Gly Ala Gln Gly Ile Gln
        115                 120                 125

Gly Ile Gln Gly Leu Gln Gly Pro Ile Gly Ala Thr Gly Pro Glu Gly
    130                 135                 140

Pro Gln Gly Ile Gln Gly Val Gln Gly Val Pro Gly Ala Thr Gly Ser
145                 150                 155                 160

Gln Gly Ile Gln Gly Ala Gln Gly Ile Gln Gly Pro Gln Gly Pro Ser
                165                 170                 175

Gly Asn Thr Gly Ala Thr Gly Val Thr Gly Gln Gly Ile Ser Gly Pro
            180                 185                 190

Thr Gly Ile Thr Gly Pro Thr Gly Ile Thr Gly Pro Ser Gly Gly Pro
        195                 200                 205

Pro Gly Pro Thr Gly Ala Thr Gly Ala Thr Gly Pro Gly Gly Gly Pro
    210                 215                 220

Ser Gly Ser Thr Gly Ala Thr Gly Ala Thr Gly Asn Thr Gly Val Thr
225                 230                 235                 240

Gly Ser Ala Gly Val Thr Gly Asn Thr Gly Ser Thr Gly Ser Thr Gly
                245                 250                 255

Glu Thr Gly Ala Gln Gly Leu Gln Gly Ile Gln Gly Val Gln Gly Pro
            260                 265                 270

Ile Gly Pro Thr Gly Pro Glu Gly Pro Gln Gly Ile Gln Gly Ile Pro
        275                 280                 285

Gly Pro Thr Gly Val Thr Gly Glu Gln Gly Ile Gln Gly Val Gln Gly
    290                 295                 300

Ile Gln Gly Ile Thr Gly Ala Thr Gly Asp Gln Gly Pro Gln Gly Ile
305                 310                 315                 320

Gln Gly Ala Ile Gly Pro Gln Gly Ile Thr Gly Ala Thr Gly Asp Gln
                325                 330                 335

Gly Pro Gln Gly Ile Gln Gly Val Pro Gly Pro Thr Gly Asp Thr Gly
            340                 345                 350

Ser Gln Gly Val Gln Gly Ile Gln Gly Pro Met Gly Asp Ile Gly Pro
        355                 360                 365

Thr Gly Pro Glu Gly Pro Glu Gly Leu Gln Gly Pro Gln Gly Ile Gln
    370                 375                 380

Gly Val Pro Gly Pro Ala Gly Ala Thr Gly Pro Glu Gly Pro Gln Gly
385                 390                 395                 400

Ile Gln Gly Ile Gln Gly Pro Ile Gly Val Thr Gly Pro Glu Gly Pro
                405                 410                 415

Gln Gly Ile Gln Gly Ile Gln Gly Ile Gln Gly Ile Thr Gly Ala Thr
            420                 425                 430

Gly Ala Gln Gly Ala Thr Gly Val Gln Gly Val Gln Gly Asn Ile Gly
        435                 440                 445

Ala Thr Gly Pro Glu Gly Pro Gln Gly Val Gln Gly Thr Gln Gly Asp
    450                 455                 460

Ile Gly Pro Thr Gly Pro Met Gly Pro Gln Gly Val Gln Gly Ile Gln
465                 470                 475                 480
```

-continued

```
Gly Ile Gln Gly Pro Thr Gly Ala Gln Gly Val Gln Gly Pro Gln Gly
                485                 490                 495

Ile Gln Gly Ile Gln Gly Pro Thr Gly Val Thr Gly Asp Thr Gly Thr
            500                 505                 510

Thr Gly Ala Thr Gly Glu Gly Thr Thr Gly Ala Thr Gly Val Thr Gly
        515                 520                 525

Pro Ser Gly Val Thr Gly Pro Ser Gly Gly Pro Ala Gly Pro Thr Gly
    530                 535                 540

Pro Thr Gly Pro Ser Gly Pro Thr Gly Leu Thr Gly Pro Ser Gly Gly
545                 550                 555                 560

Pro Pro Gly Pro Thr Gly Ala Thr Gly Val Thr Gly Gly Val Gly Asp
                565                 570                 575

Thr Gly Ala Thr Gly Ser Thr Gly Val Thr Gly Ala Thr Gly Val Thr
            580                 585                 590

Gly Ala Thr Gly Ala Thr Gly Leu Gln Gly Pro Gln Gly Ile Gln Gly
        595                 600                 605

Val Gln Gly Asp Ile Gly Pro Thr Gly Pro Gln Gly Val Gln Gly Pro
    610                 615                 620

Gln Gly Ile Gln Gly Ile Thr Gly Ala Thr Gly Asp Gln Gly Pro Gln
625                 630                 635                 640

Gly Ile Gln Gly Pro Gln Gly Ile Gln Gly Pro Thr Gly Pro Gln Gly
                645                 650                 655

Ile Gln Gly Gly Gln Gly Pro Gln Gly Ile Gln Gly Ala Thr Gly Ala
            660                 665                 670

Thr Gly Ala Gln Gly Pro Gln Gly Ile Gln Gly Ile Gln Gly Val Gln
        675                 680                 685

Gly Pro Thr Gly Pro Gln Gly Pro Thr Gly Ile Gln Gly Val Gln Gly
    690                 695                 700

Glu Ile Gly Pro Thr Gly Pro Gln Gly Val Gln Gly Leu Gln Gly Pro
705                 710                 715                 720

Gln Gly Pro Thr Gly Asp Thr Gly Pro Thr Gly Pro Gln Gly Pro Gln
                725                 730                 735

Gly Ile Gln Gly Pro Thr Gly Ala Thr Gly Ala Thr Gly Ser Gln Gly
            740                 745                 750

Ile Gln Gly Pro Thr Gly Ala Thr Gly Ala Thr Gly Ser Gln Gly Ile
        755                 760                 765

Gln Gly Pro Thr Gly Ala Thr Gly Ala Thr Gly Ala Thr Gly Ala Thr
    770                 775                 780

Gly Ala Thr Gly Ala Thr Gly Ala Thr Gly Val Thr Gly Val Ser Thr
785                 790                 795                 800

Thr Ala Thr Tyr Ser Phe Ala Asn Asn Thr Ser Gly Ser Ala Ile Ser
                805                 810                 815

Val Leu Leu Gly Gly Thr Asn Ile Pro Leu Pro Asn Asn Gln Asn Ile
            820                 825                 830

Gly Pro Gly Ile Thr Val Ser Gly Gly Asn Thr Val Phe Thr Val Thr
        835                 840                 845

Asn Ala Gly Asn Tyr Tyr Ile Ala Tyr Thr Ile Asn Ile Thr Ala Ala
    850                 855                 860

Leu Leu Val Ser Ser Arg Ile Thr Val Asn Gly Ser Pro Leu Ala Gly
865                 870                 875                 880

Thr Ile Asn Ser Pro Ala Val Ala Thr Gly Ser Phe Asn Ala Thr Ile
                885                 890                 895
```

```
Ile Ser Asn Leu Ala Ala Gly Ser Ala Ile Ser Leu Gln Leu Phe Gly
            900                 905                 910

Leu Leu Ala Val Ala Thr Leu Ser Thr Thr Thr Pro Gly Ala Thr Leu
        915                 920                 925

Thr Ile Ile Arg Leu Ser
    930


<210> SEQ ID NO 29
<211> LENGTH: 39
<212> TYPE: PRT
<213> ORGANISM: Bacillus mycoides

<400> SEQUENCE: 29

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly
        35


<210> SEQ ID NO 30
<211> LENGTH: 287
<212> TYPE: PRT
<213> ORGANISM: Bacillus mycoides

<400> SEQUENCE: 30

Val Phe Asp Lys Asn Glu Ile Gln Lys Ile Asn Gly Ile Leu Gln Ala
1               5                   10                  15

Asn Ala Leu Asn Pro Asn Leu Ile Gly Pro Thr Leu Pro Pro Ile Pro
            20                  25                  30

Pro Phe Thr Leu Pro Thr Gly Pro Thr Gly Gly Thr Gly Pro Thr Gly
        35                  40                  45

Val Thr Gly Pro Thr Gly Val Thr Gly Pro Thr Gly Val Thr Gly Pro
    50                  55                  60

Thr Gly Val Thr Gly Pro Thr Gly Val Thr Gly Pro Thr Gly Val Thr
65                  70                  75                  80

Gly Pro Thr Gly Val Thr Gly Pro Thr Gly Val Thr Gly Pro Thr Gly
                85                  90                  95

Val Thr Gly Pro Thr Gly Val Thr Gly Pro Thr Gly Val Thr Gly Pro
            100                 105                 110

Thr Gly Val Thr Gly Pro Thr Gly Gly Thr Glu Gly Cys Leu Cys Asp
        115                 120                 125

Cys Cys Val Leu Pro Met Gln Ser Val Leu Gln Gln Leu Ile Gly Glu
    130                 135                 140

Thr Val Ile Leu Gly Thr Ile Ala Asp Thr Pro Asn Thr Pro Pro Leu
145                 150                 155                 160

Phe Phe Leu Phe Thr Ile Thr Ser Val Asn Asp Phe Leu Val Thr Val
                165                 170                 175

Thr Asp Gly Thr Thr Thr Phe Val Val Asn Ile Ser Asp Val Thr Gly
            180                 185                 190

Val Gly Phe Leu Pro Pro Gly Pro Pro Ile Thr Leu Leu Pro Pro Thr
        195                 200                 205

Asp Val Gly Cys Glu Cys Glu Cys Arg Glu Arg Pro Ile Arg Gln Leu
    210                 215                 220

Leu Asp Ala Phe Ile Gly Ser Thr Val Ser Leu Leu Ala Ser Asn Gly
225                 230                 235                 240
```

-continued

```
Ser Ile Ala Ala Asp Phe Ser Val Glu Gln Thr Gly Leu Gly Ile Val
                245                 250                 255

Leu Gly Thr Leu Pro Ile Asn Pro Thr Thr Thr Val Arg Phe Ala Ile
            260                 265                 270

Ser Thr Cys Lys Ile Thr Ala Val Asn Ile Thr Pro Ile Thr Met
        275                 280                 285
```

<210> SEQ ID NO 31
<211> LENGTH: 30
<212> TYPE: PRT
<213> ORGANISM: Bacillus mycoides

<400> SEQUENCE: 31

```
Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly
            20                  25                  30
```

<210> SEQ ID NO 32
<211> LENGTH: 190
<212> TYPE: PRT
<213> ORGANISM: Bacillus mycoides

<400> SEQUENCE: 32

```
Met Asp Glu Phe Leu Tyr Phe Ala Ala Leu Asn Pro Gly Ser Ile Gly
1               5                   10                  15

Pro Thr Leu Pro Pro Val Gln Pro Phe Gln Phe Pro Thr Gly Pro Thr
            20                  25                  30

Gly Ser Thr Gly Ala Thr Gly Ser Thr Gly Ser Thr Gly Ser Thr Gly
        35                  40                  45

Pro Thr Gly Ser Thr Gly Ser Thr Gly Ser Thr Gly Ser Thr Gly Pro
    50                  55                  60

Thr Gly Pro Thr Gly Pro Thr Gly Ser Thr Gly Pro Thr Gly Pro Thr
65                  70                  75                  80

Gly Phe Asn Leu Pro Ala Gly Pro Ala Ser Ile Thr Leu Thr Ser Asn
                85                  90                  95

Glu Thr Thr Ala Cys Val Ser Thr Gln Gly Asn Asn Thr Leu Phe Phe
            100                 105                 110

Ser Gly Gln Val Leu Val Asn Gly Ser Pro Thr Pro Gly Val Val Val
        115                 120                 125

Ser Phe Ser Phe Ser Asn Pro Ser Leu Ala Phe Met Val Pro Leu Ala
    130                 135                 140

Val Ile Thr Asn Ala Ser Gly Asn Phe Thr Ala Val Phe Leu Ala Ala
145                 150                 155                 160

Asn Gly Pro Gly Thr Val Thr Val Thr Ala Ser Leu Leu Asp Ser Pro
                165                 170                 175

Gly Thr Met Ala Ser Val Thr Ile Thr Ile Val Asn Cys Pro
            180                 185                 190
```

<210> SEQ ID NO 33
<211> LENGTH: 21
<212> TYPE: PRT
<213> ORGANISM: Bacillus mycoides

<400> SEQUENCE: 33

```
Met Asp Ser Lys Asn Ile Gly Pro Thr Phe Pro Pro Leu Pro Ser Ile
1               5                   10                  15

Asn Phe Pro Thr Gly
```

20

<210> SEQ ID NO 34
<211> LENGTH: 335
<212> TYPE: PRT
<213> ORGANISM: Bacillus mycoides

<400> SEQUENCE: 34

Met Asp Ser Lys Asn Ile Gly Pro Thr Phe Pro Pro Leu Pro Ser Ile
1 5 10 15

Asn Phe Pro Thr Gly Val Thr Gly Glu Thr Gly Ala Thr Gly Glu Thr
20 25 30

Gly Ala Thr Gly Ala Thr Gly Glu Thr Gly Ala Thr Gly Glu Thr Gly
35 40 45

Glu Thr Gly Ala Thr Gly Ala Thr Gly Ala Thr Gly Ala Thr Gly Glu
50 55 60

Thr Gly Ala Thr Gly Ala Thr Gly Ala Thr Gly Ala Ala Gly Ala Thr
65 70 75 80

Gly Glu Thr Gly Ala Thr Gly Glu Thr Gly Ala Thr Gly Glu Thr Gly
85 90 95

Ala Thr Gly Glu Thr Gly Ala Thr Gly Val Thr Gly Glu Thr Gly Ala
100 105 110

Thr Gly Glu Thr Gly Ala Ala Gly Glu Thr Gly Ile Thr Gly Val Thr
115 120 125

Gly Pro Thr Gly Glu Thr Gly Ala Thr Gly Glu Thr Gly Ala Thr Gly
130 135 140

Ala Thr Gly Ile Thr Gly Ala Thr Gly Ile Thr Gly Val Ala Gly Ala
145 150 155 160

Thr Gly Glu Thr Gly Ala Ala Gly Glu Thr Gly Pro Thr Gly Ala Thr
165 170 175

Gly Ala Ile Gly Ala Ile Gly Ala Thr Gly Ala Thr Gly Ile Thr Gly
180 185 190

Val Thr Gly Ala Thr Gly Glu Thr Gly Ala Ala Gly Ala Thr Gly Ile
195 200 205

Thr Gly Val Thr Gly Ala Thr Gly Glu Thr Gly Ala Ala Gly Ala Thr
210 215 220

Gly Ile Thr Gly Ala Thr Gly Ile Thr Gly Val Ala Gly Ala Thr Gly
225 230 235 240

Ile Thr Gly Pro Thr Gly Ile Pro Gly Thr Ile Pro Thr Thr Asn Leu
245 250 255

Leu Tyr Phe Thr Phe Ser Asp Gly Glu Lys Leu Ile Tyr Thr Asn Ala
260 265 270

Asp Gly Ile Ala Gln Tyr Gly Thr Thr Gln Ile Leu Ser Pro Ser Glu
275 280 285

Val Ser Tyr Ile Asn Leu Phe Ile Asn Gly Ile Leu Gln Pro Gln Pro
290 295 300

Phe Tyr Glu Val Thr Ala Gly Gln Leu Thr Leu Leu Asp Asp Glu Pro
305 310 315 320

Pro Ser Gln Gly Ser Ser Ile Ile Leu Gln Phe Ile Ile Ile Asn
325 330 335

<210> SEQ ID NO 35
<211> LENGTH: 22
<212> TYPE: PRT
<213> ORGANISM: Bacillus thuringiensis

<400> SEQUENCE: 35

```
Met Ile Gly Pro Glu Asn Ile Gly Pro Thr Phe Pro Ile Leu Pro Pro
1               5                   10                  15

Ile Tyr Ile Pro Thr Gly
            20
```

<210> SEQ ID NO 36
<211> LENGTH: 234
<212> TYPE: PRT
<213> ORGANISM: Bacillus thuringiensis

<400> SEQUENCE: 36

```
Met Ile Gly Pro Glu Asn Ile Gly Pro Thr Phe Pro Ile Leu Pro Pro
1               5                   10                  15

Ile Tyr Ile Pro Thr Gly Glu Thr Gly Pro Thr Gly Ile Thr Gly Ala
            20                  25                  30

Thr Gly Glu Thr Gly Pro Thr Gly Ile Thr Gly Pro Thr Gly Ile Thr
        35                  40                  45

Gly Ala Thr Gly Glu Thr Gly Ser Thr Gly Ile Thr Gly Ala Thr Gly
    50                  55                  60

Glu Thr Gly Ser Thr Gly Ile Thr Gly Pro Ile Gly Ile Thr Gly Ala
65                  70                  75                  80

Thr Gly Glu Thr Gly Pro Ile Gly Ile Thr Gly Ala Thr Gly Glu Thr
                85                  90                  95

Gly Pro Thr Gly Ile Thr Gly Ser Thr Gly Ile Thr Gly Leu Thr Gly
            100                 105                 110

Val Thr Gly Leu Thr Gly Glu Thr Gly Pro Ile Gly Ile Thr Gly Pro
        115                 120                 125

Thr Gly Ile Thr Gly Pro Thr Gly Val Thr Gly Ala Thr Gly Pro Thr
    130                 135                 140

Gly Gly Ile Gly Pro Ile Thr Thr Thr Asn Leu Leu Tyr Tyr Thr Phe
145                 150                 155                 160

Ala Asp Gly Glu Lys Leu Ile Tyr Thr Asp Thr Asp Gly Ile Pro Gln
                165                 170                 175

Tyr Gly Thr Thr Asn Ile Leu Ser Pro Ser Glu Val Ser Tyr Ile Asn
            180                 185                 190

Leu Phe Val Asn Gly Ile Leu Gln Pro Gln Pro Leu Tyr Glu Val Ser
        195                 200                 205

Thr Gly Lys Leu Thr Leu Leu Asp Thr Gln Pro Pro Ser Gln Gly Ser
    210                 215                 220

Ser Ile Ile Leu Gln Phe Ile Ile Ile Asn
225                 230
```

<210> SEQ ID NO 37
<211> LENGTH: 23
<212> TYPE: DNA
<213> ORGANISM: Artificial sequence
<220> FEATURE:
<223> OTHER INFORMATION: Primer

<400> SEQUENCE: 37

```
ggatccatgg ctgaacacaa tcc                                              23
```

<210> SEQ ID NO 38
<211> LENGTH: 24
<212> TYPE: DNA
<213> ORGANISM: Artificial sequence
<220> FEATURE:

-continued

```
<223> OTHER INFORMATION: Primer

<400> SEQUENCE: 38

ggatccttaa ttcgtattct ggcc                                        24


<210> SEQ ID NO 39
<211> LENGTH: 21
<212> TYPE: DNA
<213> ORGANISM: Artificial sequence
<220> FEATURE:
<223> OTHER INFORMATION: Primer

<400> SEQUENCE: 39

ggatccatga aacggtcaat c                                           21


<210> SEQ ID NO 40
<211> LENGTH: 24
<212> TYPE: DNA
<213> ORGANISM: Artificial sequence
<220> FEATURE:
<223> OTHER INFORMATION: Primer

<400> SEQUENCE: 40

ggatccttac taatttggtt ctgt                                        24


<210> SEQ ID NO 41
<211> LENGTH: 21
<212> TYPE: DNA
<213> ORGANISM: Artificial sequence
<220> FEATURE:
<223> OTHER INFORMATION: Primer

<400> SEQUENCE: 41

ggatccatgc taccaaaagc c                                           21


<210> SEQ ID NO 42
<211> LENGTH: 24
<212> TYPE: DNA
<213> ORGANISM: Artificial sequence
<220> FEATURE:
<223> OTHER INFORMATION: Primer

<400> SEQUENCE: 42

ggatccttag tccgcaggcg tagc                                        24
```